(12) United States Patent
Nomura et al.

(10) Patent No.: US 8,329,917 B2
(45) Date of Patent: Dec. 11, 2012

(54) HETEROCYCLIC COMPOUND AND LIGHT-EMITTING ELEMENT, LIGHT-EMITTING DEVICE, LIGHTING DEVICE, AND ELECTRONIC DEVICE USING THE SAME

(75) Inventors: Hiroko Nomura, Fukuoka (JP); Sachiko Kawakami, Kanagawa (JP); Nobuharu Ohsawa, Kanagawa (JP); Satoshi Seo, Kanagawa (JP)

(73) Assignee: Semiconductor Energy Laboratory Co., Ltd., Atsugi-shi, Kanagawa-ken (JP)

( * ) Notice: Subject to any disclaimer, the term of this patent is extended or adjusted under 35 U.S.C. 154(b) by 98 days.

(21) Appl. No.: 12/748,188

(22) Filed: Mar. 26, 2010

(65) Prior Publication Data
US 2010/0244670 A1    Sep. 30, 2010

(30) Foreign Application Priority Data

Mar. 31, 2009 (JP) .................................. 2009-086617

(51) Int. Cl.
$C07D\ 413/10$   (2006.01)
$B32B\ 9/00$   (2006.01)
$H01J\ 1/62$   (2006.01)

(52) U.S. Cl. ........ 548/224; 548/215; 548/217; 428/690; 428/917; 313/504; 313/506

(58) Field of Classification Search ............... 548/217, 548/224; 428/690, 917; 313/504, 506
See application file for complete search history.

(56) References Cited

U.S. PATENT DOCUMENTS

| | | | |
|---|---|---|---|
| 7,796,240 B2 | 9/2010 | Nomura et al. | |
| 7,838,128 B2 | 11/2010 | Kawakami et al. | |
| 7,875,879 B2 | 1/2011 | Suzuki et al. | |
| 7,880,019 B2 * | 2/2011 | Egawa et al. ............. | 548/439 |
| 7,883,788 B2 | 2/2011 | Kawakami et al. | |
| 7,901,792 B2 | 3/2011 | Egawa et al. | |
| 7,927,720 B2 | 4/2011 | Nomura et al. | |
| 7,998,596 B2 * | 8/2011 | Yabunouchi et al. ....... | 428/690 |
| 8,093,399 B2 * | 1/2012 | Nomura et al. ............ | 548/224 |
| 2007/0161793 A1 | 7/2007 | Murata et al. | |
| 2007/0222374 A1 | 9/2007 | Egawa et al. | |
| 2009/0045725 A1 | 2/2009 | Fukushima et al. | |
| 2010/0060155 A1 | 3/2010 | Seo et al. | |

FOREIGN PATENT DOCUMENTS

| | | |
|---|---|---|
| CN | 101213237 A | 7/2008 |
| EP | 2 177 516 A1 | 4/2010 |
| WO | 2009/020095 A1 | 2/2009 |

OTHER PUBLICATIONS

M.A. Baldo et al.; "Very high-efficiency green organic light-emitting devices based on electrophosphorescence"; Applied Physics Letters (Applied Physics Letters); Jul. 5, 1999, pp. 4-6; vol. 75, No. 1.
Office Action, Chinese Application No. 201010158571.X, dated Aug. 3, 2012, 13 pages with full English translation.

* cited by examiner

Primary Examiner — Golam M M Shameem
(74) Attorney, Agent, or Firm — Fish & Richardson P.C.

(57) ABSTRACT

To provide a novel heterocyclic compound having a bipolar property. To improve element characteristics of a light-emitting element by application of the novel heterocyclic compound to the light-emitting element. A heterocyclic compound represented by a general formula (G1) and a light-emitting element formed using the heterocyclic compound represented by the general formula (G1) are provided. When the heterocyclic compound represented by the general formula (G1) is used for the light-emitting element, the characteristics of the light-emitting element can be improved.

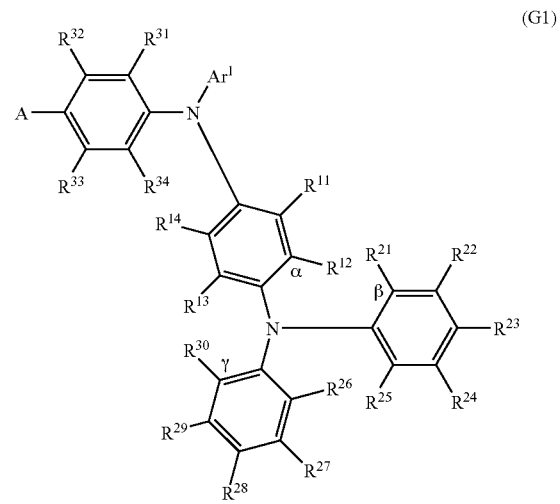

16 Claims, 28 Drawing Sheets

HETEROCYCLIC COMPOUND AND LIGHT-EMITTING ELEMENT, LIGHT-EMITTING DEVICE, LIGHTING DEVICE, AND ELECTRONIC DEVICE USING THE SAME

BACKGROUND OF THE INVENTION

1. Field of the Invention

The present invention relates to a heterocyclic compound and a light-emitting element, a light-emitting device, a lighting device, and an electronic device using the heterocyclic compound.

2. Description of the Related Art

In recent years, research and development have been actively conducted on light-emitting elements using electroluminescence (EL). In a basic structure of such a light-emitting element, a layer containing a substance having a light-emitting property is interposed between a pair of electrodes. By application of a voltage to this element, light emission can be obtained from the substance having a light-emitting property.

Since such a light-emitting element is of self-light-emitting type, the light-emitting element has advantages over a liquid crystal display in that visibility of pixels is high, backlight is not needed, and so on. Therefore, such a light-emitting element is thought to be suitable as a flat panel display element. Besides, such a light-emitting element has advantages in that it can be formed to be thin and lightweight, and has quite fast response speed.

Furthermore, since such a light-emitting element can be formed in a film form, planar light emission can be easily obtained by formation of an element having a large area. This is a feature which is difficult to be obtained by point light sources typified by an incandescent lamp and an LED or linear light sources typified by a fluorescent lamp. Therefore, the light-emitting element has a high utility value as a surface light source applicable to illumination and the like.

Light-emitting elements using electroluminescence are broadly classified according to whether they use an organic compound or an inorganic compound as a light-emitting substance. When an organic compound is used as a light-emitting substance, by application of a voltage to a light-emitting element, electrons and holes are injected into a layer containing the light-emitting organic compound from a pair of electrodes, and thus a current flows. The carriers (electrons and holes) are recombined, and thus, the light-emitting organic compound is excited. When the light-emitting organic compound returns to a ground state from the excited state, light is emitted.

Because of such a mechanism, the light-emitting element is referred to as a current-excitation light-emitting element. Note that an excited state of an organic compound can be of two types: a singlet excited state and a triplet excited state, and light emission from the singlet excited state (S*) is referred to as fluorescence, and light emission from the triplet excited state (T*) is referred to as phosphorescence. In addition, the statistical generation ratio thereof in the light-emitting element is considered to be S*:T*=1:3.

At a room temperature, a compound capable of converting a singlet excited state to luminescence (hereinafter, referred to as a fluorescent compound) exhibits only luminescence from the singlet excited state (fluorescence), not luminescence from the triplet excited state (phosphorescence). Accordingly, the internal quantum efficiency (the ratio of the number of generated photons to the number of injected carriers) of a light-emitting element including the fluorescent compound is assumed to have a theoretical limit of 25%, on the basis of S*:T*=1:3.

On the other hand, in a case of a light-emitting element including the phosphorescent compound described above, the internal quantum efficiency thereof can be improved to 75% to 100% in theory; namely, the emission efficiency thereof can be 3 to 4 times as much as that of the light-emitting element including a fluorescent compound. Therefore, the light-emitting element including a phosphorescent compound has been actively developed in recent years in order to achieve a highly-efficient light-emitting element (refer to Non-Patent Document 1).

When a light-emitting layer of a light-emitting element is formed using the above phosphorescent compound, for suppression of the concentration quenching of the phosphorescent compound and the quenching due to triplet-triplet annihilation, the light-emitting layer is formed so that the phosphorescent compound is dispersed throughout a matrix formed of another material in many cases. In this case, the material used for forming the matrix is called a host material, and the material dispersed throughout the matrix like the phosphorescent material is called a guest material.

When a phosphorescent compound is used for a guest material, a host material is required to have higher triplet excitation energy (a difference in energy between the ground state and the triplet excited state) than the phosphorescent compound. CBP, which is used as the host material in Non-Patent Document 1, is known to have higher triplet excitation energy than a phosphorescent compound which exhibits light emission of green to red and is widely used as a host material with the phosphorescent compound.

However, although CBP has high triplet excitation energy, it is poor in capability to receive holes or electrons; therefore, there is a problem in that driving voltage is increased. Therefore, a substance which has high triplet excitation energy and also can easily accept or transport both holes and electrons (i.e., a bipolar substance) is needed as a host material for a phosphorescent compound.

Furthermore, since the singlet excitation energy (the difference in energy between the ground state and the singlet excited state) is higher than the triplet excitation energy, a substance which has high triplet excitation energy also has high singlet excitation, energy. Therefore, a substance which has high triplet excitation energy and a bipolar property as described above is also effective as a host material in a light-emitting element using a fluorescent compound as a light-emitting substance.

REFERENCE

[Non-Patent Document 1] M. A. Baldo, etc., *Applied Physics Letters*, vol. 75, No. 1, pp. 4-6, 1999

SUMMARY OF THE INVENTION

An object of an embodiment of the present invention is to provide a novel heterocyclic compound as a substance having high excitation energy, particularly a substance having high triplet excitation energy. Another object of an embodiment of the present invention is to provide a novel heterocyclic compound having a bipolar property. Another object of an embodiment of the present invention is to improve element characteristics of a light-emitting element by application of a novel heterocyclic compound to the light-emitting element.

An embodiment of the present invention is a heterocyclic compound represented by the following general formula (G1).

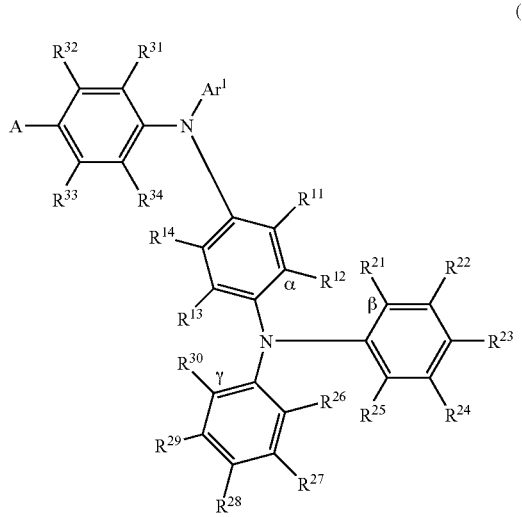

(G1)

In the formula, Ar¹ represents a substituted or unsubstituted aryl group having 6 to 10 carbon atoms which form a ring. $R^{11}$ to $R^{14}$ and $R^{31}$ to $R^{34}$ each independently represent any one of a hydrogen atom, an alkyl group having 1 to 4 carbon atoms, or an aryl group having 6 to 10 carbon atoms which form a ring. $R^{21}$ to $R^{30}$ each independently represent any one of a hydrogen atom, an alkyl group having 1 to 4 carbon atoms, or a substituted or unsubstituted aryl group having 6 to 10 carbon atoms which form a ring. A represents any one of substituents represented by the following general formulae (S1-1) to (S1-3). In addition, any two of a carbon atom α, a carbon atom β, and a carbon atom γ may be combined to form a carbazole ring.

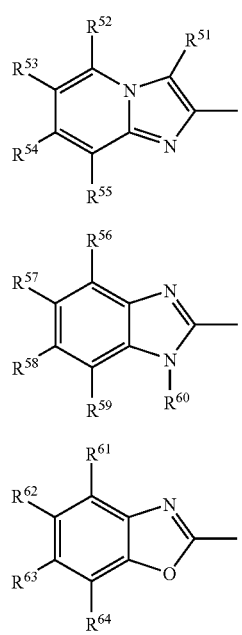

(S1-1)

(S1-2)

(S1-3)

In the general formulae (S1-1) to (S1-3), $R^{51}$ to $R^{64}$ each independently represent any one of a hydrogen atom, an alkyl group having 1 to 4 carbon atoms, or an aryl group having 6 to 10 carbon atoms which form a ring.

In the above heterocyclic compound represented by the general formula (G1), which is an embodiment of the present invention, A is preferably any one of a substituent represented by the following structural formula (S2-1), a substituent represented by the following structural formula (S2-2), or a substituent represented by the following general formula (S3-1).

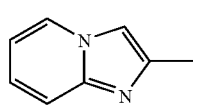

(S2-1)

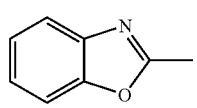

(S2-2)

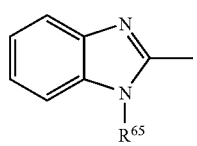

(S3-1)

In the general formula (S3-1), $R^{65}$ represents any one of a hydrogen atom, an alkyl group having 1 to 4 carbon atoms, or an aryl group having 6 to 10 carbon atoms which form a ring.

Another embodiment of the present invention is a heterocyclic compound represented by the following general formula (G2).

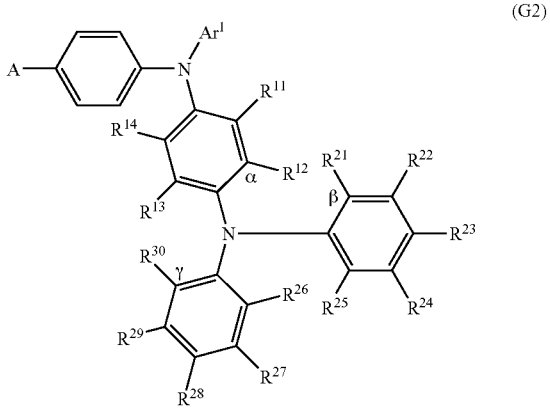

(G2)

In the formula, Ar¹ represents a substituted or unsubstituted aryl group having 6 to 10 carbon atoms which form a ring. $R^{11}$ to $R^{14}$ each independently represent any one of a hydrogen atom, an alkyl group having 1 to 4 carbon atoms, or an aryl group having 6 to 10 carbon atoms which form a ring. $R^{21}$ to $R^{30}$ each independently represent any one of a hydrogen atom, an alkyl group having 1 to 4 carbon atoms, or a substituted or unsubstituted aryl group having 6 to 10 carbon atoms which form a ring. A represents any one of a substituent represented by the following structural formula (S2-1), a substituent represented by the following structural formula (S2-2), or a substituent represented by the following general formula (S3-1). In addition, any two of a carbon atom α, a carbon atom β, and a carbon atom γ may be combined to form a carbazole ring.

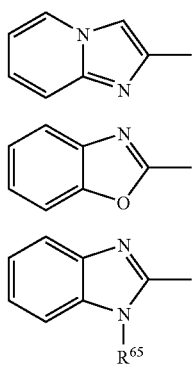

(S2-1)

(S2-2)

(S3-1)

In the general formula (S3-1), $R^{65}$ represents any one of a hydrogen atom, an alkyl group having 1 to 4 carbon atoms, or an aryl group having 6 to 10 carbon atoms which form a ring.

Another embodiment of the present invention is a heterocyclic compound represented by the following general formula (G3).

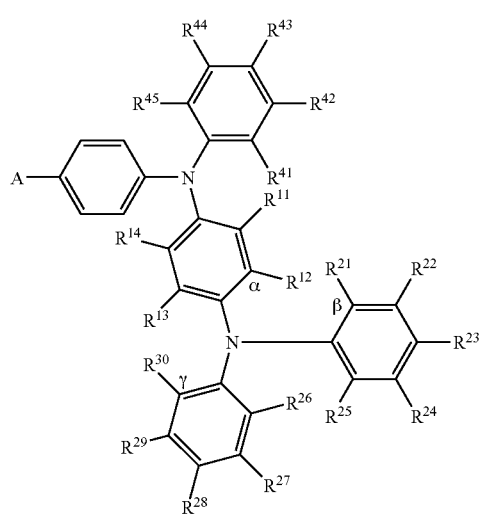

(G3)

$R^{11}$ to $R^{14}$ and $R^{41}$ to $R^{45}$ each independently represent any one of a hydrogen atom, an alkyl group having 1 to 4 carbon atoms, or an aryl group having 6 to 10 carbon atoms which form a ring. $R^{21}$ to $R^{30}$ each independently represent any one of a hydrogen atom, an alkyl group having 1 to 4 carbon atoms, or a substituted or unsubstituted aryl, group having 6 to 10 carbon atoms which form a ring. A represents any one of a substituent represented by the following structural formula (S2-1), a substituent represented by the following structural formula (S2-2), or a substituent represented by the following general formula (S3-1). In addition, any two of a carbon atom α, a carbon atom β, and a carbon atom γ may be combined to form a carbazole ring.

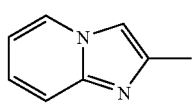

(S2-1)

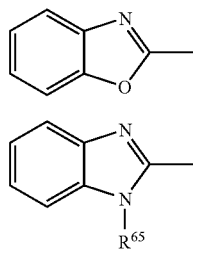

(S2-2)

(S3-1)

In the general formula (S3-1), $R^{65}$ represents any one of a hydrogen atom, an alkyl group having 1 to 4 carbon atoms, or an aryl group having 6 to 10 carbon atoms which form a ring.

Another embodiment of the present invention is a heterocyclic compound represented by the following general formula (G4).

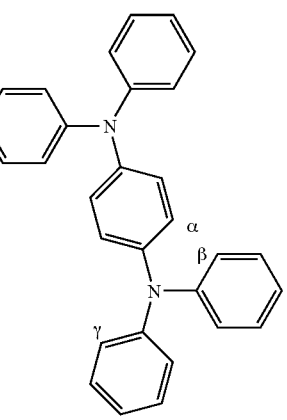

(G4)

In the formula, A represents any one of a substituent represented by the following structural formula (S2-1), a substituent represented by the following structural formula (S2-2), or a substituent represented by the following general formula (S3-1). In addition, any two of a carbon atom α, a carbon atom β, and a carbon atom γ may be combined to form a carbazole ring.

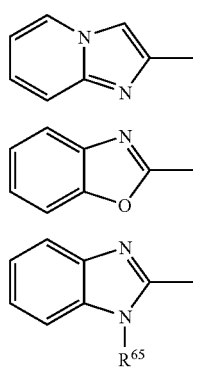

(S2-1)

(S2-2)

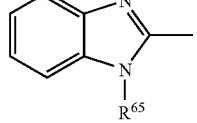

(S3-1)

In the general formula (S3-1), $R^{65}$ represents any one of a hydrogen atom, an alkyl group having 1 to 4 carbon atoms, or an aryl group having 6 to 10 carbon atoms which form a ring.

Note that the above heterocyclic compound which is an embodiment of the present invention has a light-emitting property; therefore, another embodiment of the present invention is a light-emitting element in which an EL layer containing the above heterocyclic compound is included between a pair of electrodes.

In addition, the above heterocyclic compound which is an embodiment of the present invention has high excitation energy. In addition, since the heterocyclic compound can transport both holes and electrons, it is suitable for as a host material of a light-emitting layer included in an EL layer. Therefore, another embodiment of the present invention is a light-emitting element in which an EL layer is included between a pair of electrodes, and a light-emitting layer included in the EL layer contains the above heterocyclic compound and a light-emitting substance.

In particular, the above heterocyclic compound which is an embodiment of the present invention has high triplet excitation energy; thus, a phosphorescent compound is preferable as the light-emitting substance contained in the light-emitting layer. With such a structure, a light-emitting element which is excellent in both emission efficiency and driving voltage can be obtained.

An embodiment of the present invention includes, in its category, a light-emitting device having the above light-emitting element and an electronic device having the light-emitting device. A light-emitting device in this specification refers to an image display device, a light-emitting device and a light source (including a lighting device). Further, the light-emitting device includes any of the following modules in its category: a module in which a connector such as a flexible printed circuit (FPC), a tape automated bonding (TAB) tape, or a tape carrier package (TCP) is attached to a light-emitting device; a module having a TAB tape or a TCP provided with a printed wiring board at the end thereof; and a module having an integrated circuit (IC) directly mounted over a light-emitting device by a chip on glass (COG) method.

According to an embodiment of the present invention, a heterocyclic compound having high excitation energy, particularly high triplet excitation energy can be provided. In addition, a heterocyclic compound having a bipolar property can be provided.

Further, when a light-emitting element is formed using the heterocyclic compound which is an embodiment of the present invention, characteristics of the light-emitting element can be improved.

Further, the use of this light-emitting element makes it possible to provide a light-emitting device and an electronic device which consume less power and have high efficiency.

DETAILED DESCRIPTION OF THE INVENTION

Figure 1:
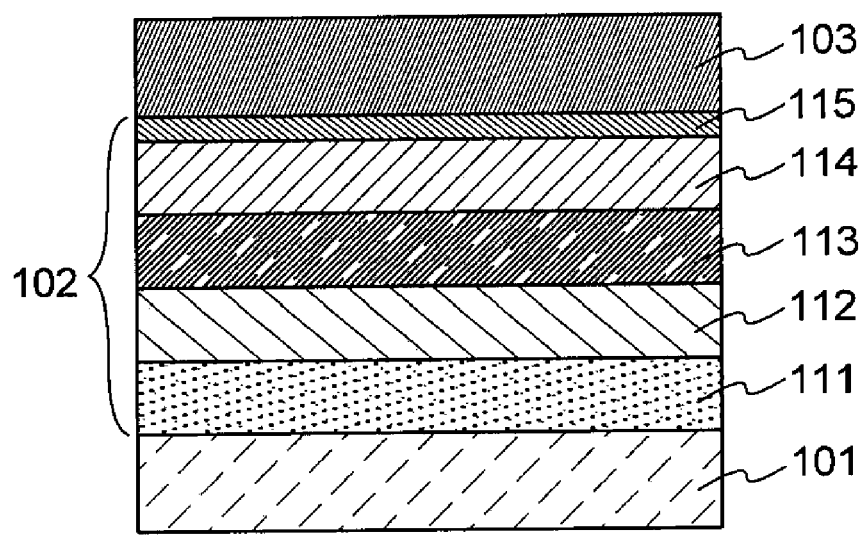
FIG. 1 is a view illustrating a light-emitting element.

Hereinafter, embodiments and examples will be described in detail with reference to the accompanying drawings. Note that the present invention is not limited to the description below, and modes and details thereof can be modified in various ways without departing from the spirit and the scope of the present invention. Therefore, the present invention should not be construed as being limited to the description of the following embodiments and examples.

Embodiment 1

In Embodiment 1, a heterocyclic compound which is an embodiment of the present invention will be described.

An embodiment of the present invention is a heterocyclic compound represented by the following general formula (G1).

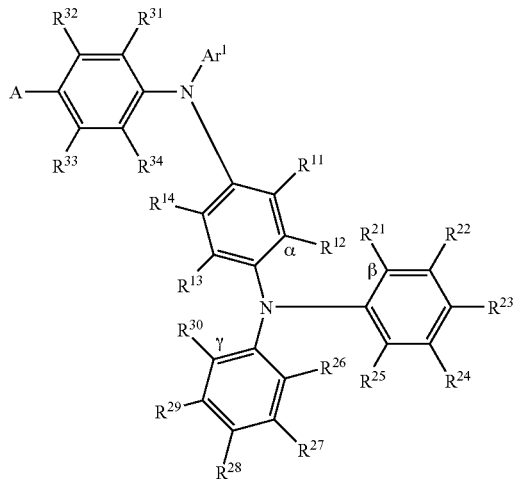

(G1)

In the formula, $Ar^1$ represents a substituted or unsubstituted aryl group having 6 to 10 carbon atoms which form a ring. $R^{11}$ to $R^{14}$ and $R^{31}$ to $R^{34}$ each independently represent any one of a hydrogen atom, an alkyl group having 1 to 4 carbon atoms, or an aryl group having 6 to 10 carbon atoms which form a ring. $R^{21}$ to $R^{30}$ each independently represent any one of a hydrogen atom, an alkyl group having 1 to 4 carbon atoms, or a substituted or unsubstituted aryl group having 6 to 10 carbon atoms which form a ring. A represents any one of substituents represented by the following general formulae (S1-1) to (S1-3). In addition, any two of a carbon atom α, a carbon atom β, and a carbon atom γ may be combined to form a carbazole ring.

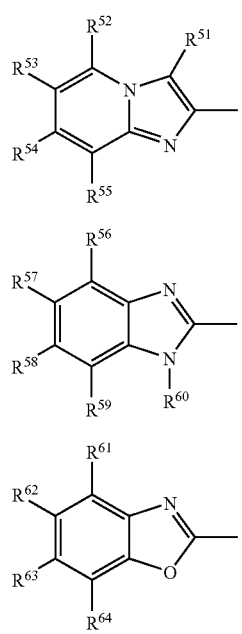

(S1-1)

(S1-2)

(S1-3)

In the general formulae (S1-1) to (S1-3), $R^{51}$ to $R^{64}$ each independently represent any one of a hydrogen atom, an alkyl group having 1 to 4 carbon atoms, or an aryl group having 6 to 10 carbon atoms which form a ring.

Note that $Ar^1$ in the general formula (G1) may further include a substituent. As examples of the substituent, an alkyl group having 1 to 4 carbon atoms, an aryl group having 6 to 10 carbon atoms which form a ring, and the like are given. As examples of a specific structure of $Ar^1$ in the general formula (G1), substituents represented by structural formulae (1-1) to (1-21) are given.

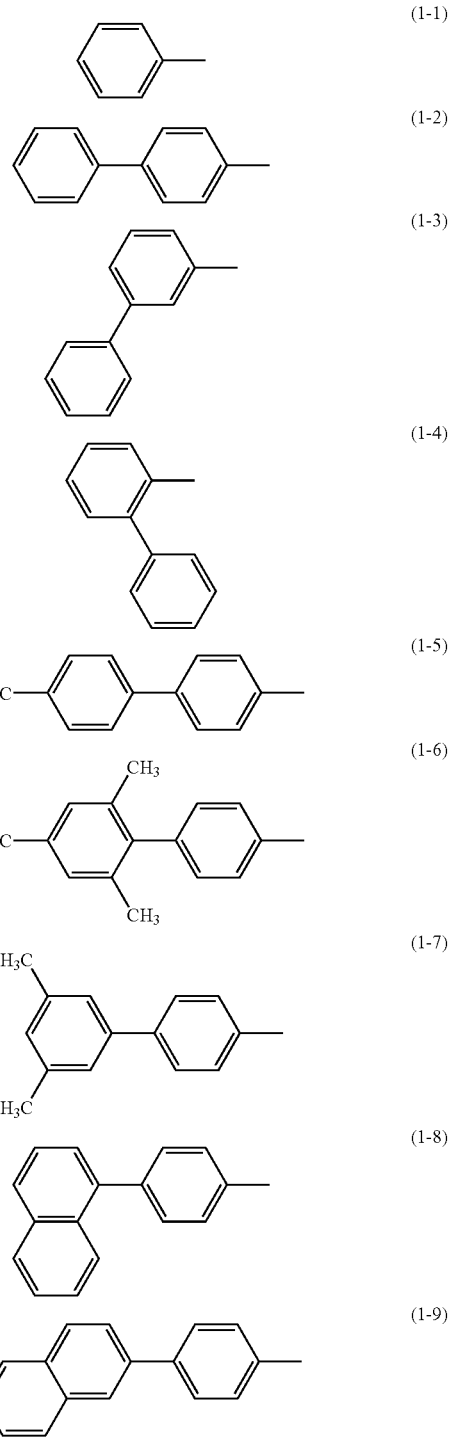

-continued
(1-10)
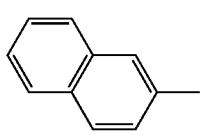
(1-11)
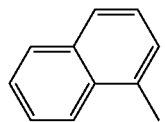
(1-12)
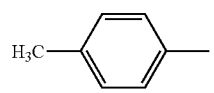
(1-13)
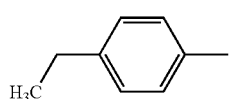
(1-14)
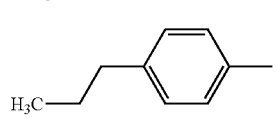
(1-15)
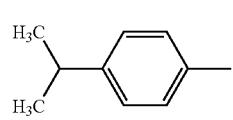
(1-16)
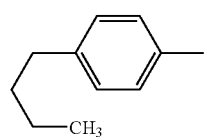
(1-17)
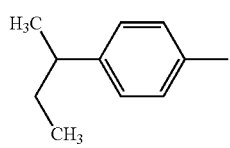
(1-18)
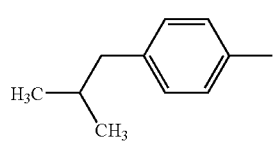
(1-19)
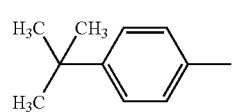
(1-20)
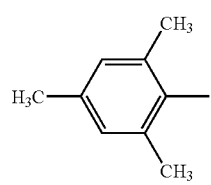
(1-21)
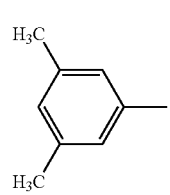
Further, as examples of specific structures of $R^{11}$ to $R^{14}$ and $R^{31}$ to $R^{34}$ in the general formula (G1), substituents represented by structural formulae (2-1) to (2-22) are given.
(2-1)
(2-2)
(2-3)
(2-4)
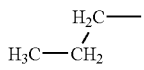
(2-5)
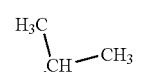
(2-6)
(2-7)
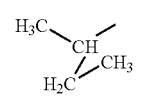
(2-8)
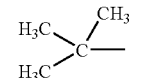
(2-9)
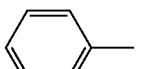
(2-10)
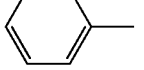
(2-11)
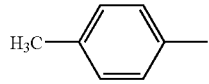
(2-12)
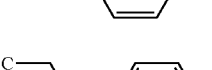
(2-13)
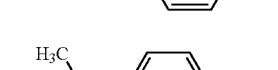
(2-14)
(2-15)
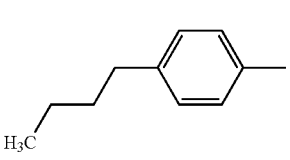

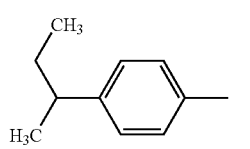 (2-16)

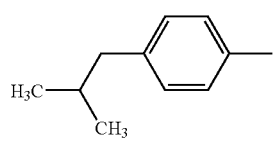 (2-17)

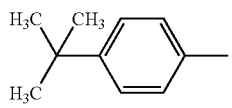 (2-18)

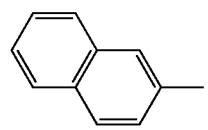 (2-19)

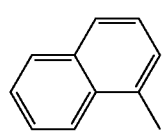 (2-20)

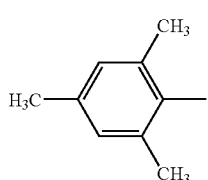 (2-21)

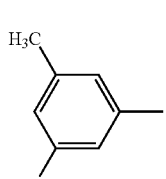 (2-22)

Further, $R^{21}$ to $R^{30}$ in the general formula (G1) may further include a substituent. As examples of the substituent, an alkyl group having 1 to 4 carbon atoms, an aryl group having 6 to 10 carbon atoms which form a ring, and the like are given. As examples of specific structures of $R^{21}$ to $R^{30}$ in the general formula (G1), substituents represented by structural formulae (3-1) to (3-30) are given.

 (3-1)

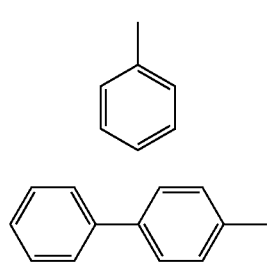 (3-2)

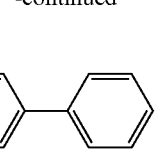 (3-3)

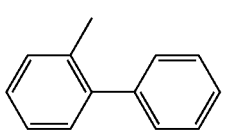 (3-4)

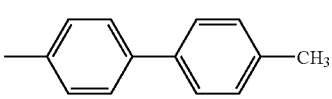 (3-5)

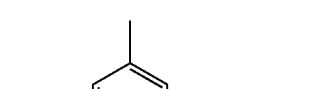 (3-6)

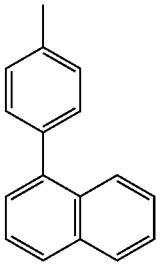

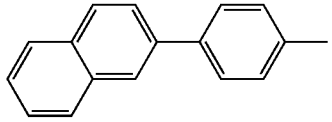 (3-7)

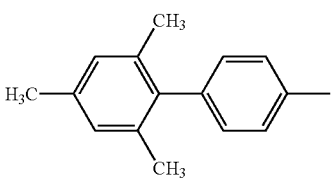 (3-8)

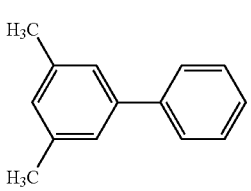 (3-9)

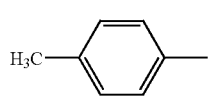 (3-10)

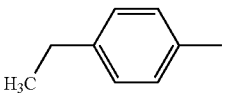 (3-11)

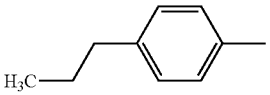 (3-12)

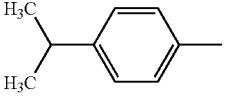 (3-13)

-continued

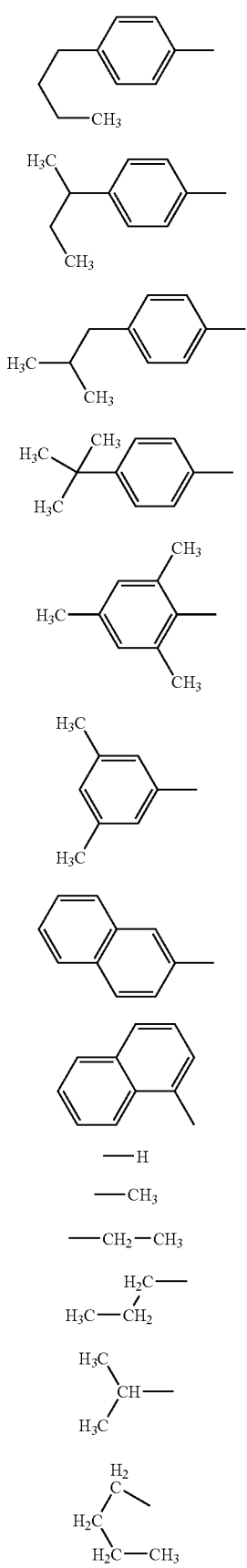

(3-14)
(3-15)
(3-16)
(3-17)
(3-18)
(3-19)
(3-20)
(3-21)
(3-22)
(3-23)
(3-24)
(3-25)
(3-26)
(3-27)

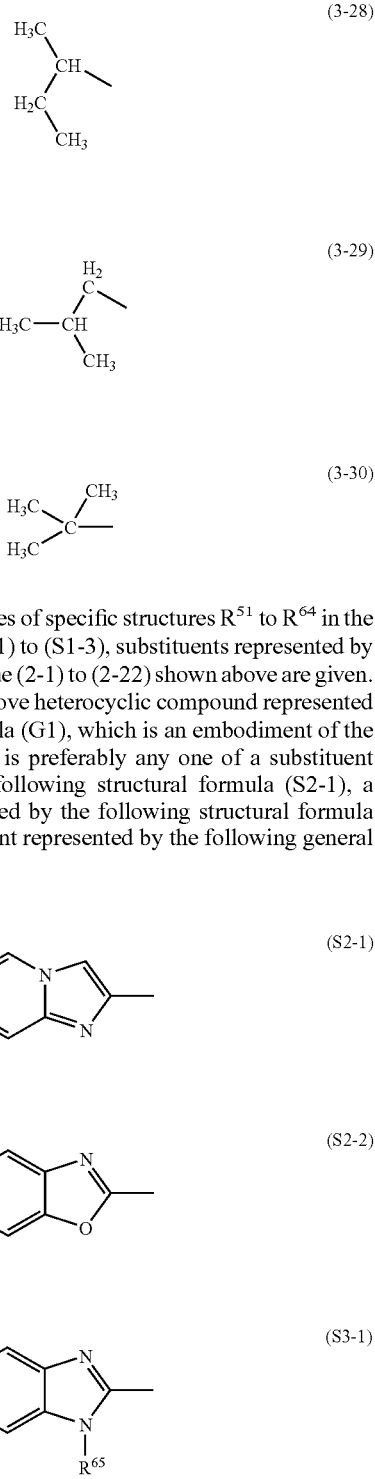

Further, as examples of specific structures $R^{51}$ to $R^{64}$ in the general formula (S1-1) to (S1-3), substituents represented by the structural formulae (2-1) to (2-22) shown above are given.

Note that in the above heterocyclic compound represented by the general formula (G1), which is an embodiment of the present invention, A is preferably any one of a substituent represented by the following structural formula (S2-1), a substituent represented by the following structural formula (S2-2), or a substituent represented by the following general formula (S3-1).

Note that in the general formula (S3-1), $R^{65}$ represents any one of a hydrogen atom, an alkyl group having 1 to 4 carbon atoms, or an aryl group having 6 to 10 carbon atoms which form a ring. Specifically, the substituents represented by the structural formulae (2-1) to (2-22) shown above, and the like are given as examples.

Another embodiment of the present invention is a heterocyclic compound represented by the following general formula (G2).

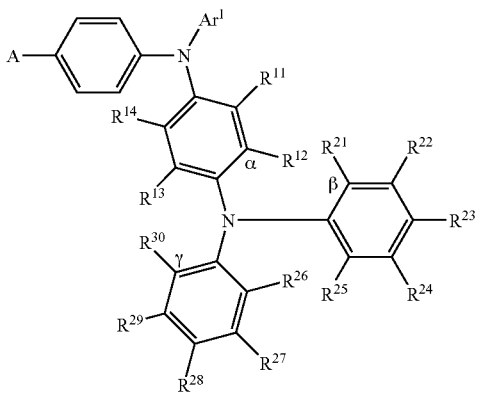
(G2)

In the formula, $Ar^1$ represents a substituted or unsubstituted aryl group having 6 to 10 carbon atoms which form a ring. $R^{11}$ to $R^{14}$ each independently represent any one of a hydrogen atom, an alkyl group having 1 to 4 carbon atoms, or an aryl group having 6 to 10 carbon atoms which form a ring. $R^{21}$ to $R^{30}$ each independently represent any one of a hydrogen atom, an alkyl group having 1 to 4 carbon atoms, or a substituted or unsubstituted aryl group having 6 to 10 carbon atoms which form a ring.

Note that $Ar^1$ in the general formula (G2) may further include a substituent. As examples of the substituent, an alkyl group having 1 to 4 carbon atoms, an aryl group having 6 to 10 carbon atoms which form a ring, and the like are given. As examples of a specific structure of $Ar^1$ in the general formula (G2), substituents represented by the structural formulae (1-1) to (1-21) shown above, and the like are given.

As examples of specific structures of $R^{11}$ to $R^{14}$ in the general formula (G2), substituents represented by the structural formulae (2-1) to (2-22) shown above are given.

Further, $R^{21}$ to $R^{30}$ in the general formula (G2) may further include a substituent. As examples of the substituent, an alkyl group having 1 to 4 carbon atoms, an aryl group having 6 to 10 carbon atoms which form a ring, and the like are given. As examples of specific structures of $R^{21}$ to $R^{30}$ in the general formula (G2), substituents represented by the structural formulae (3-1) to (3-22) shown above are given.

Further, in the general formula (G2), A represents any one of a substituent represented by the following structural formula (S2-1), a substituent represented by the following structural formula (S2-2), or a substituent represented by the following general formula (S3-1). In addition, any two of a carbon atom α, a carbon atom β, and a carbon atom γ may be combined to form a carbazole ring.

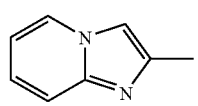
(S2-1)

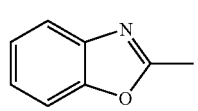
(S2-2)

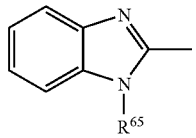
(S3-1)

In the general formula (S3-1), $R^{65}$ represents any one of a hydrogen atom, an alkyl group having 1 to 4 carbon atoms, or an aryl group having 6 to 10 carbon atoms which form a ring: Specifically, the substituents represented by the structural formulae (2-1) to (2-22) shown above, and the like are given as examples.

Another embodiment of the present invention is a heterocyclic compound represented by the following general formula (G3).

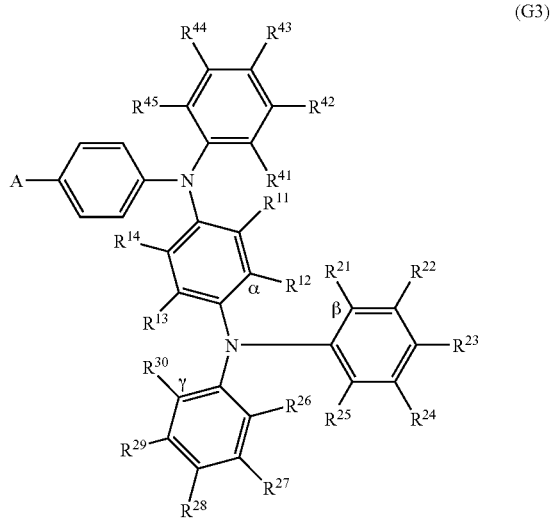
(G3)

In the formula, $R^{11}$ to $R^{14}$ and $R^{41}$ to $R^{45}$ each independently represent any one of a hydrogen atom, an alkyl group having 1 to 4 carbon atoms, or an aryl group having 6 to 10 carbon atoms which form a ring. $R^{21}$ to $R^{30}$ each independently represent any one of a hydrogen atom, an alkyl group having 1 to 4 carbon atoms, or a substituted or unsubstituted aryl group having 6 to 10 carbon atoms which form a ring.

As examples of specific structures of $R^{11}$ to $R^{14}$ and $R^{41}$ to $R^{45}$ in the general formula (G3), substituents represented by the structural formulae (2-1) to (2-22) shown above are given.

Further, $R^{21}$ to $R^{30}$ in the general formula (G3) may further include a substituent. As examples of the substituent, an alkyl group having 1 to 4 carbon atoms, an aryl group having 6 to 10 carbon atoms which form a ring, and the like are given. As examples of specific structures of $R^{21}$ to $R^{30}$ in the general formula (G3), substituents represented by the structural formulae (3-1) to (3-22) shown above are given.

Further, in the general formula (G3), A represents any one of a substituent represented by the following structural formula (S2-1), a substituent represented by the following structural formula (S2-2), or a substituent represented by the following general formula (S3-1). In addition, any two of a carbon atom α, a carbon atom β, and a carbon atom γ may be combined to form a carbazole ring.

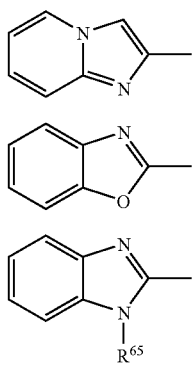  (S2-1)

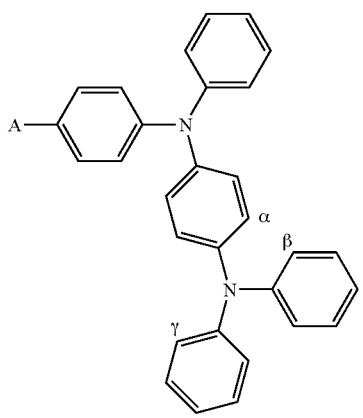  (S2-2)

(S3-1)

In the general formula (S3-1), $R^{65}$ represents any one of a hydrogen atom, an alkyl group having 1 to 4 carbon atoms, or an aryl group having 6 to 10 carbon atoms which form a ring. Specifically, the substituents represented by the structural formulae (2-1) to (2-22) shown above, and the like are given as examples.

Another embodiment of the present invention is a heterocyclic compound represented by the following general formula (G4).

(G4)

In the formula, A represents any one of a substituent represented by the following structural formula (S2-1), a substituent represented by the following structural formula (S2-2), or a substituent represented by the following general formula (S3-1). In addition, any two of a carbon atom α, a carbon atom β, and a carbon atom γ may be combined to form a carbazole ring.

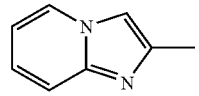  (S2-1)

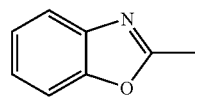  (S2-2)

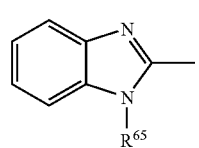  (S3-1)

Note that in the general formula (S3-1), $R^{65}$ represents any one of a hydrogen atom, an alkyl group having 1 to 4 carbon atoms, or an aryl group having 6 to 10 carbon atoms which form a ring. Specifically, the substituents represented by the structural formulae (2-1) to (2-22) shown above, and the like are given as examples.

As specific examples of the heterocyclic compound of this embodiment, which is represented by the general formula (G1), heterocyclic compounds represented by structural formulae (100) to (291) can be given. However, the present invention is not limited to these.

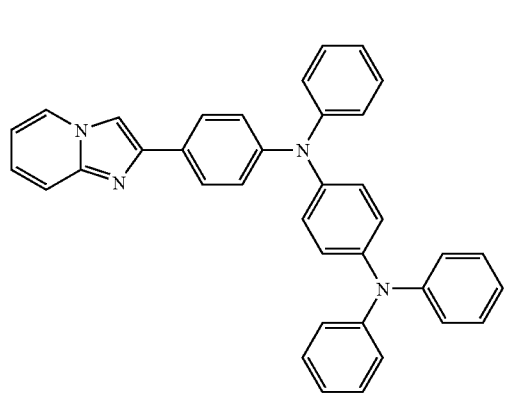  (100)

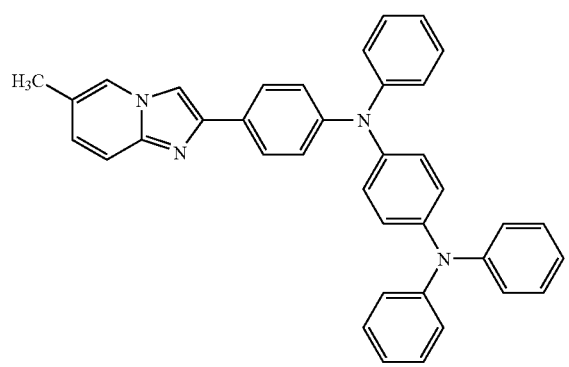  (101)

-continued
(102) 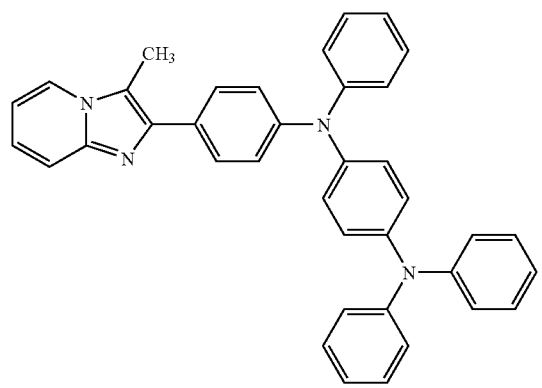
(103) 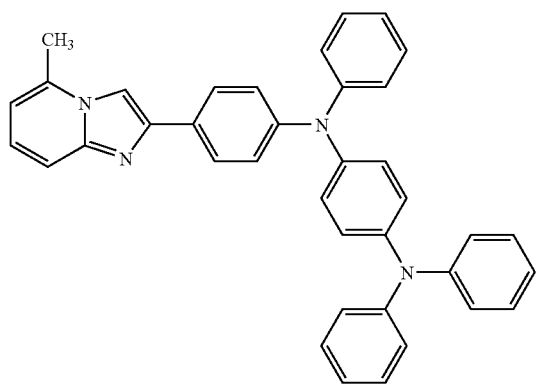
(104) 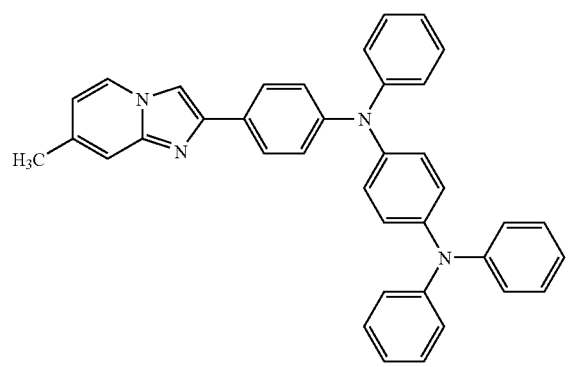
(105) 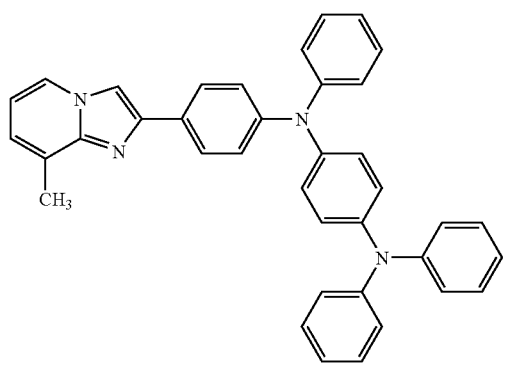
(106) 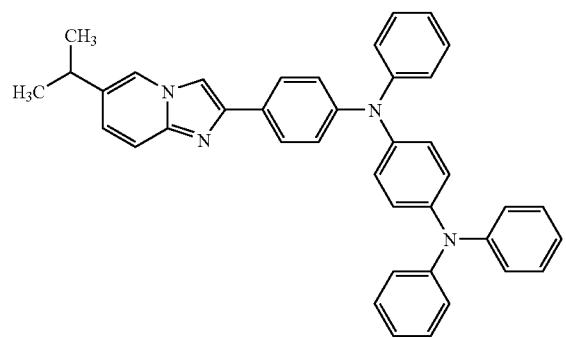
(107) 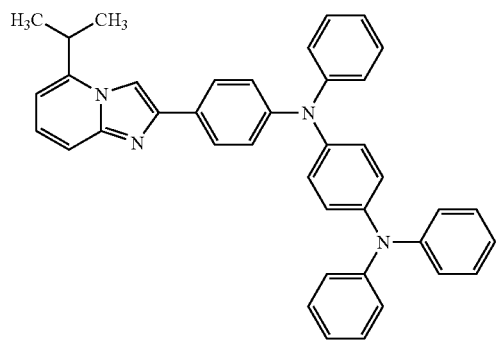
(108) 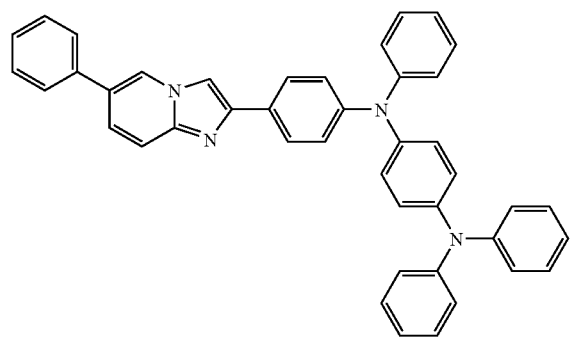
(109) 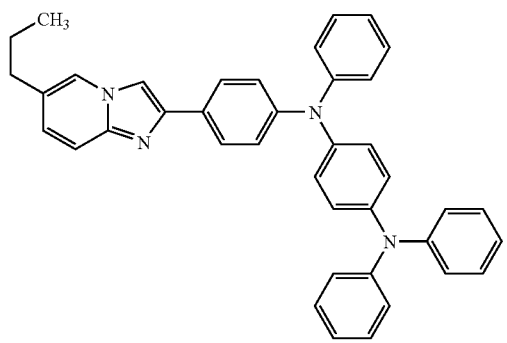

-continued
(110)
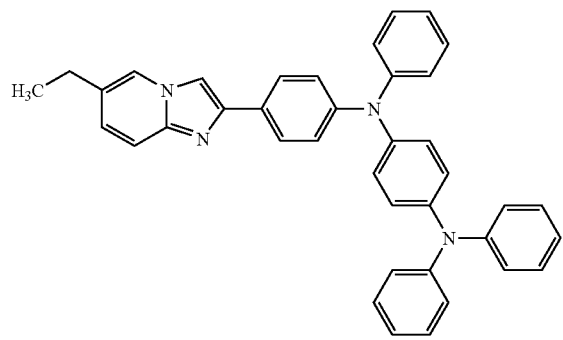
(111)
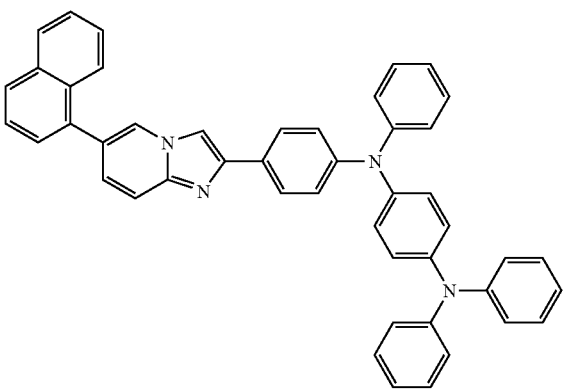
(112)
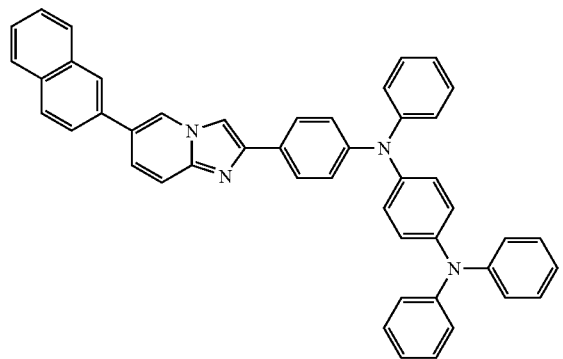
(113)
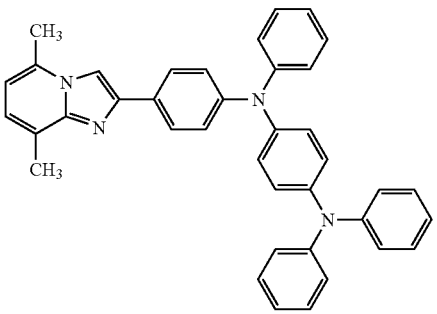
(114)
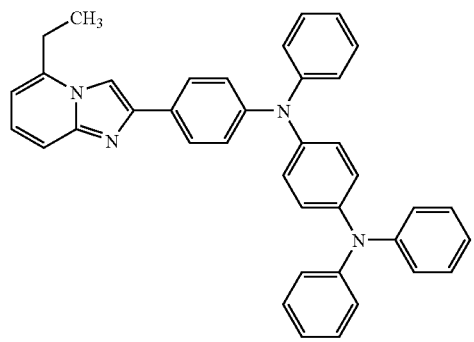
(115)
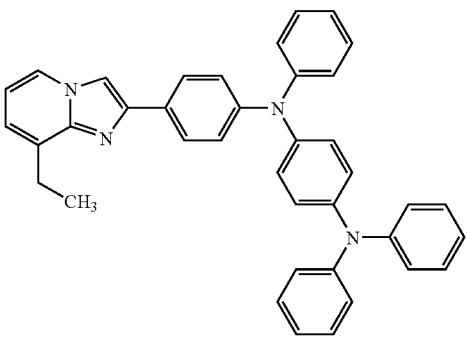
(116)
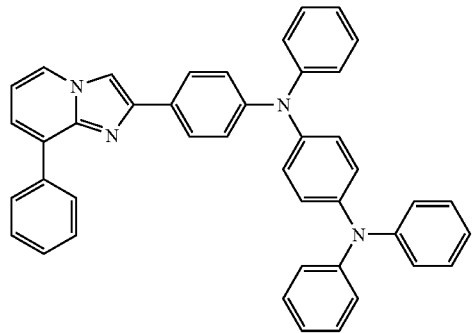
(117)
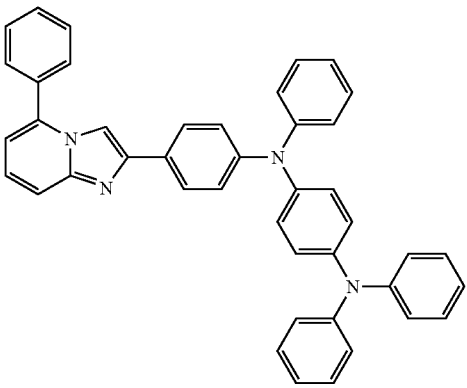

-continued
(118)
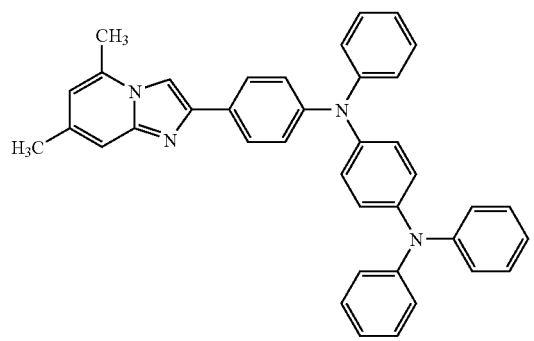
(119)
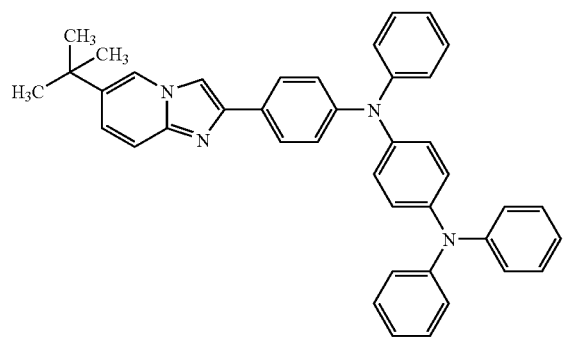
(120)
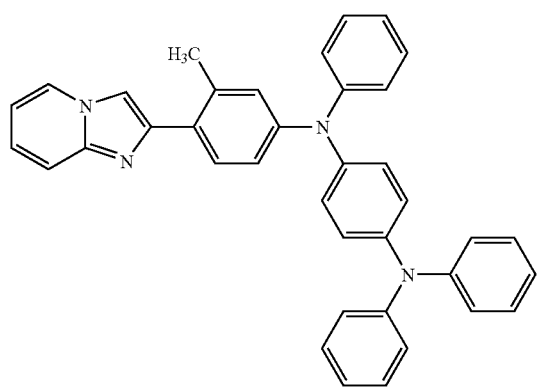
(121)
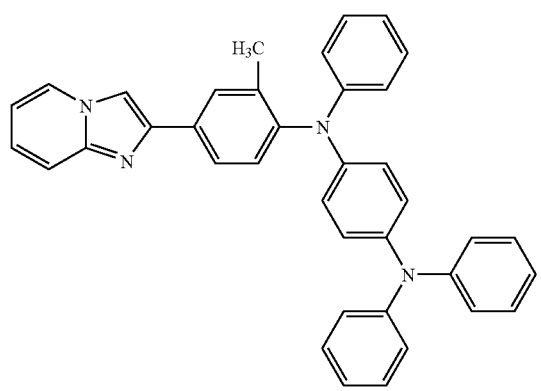
(122)
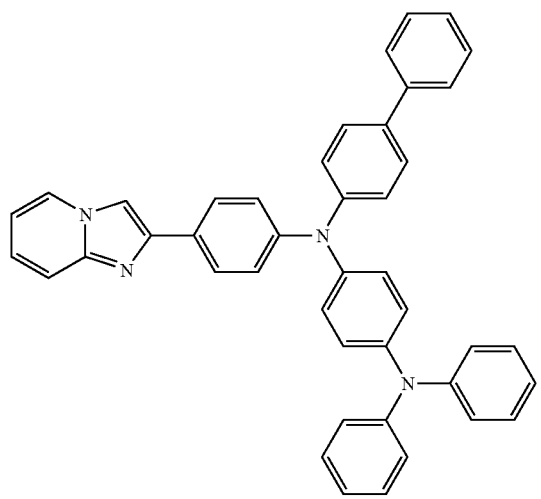
(123)
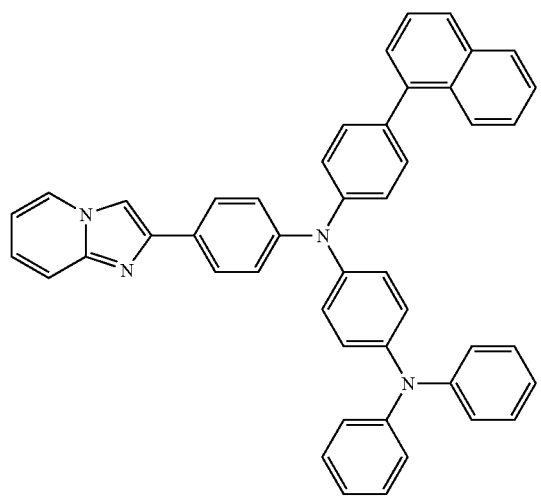

-continued
(124)
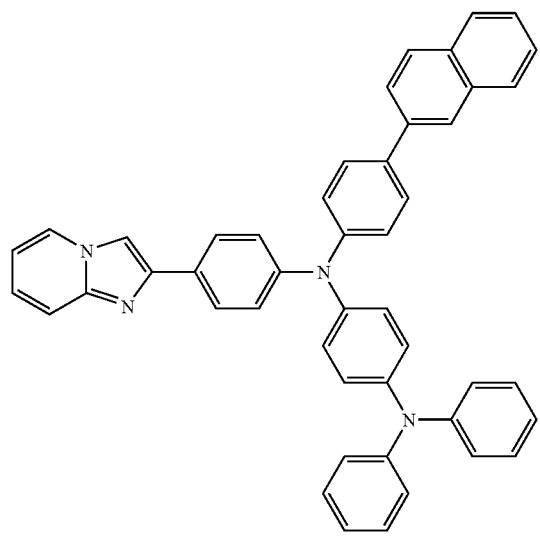
(125)
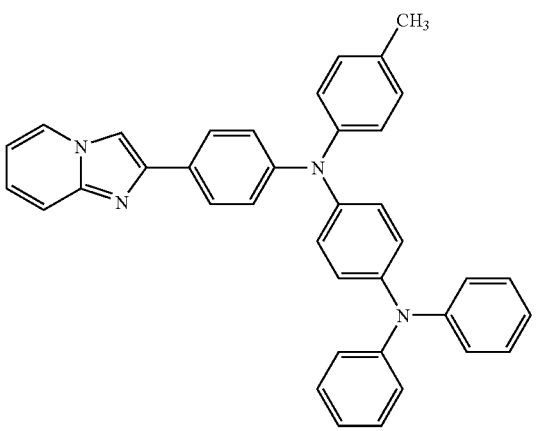
(126)
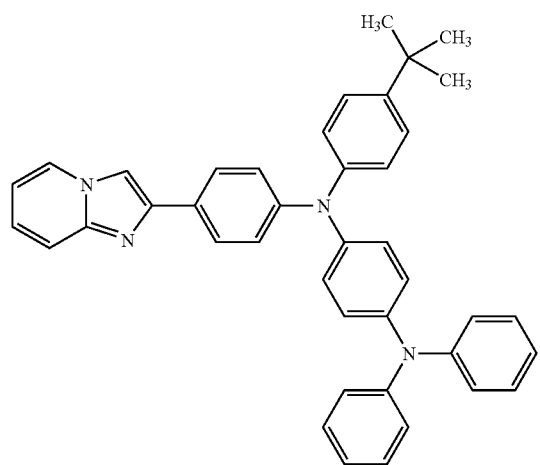
(127)
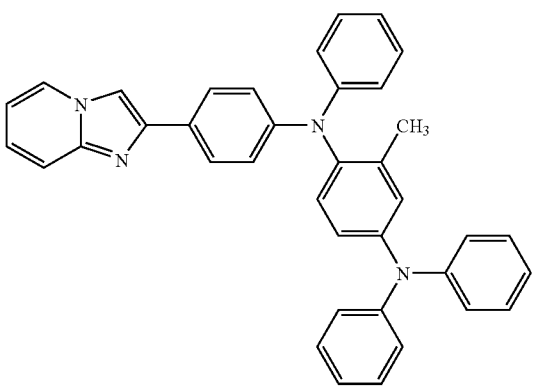
(128)
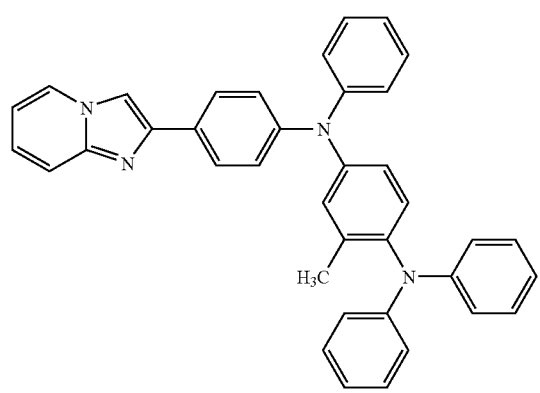
(129)
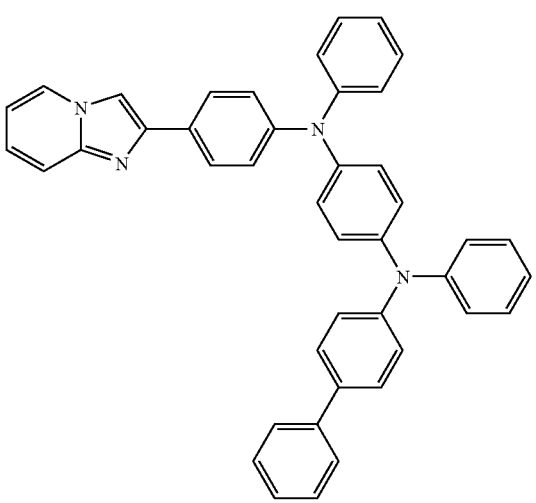

-continued
(130)
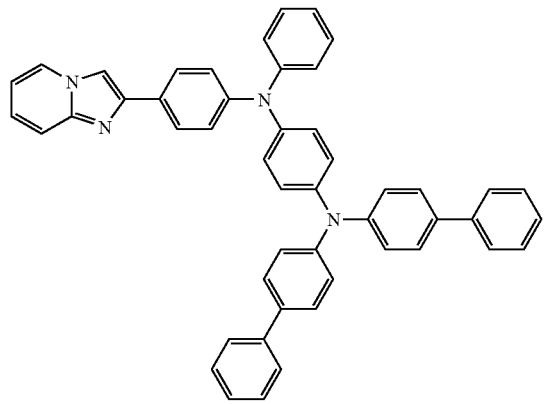
(131)
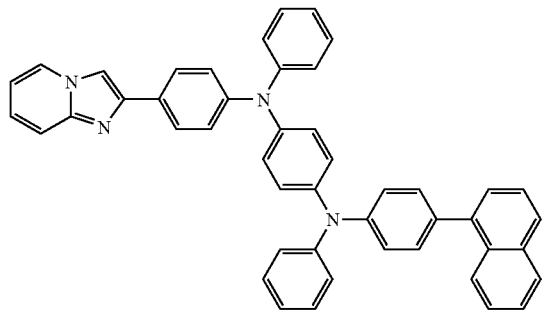
(132)
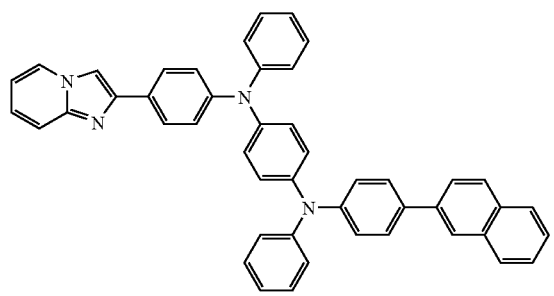
(133)
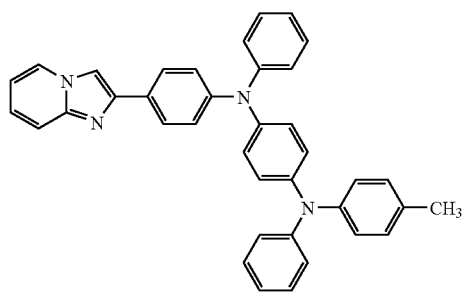
(134)
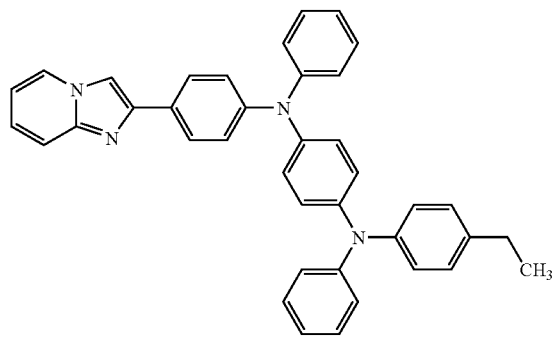
(135)
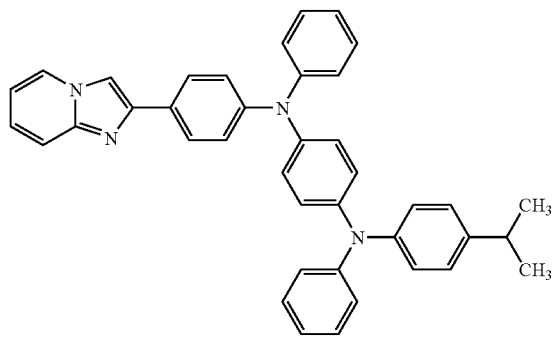
(136)
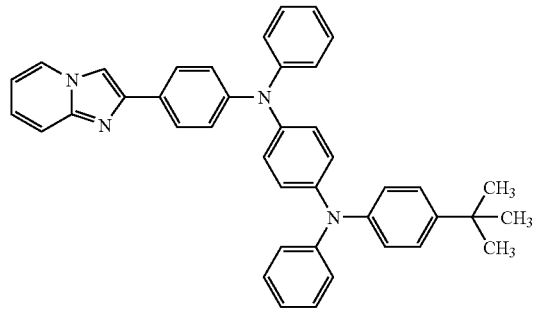
(137)
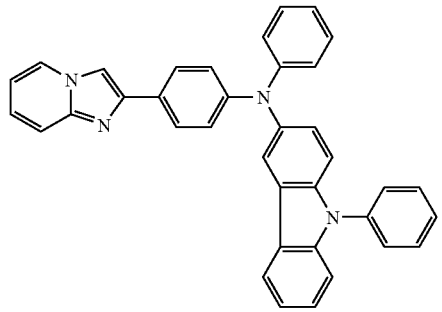

-continued
(138) 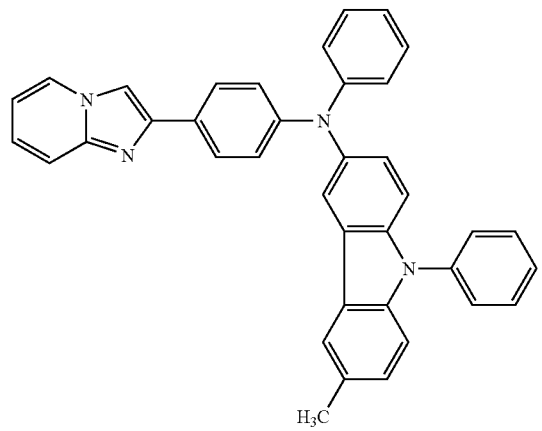
(139) 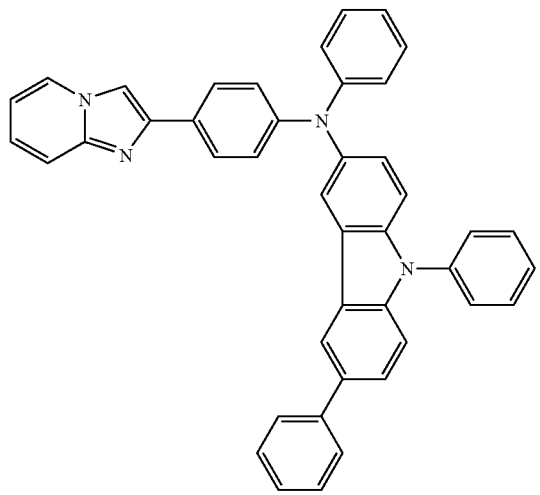
(140) 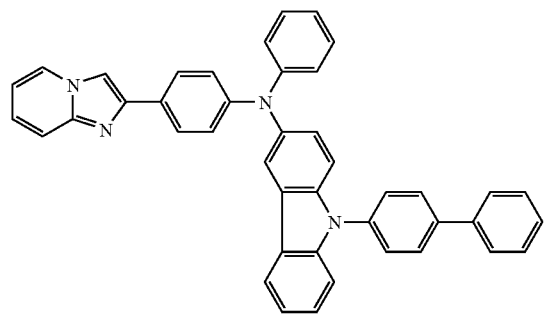
(141) 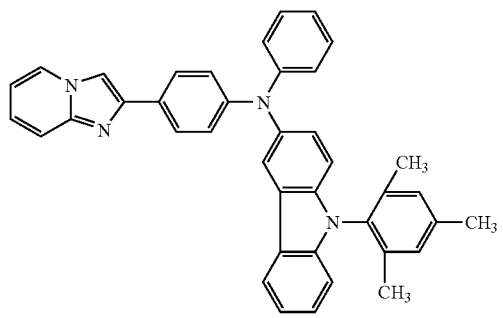
(142) 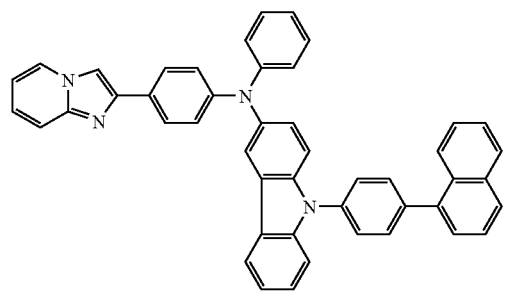
(143) 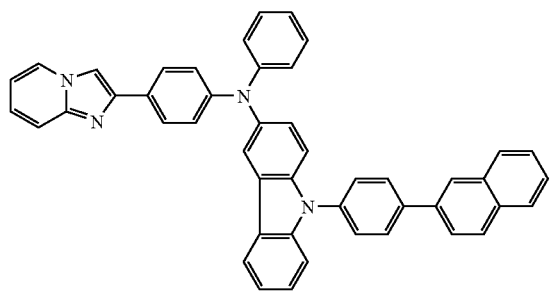
(144) 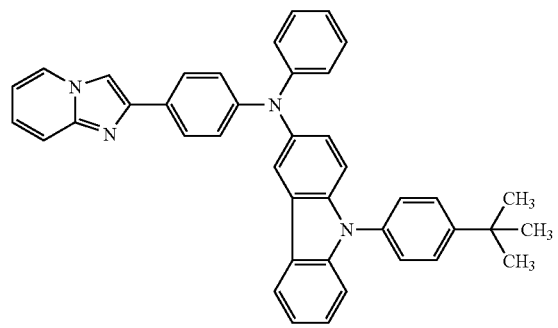
(145) 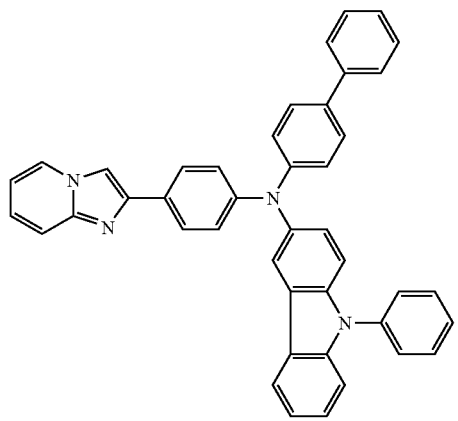

-continued
(146)
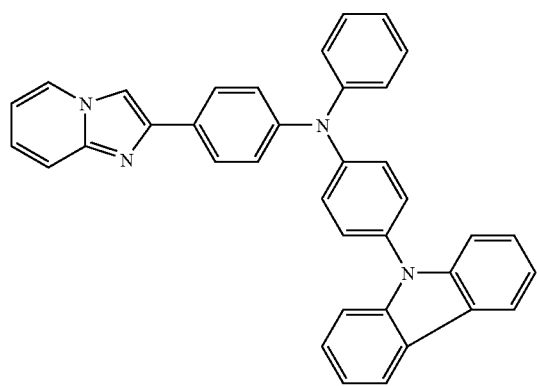
(147)
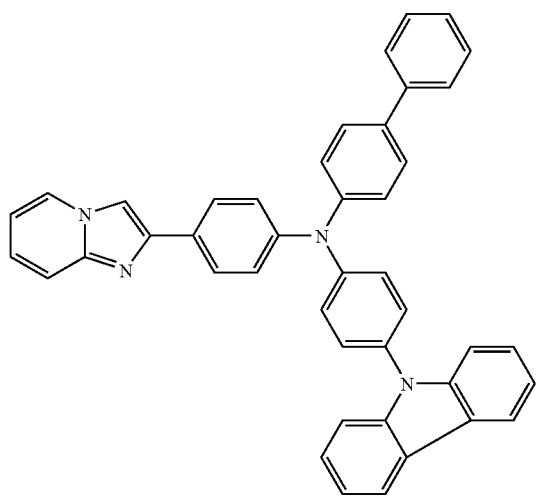
(148)
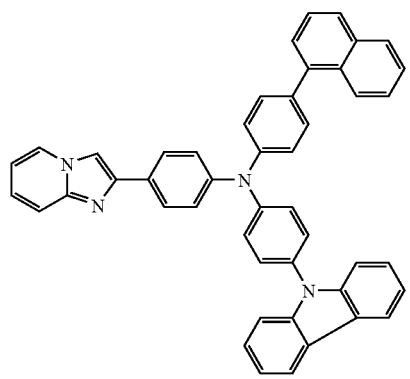
(149)
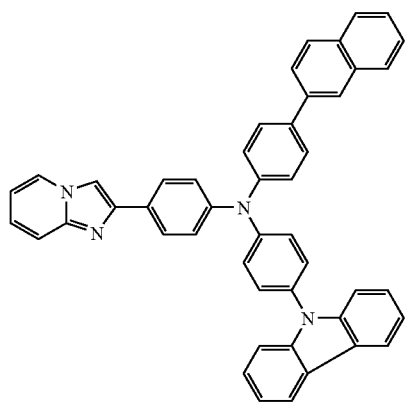
(150)
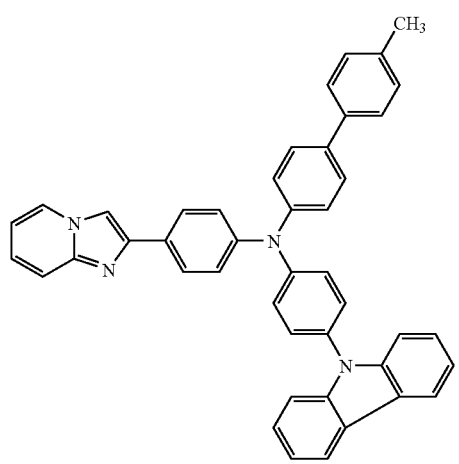
(151)
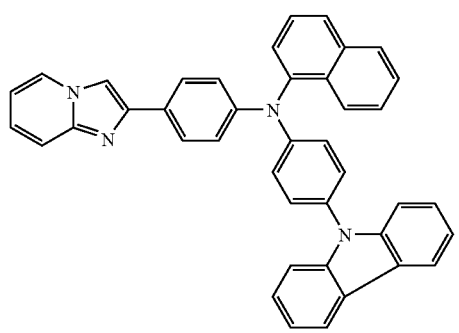

-continued
(152)
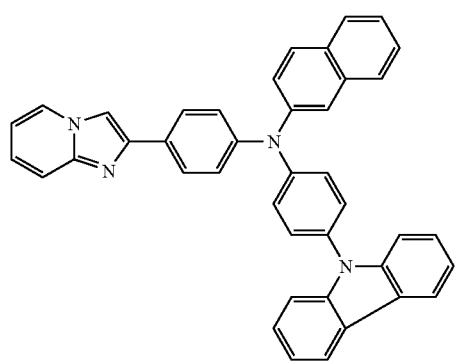
(153)
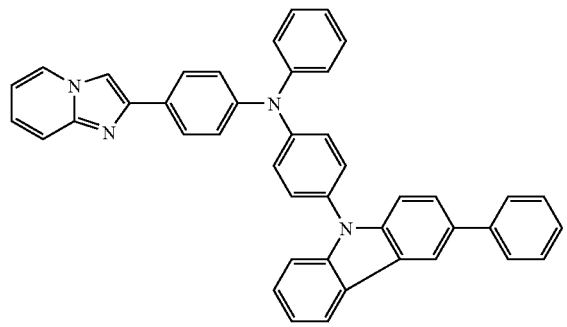
(154)
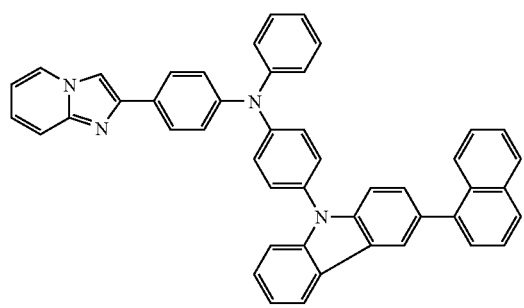
(155)
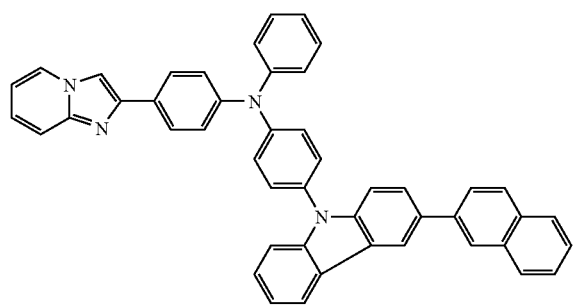
(156)
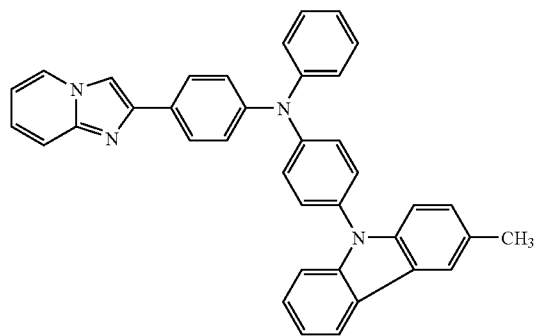
(157)
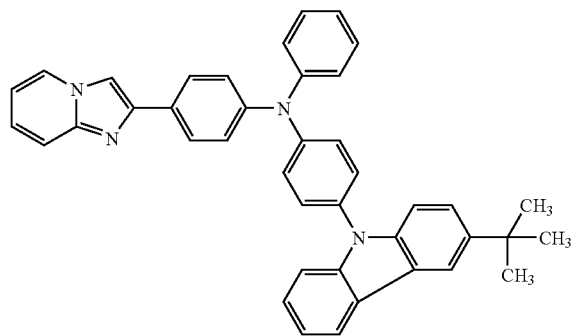
(158)
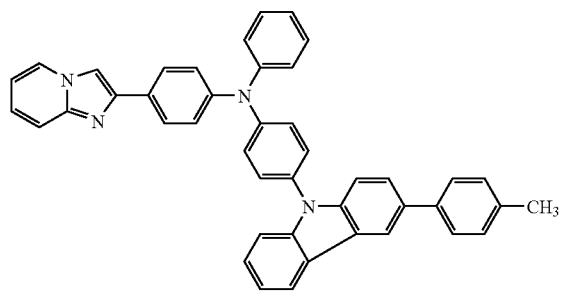
(159)
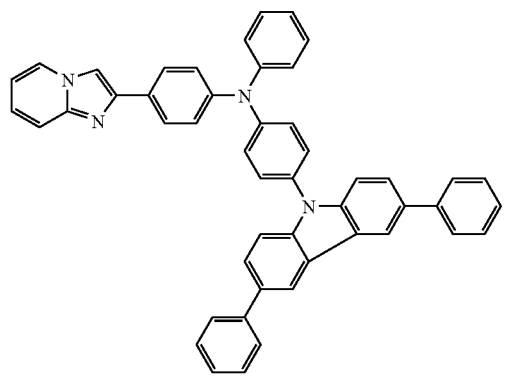

-continued
(160)
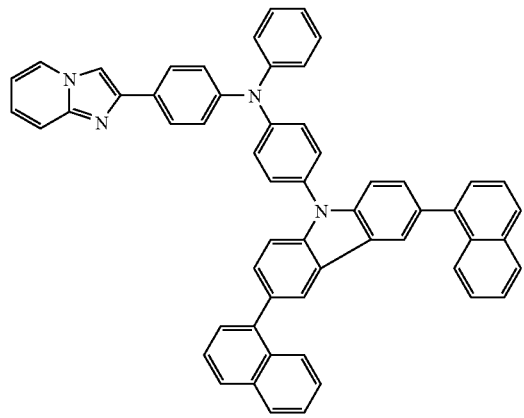
(161)
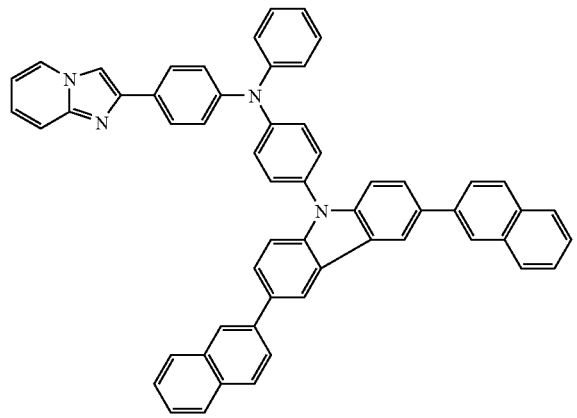
(162)
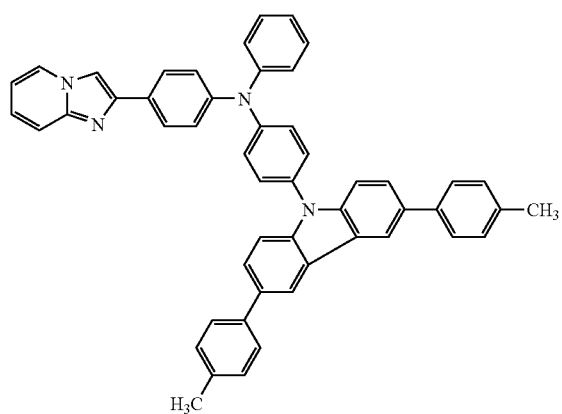
(163)
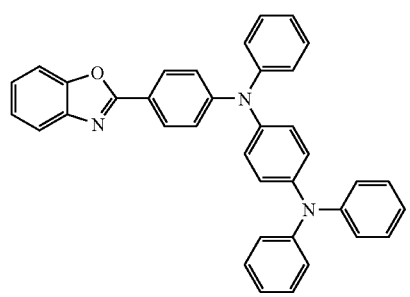
(164)
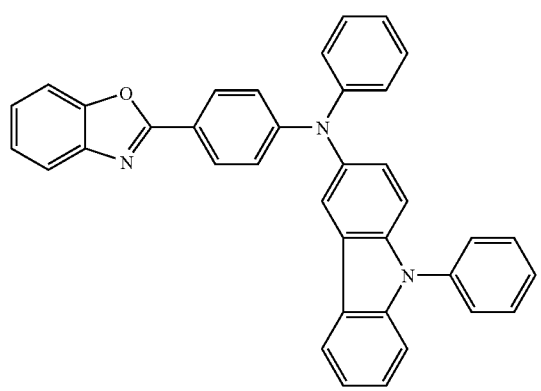
(165)
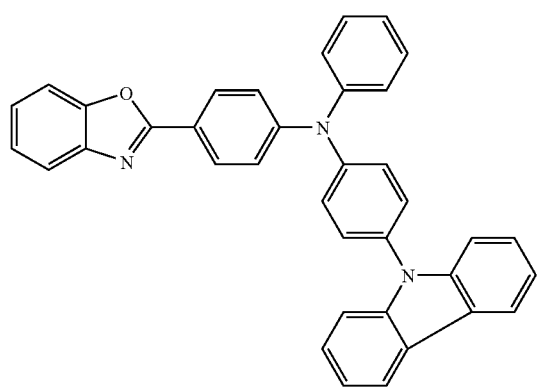
(166)
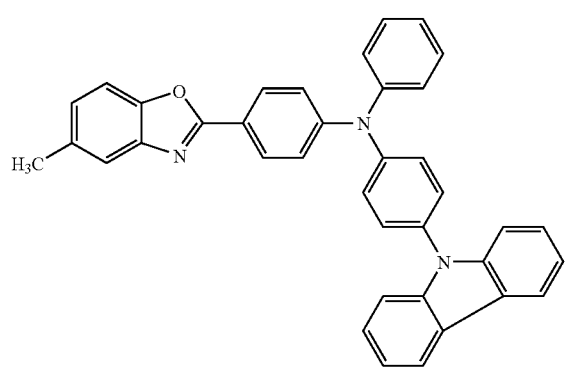
(167)
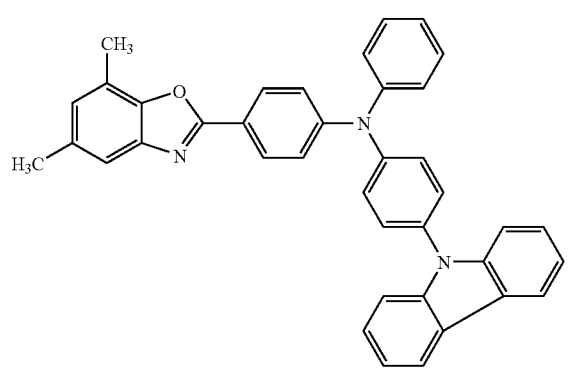

-continued
(168)
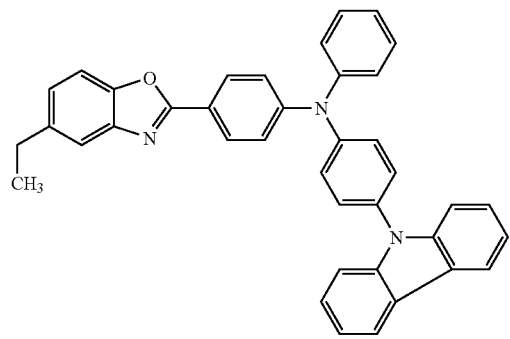
(169)
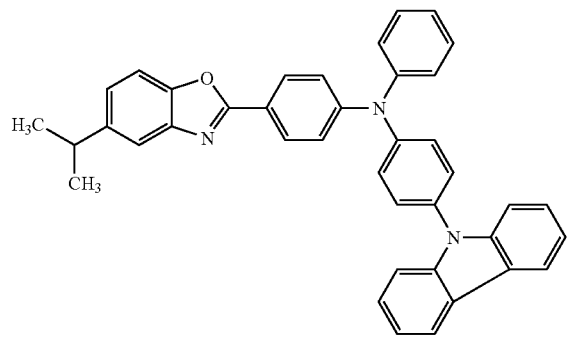
(170)
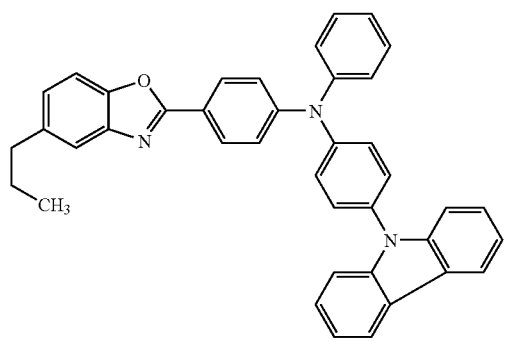
(171)
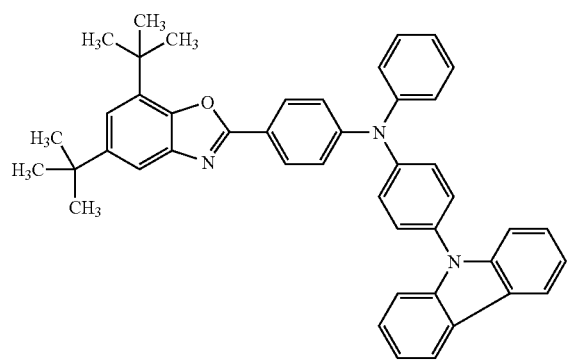
(172)
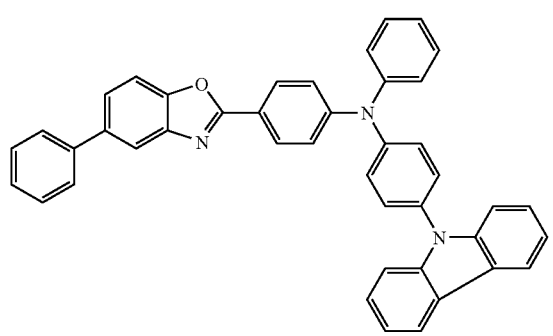
(173)
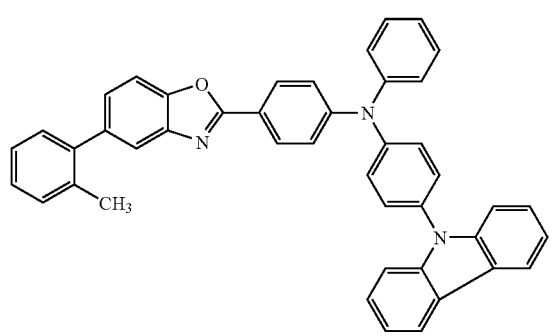
(174)
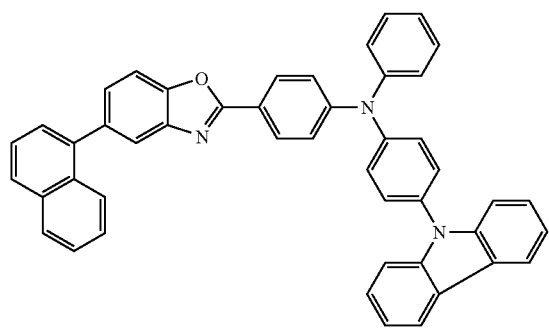
(175)
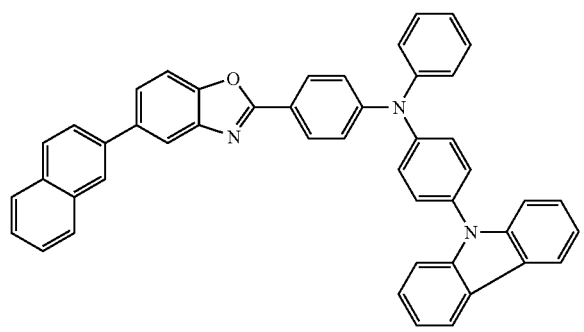

-continued
(176)
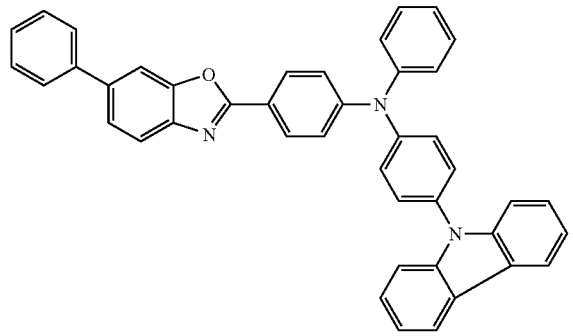
(177)
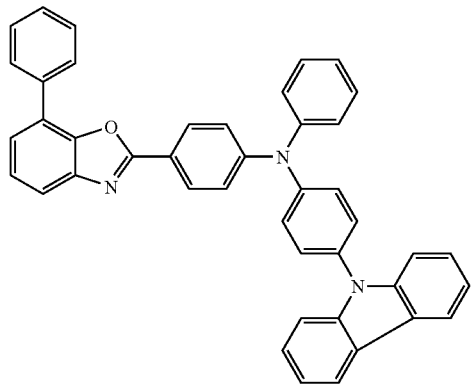
(178)
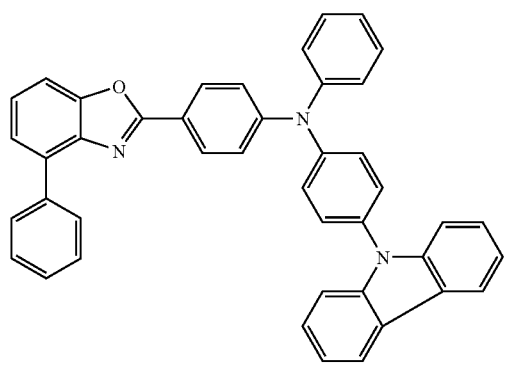
(179)
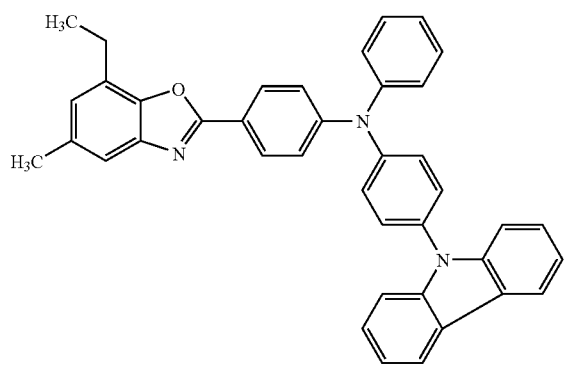
(180)
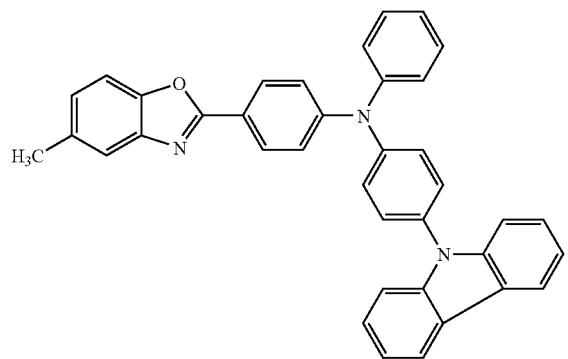
(181)
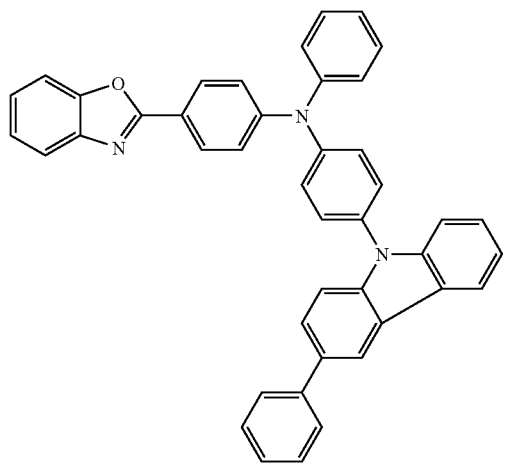

-continued
(182)
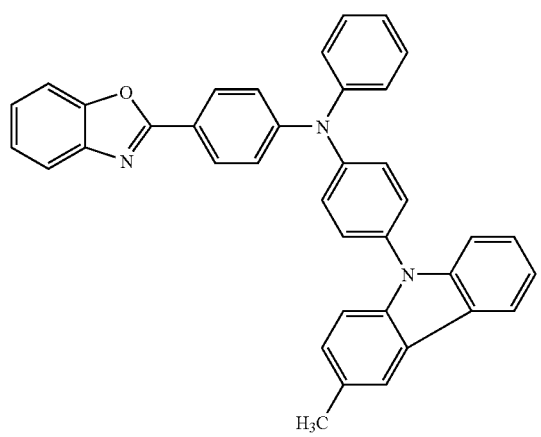
(183)
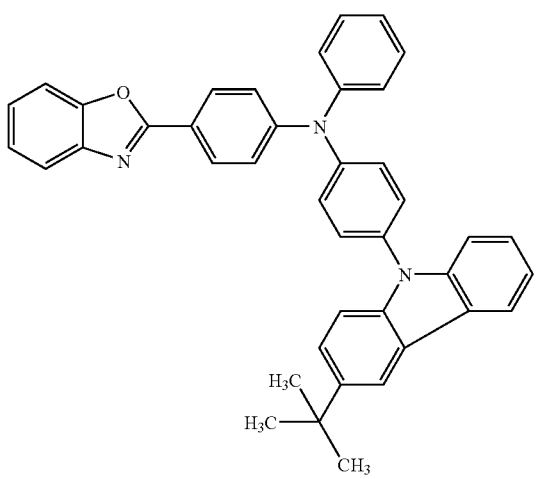
(184)
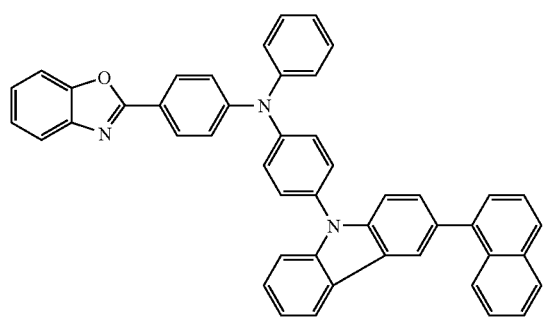
(185)
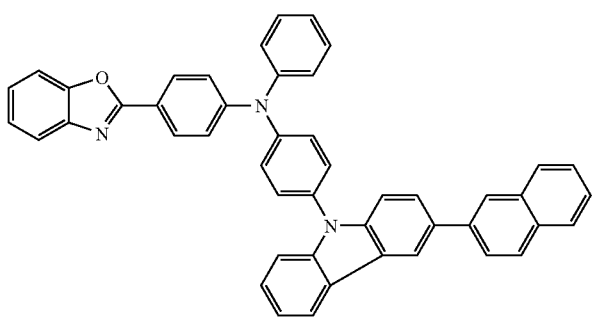
(186)
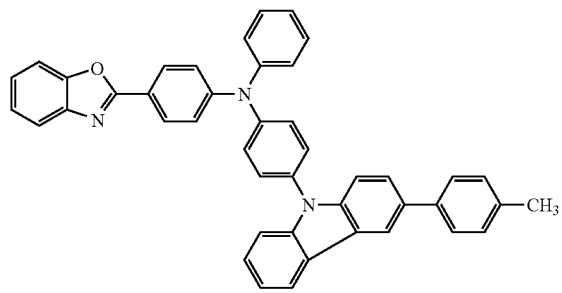
(187)
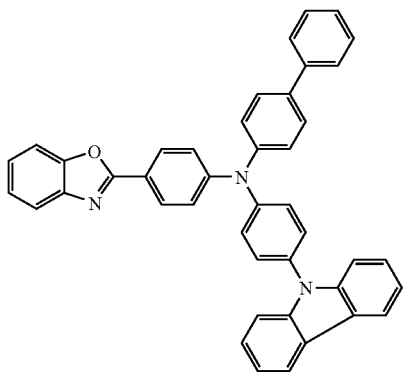
(188)
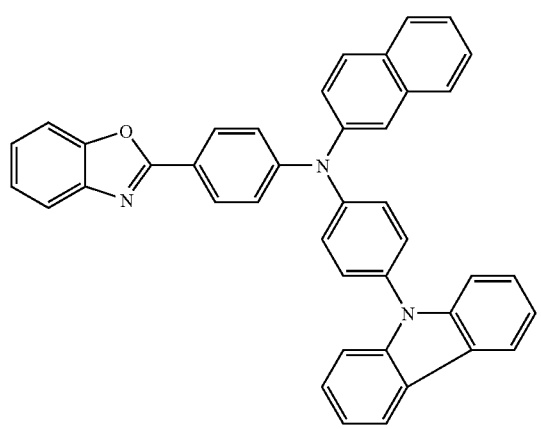
(189)

-continued
(190) 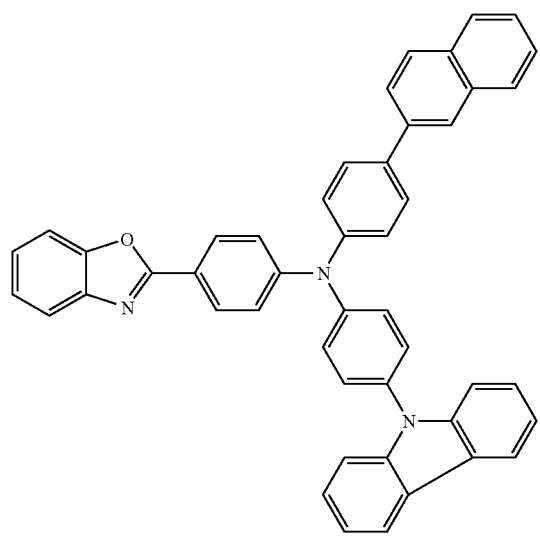
(191) 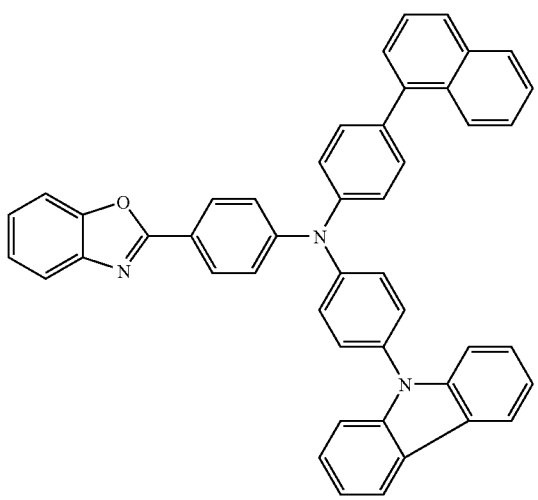
(192) 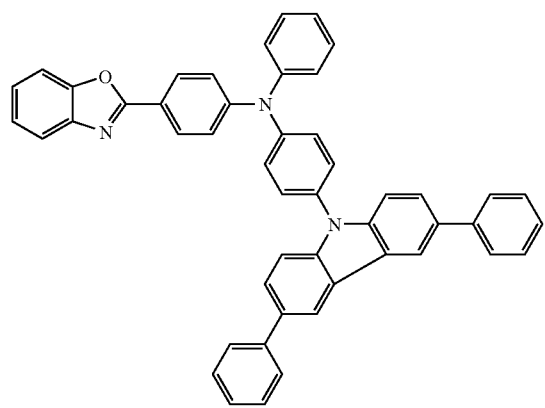
(193) 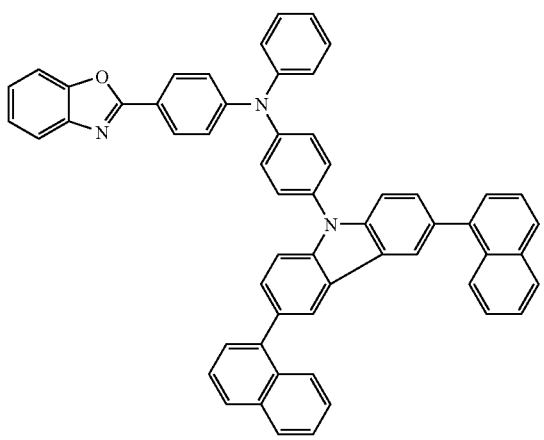
(194) 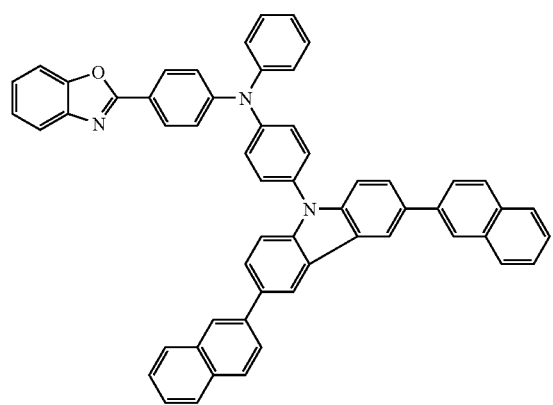
(195) 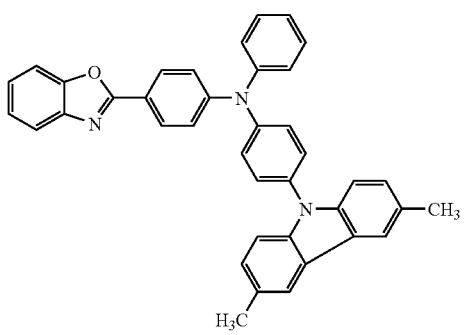

-continued
(196)
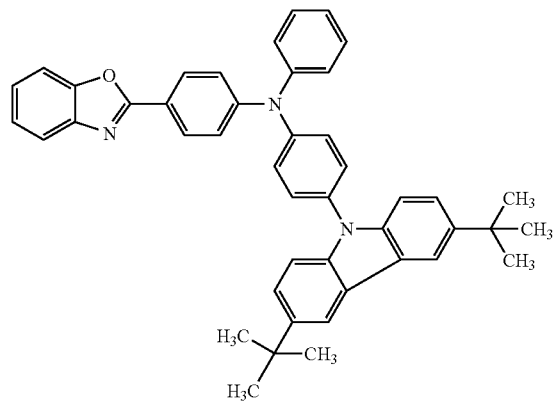
(197)
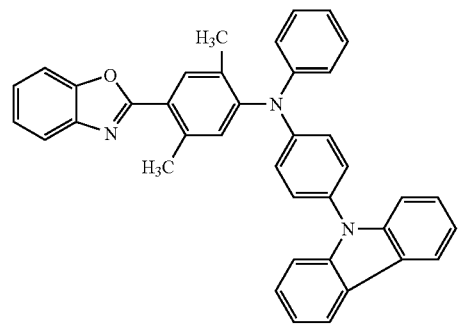
(198)
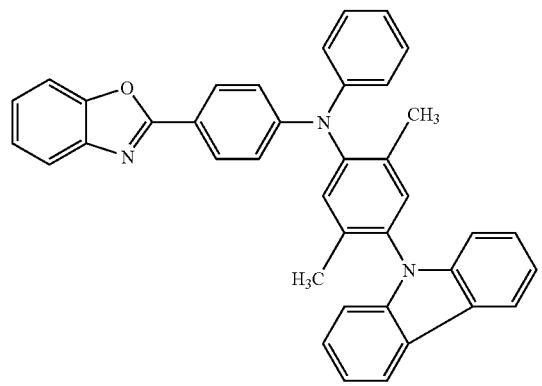
(199)
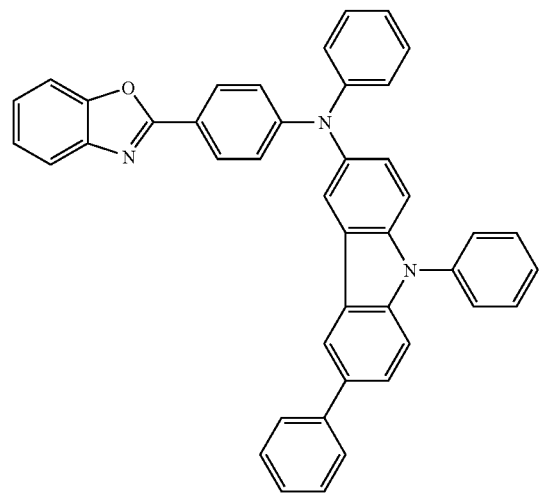
(200)
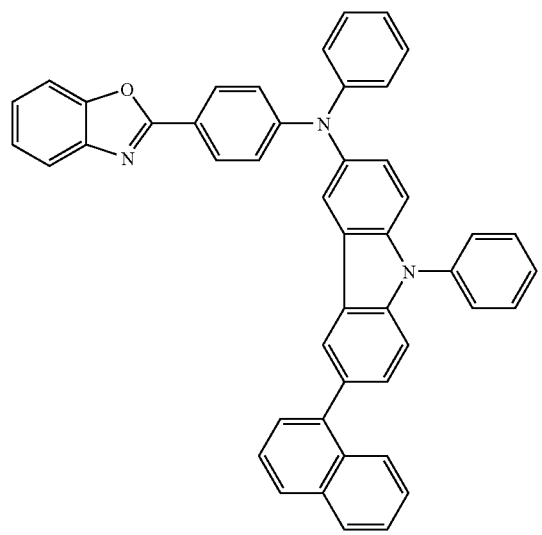
(201)
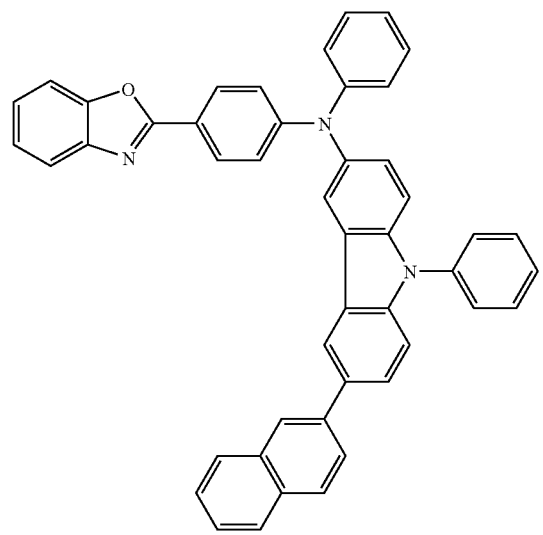

-continued
(202) 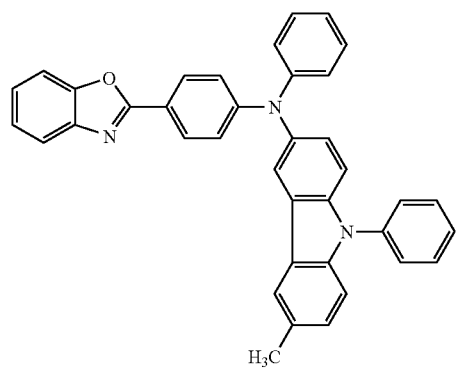
(203) 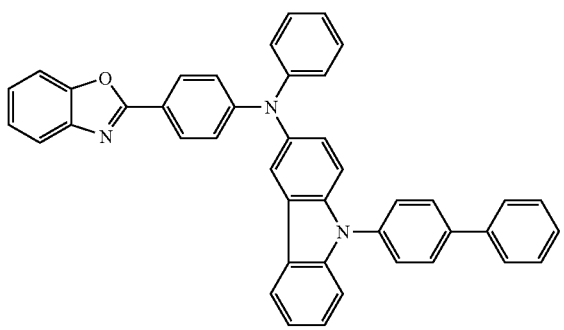
(204) 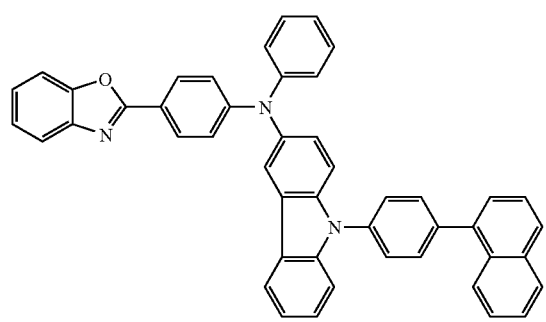
(205) 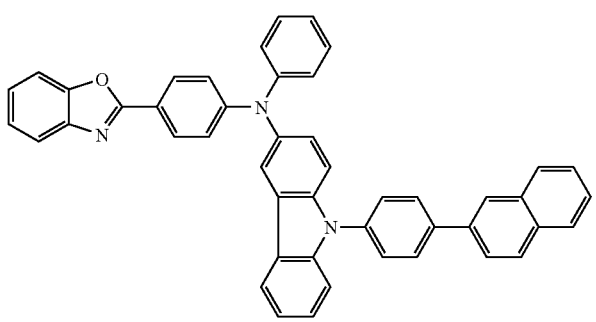
(206) 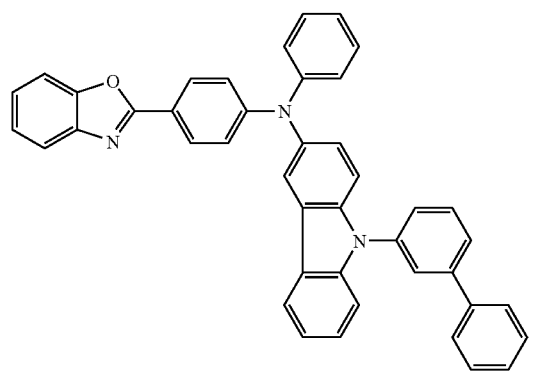
(207) 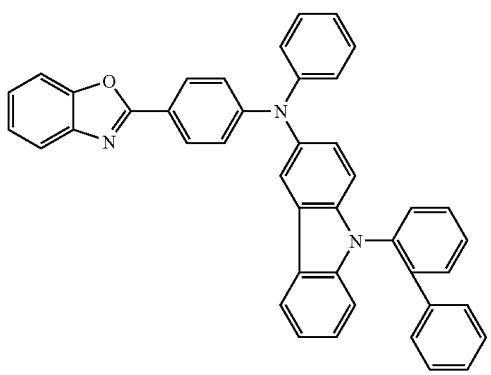
(208) 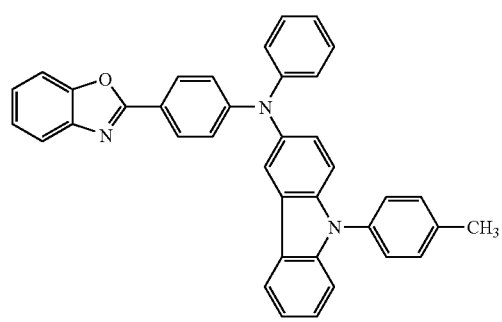
(209) 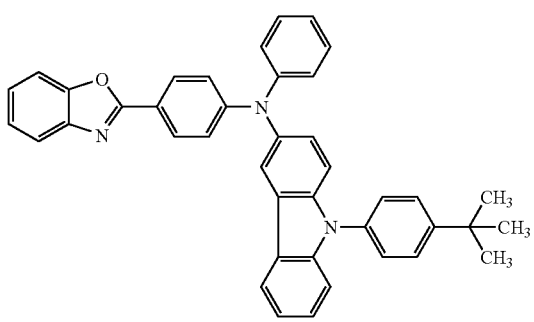

-continued
(210)
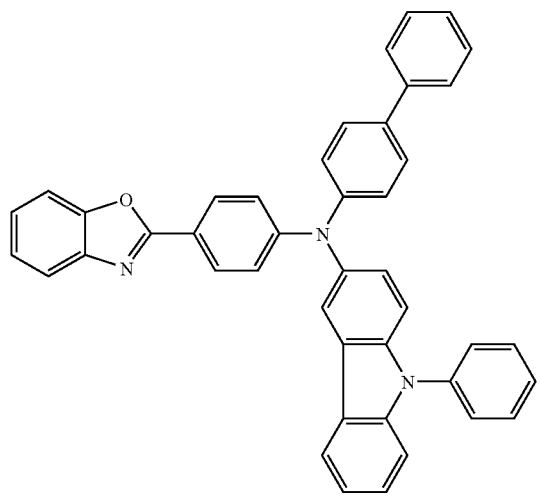
(211)
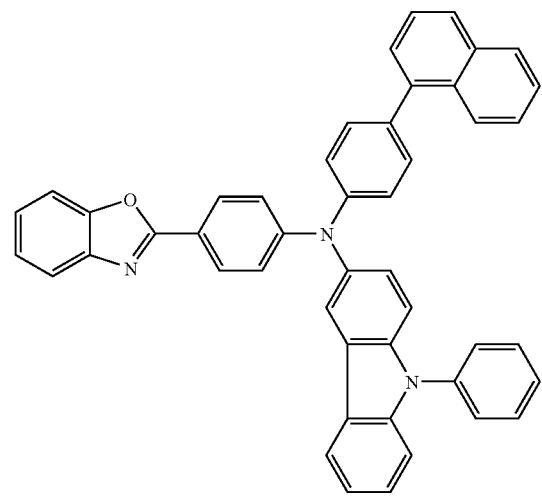
(212)
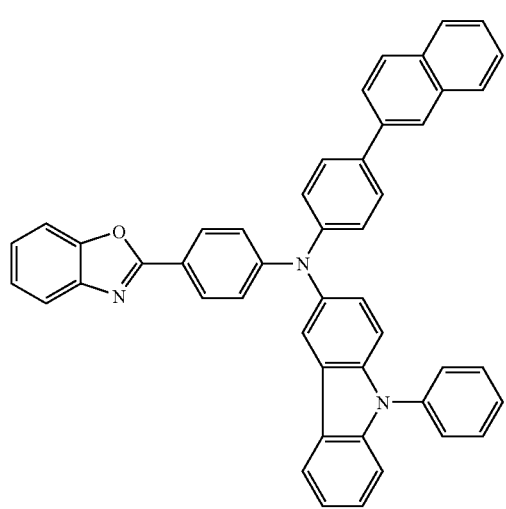
(213)
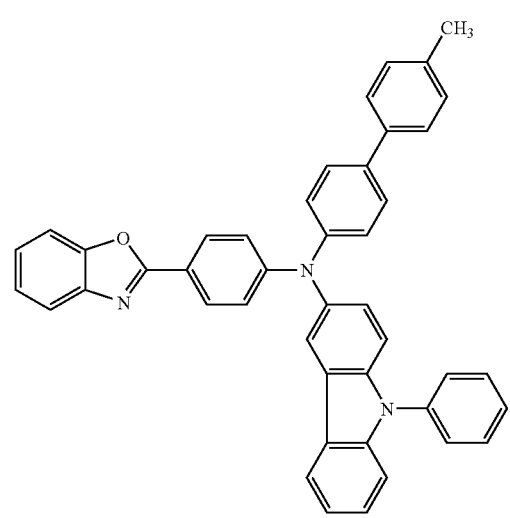
(214)
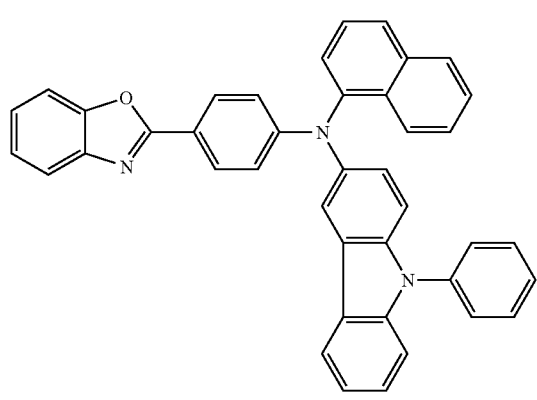
(215)
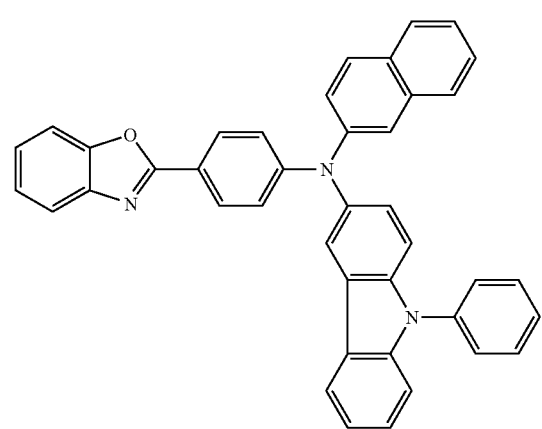

-continued
(216)
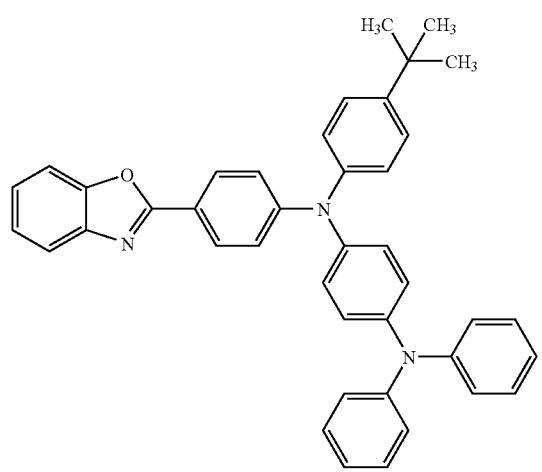
(217)
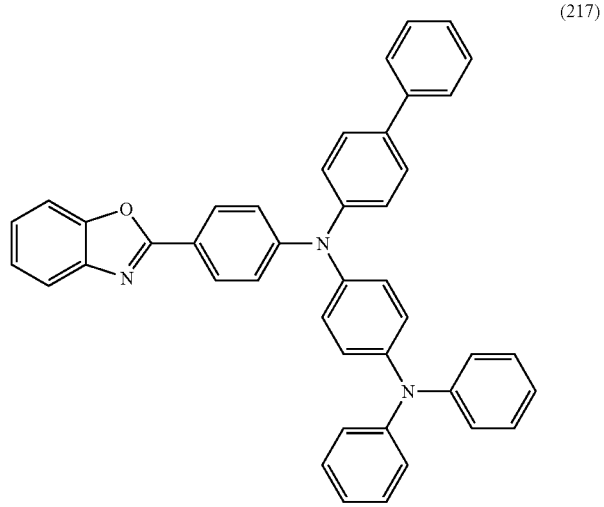
(218)
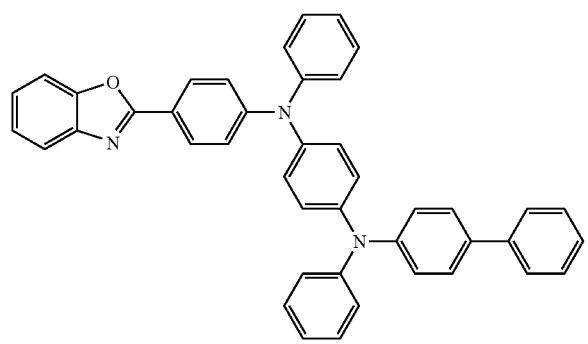
(219)
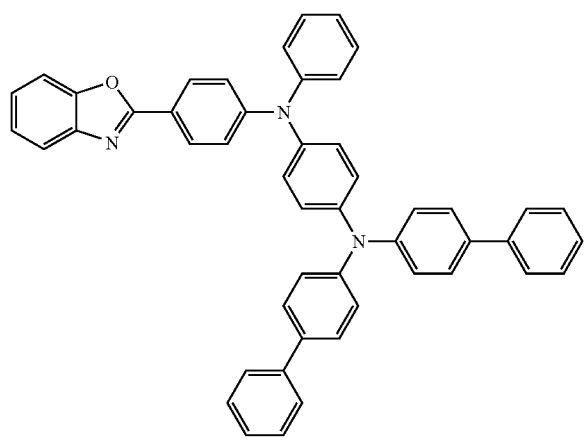
(220)
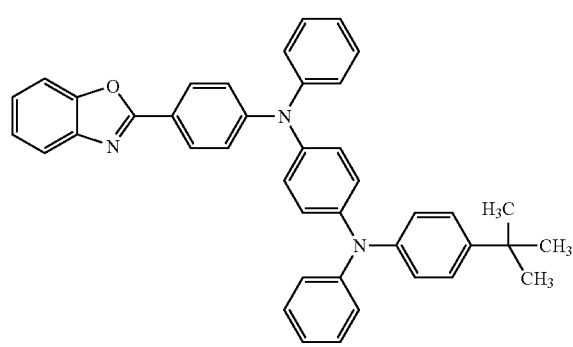
(221)
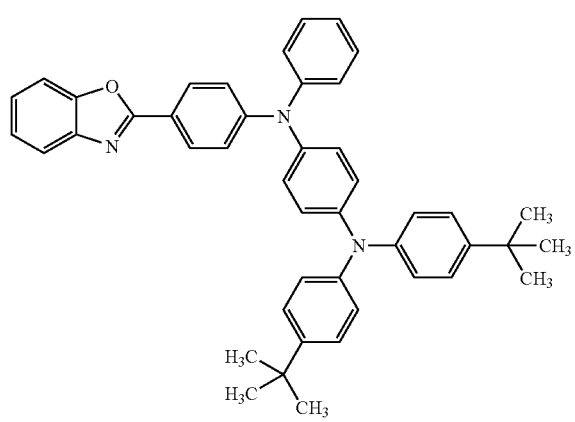

-continued
(222) 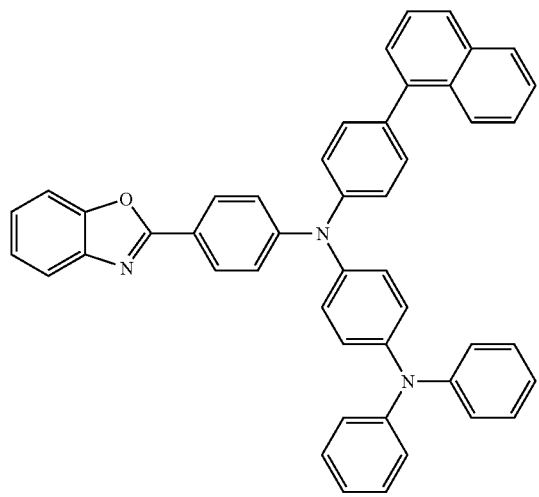
(223) 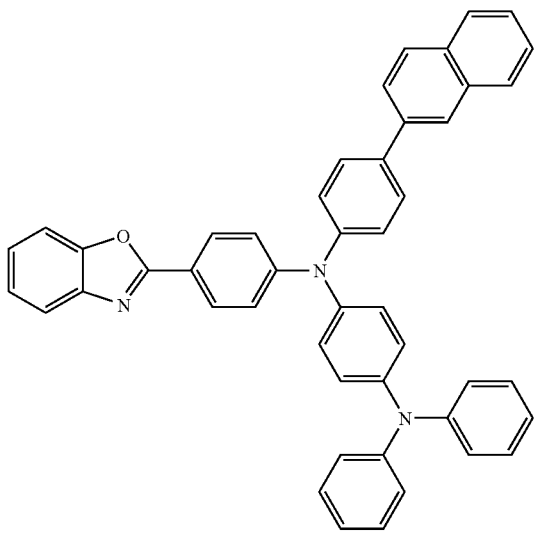
(224) 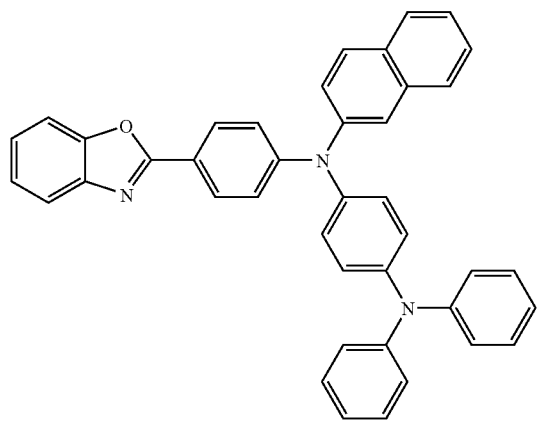
(225) 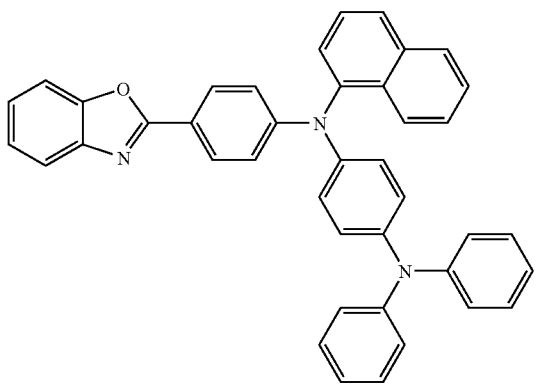
(226) 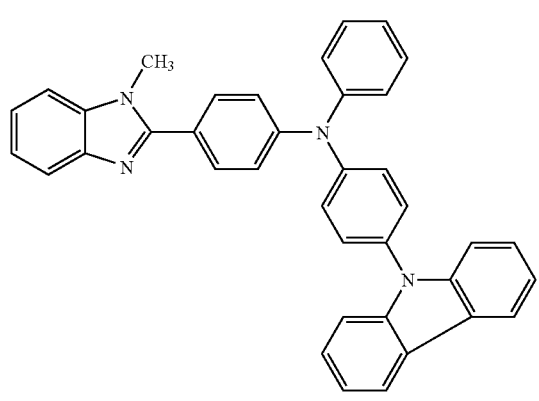
(227) 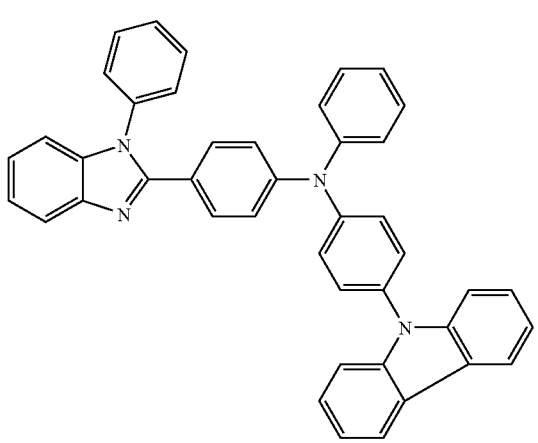

-continued
(228)
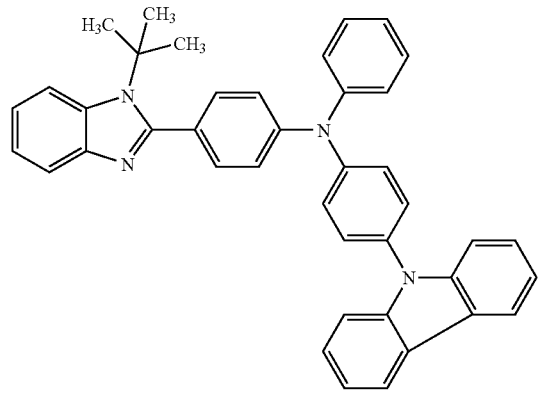
(229)
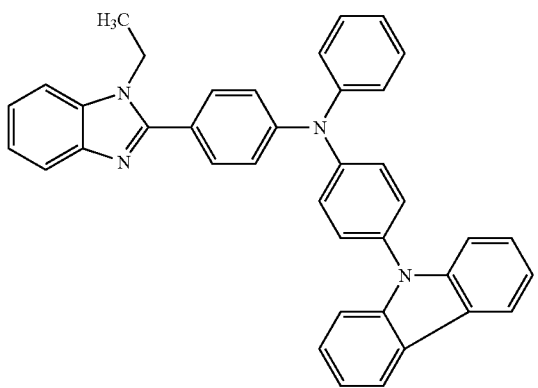
(230)
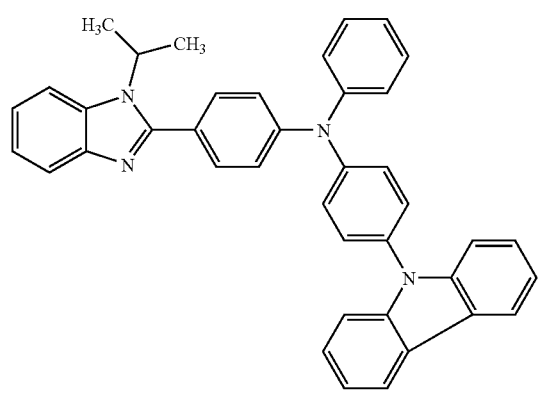
(231)
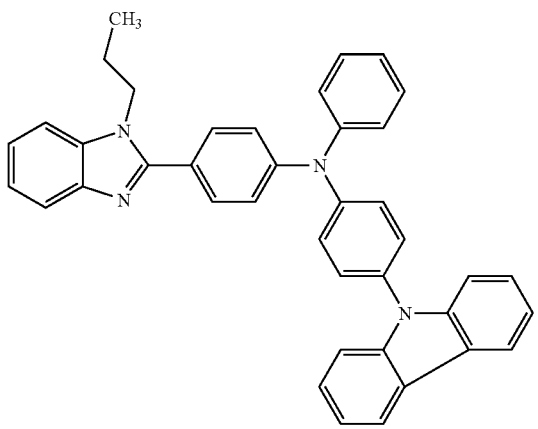
(232)
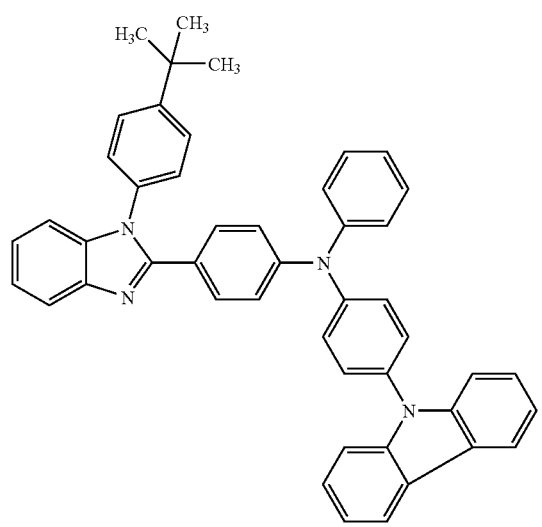
(233)
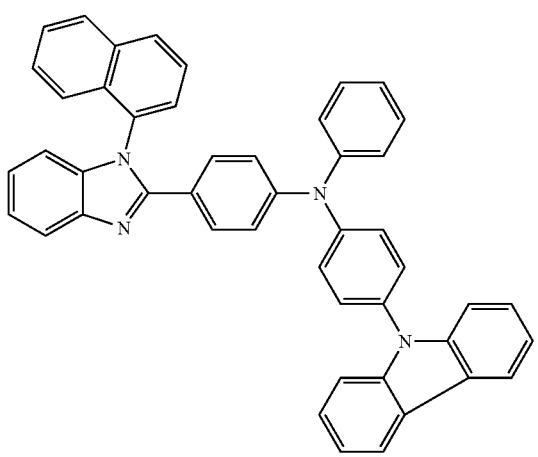

-continued
(234)
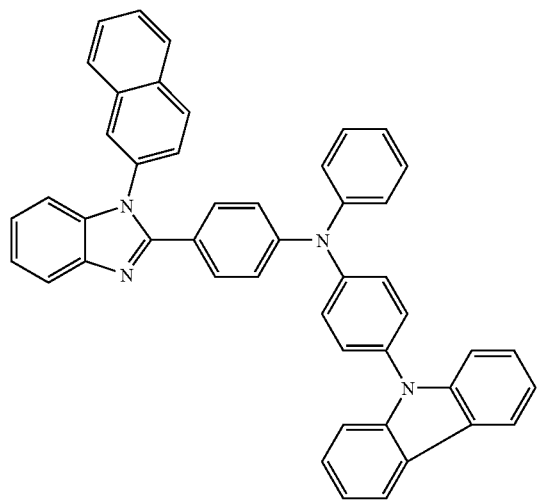
(235)
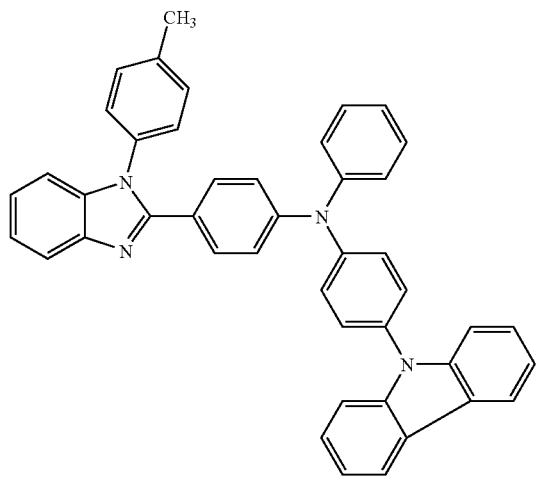
(236)
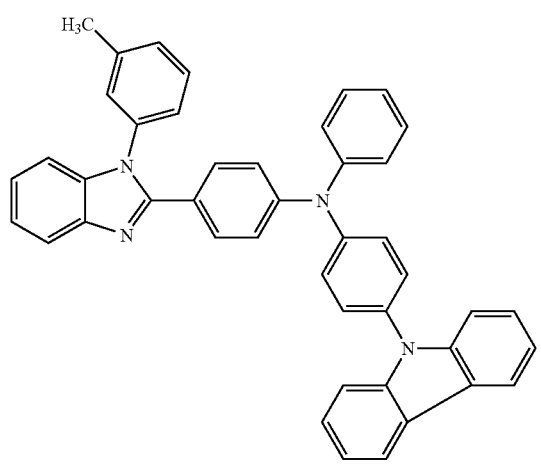
(237)
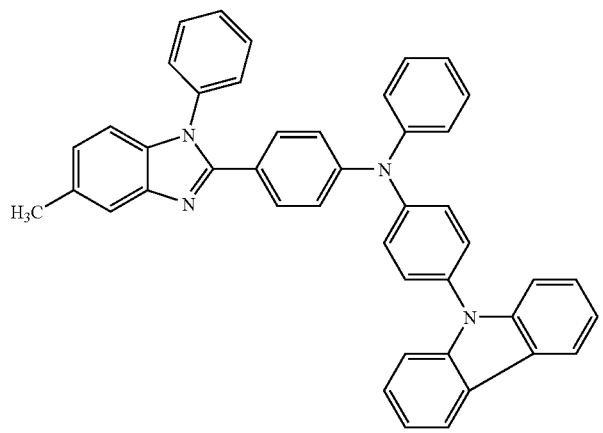
(238)
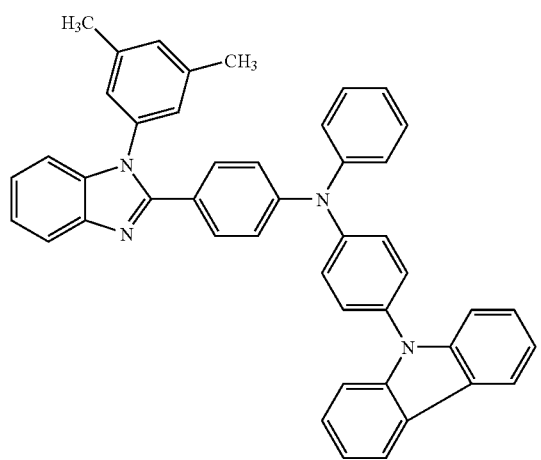
(239)
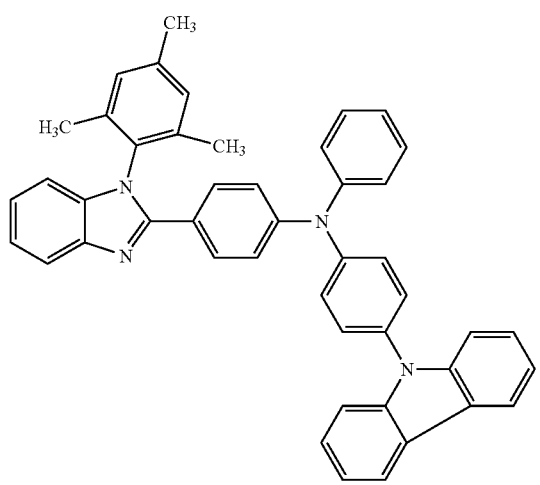

-continued
(240)
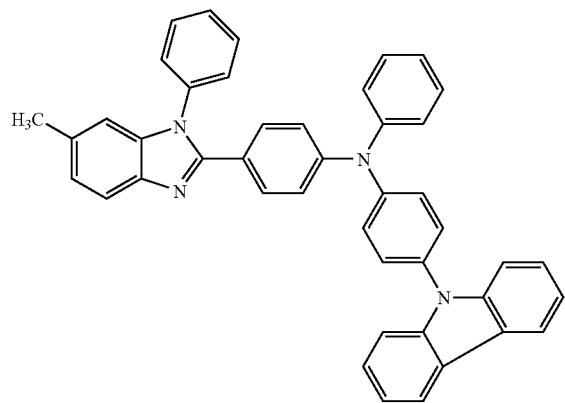
(241)
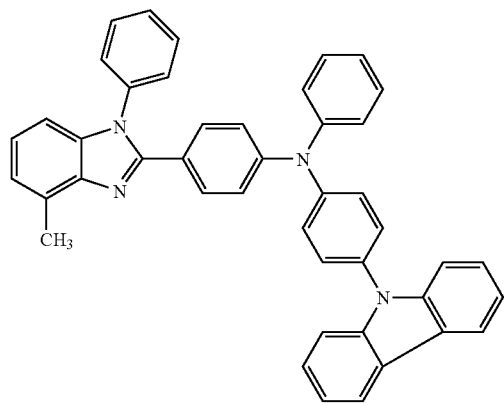
(242)
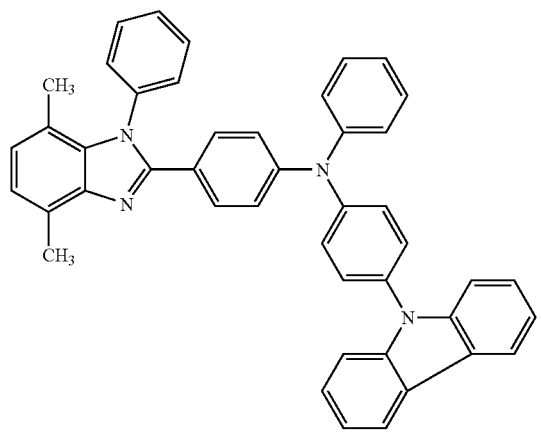
(243)
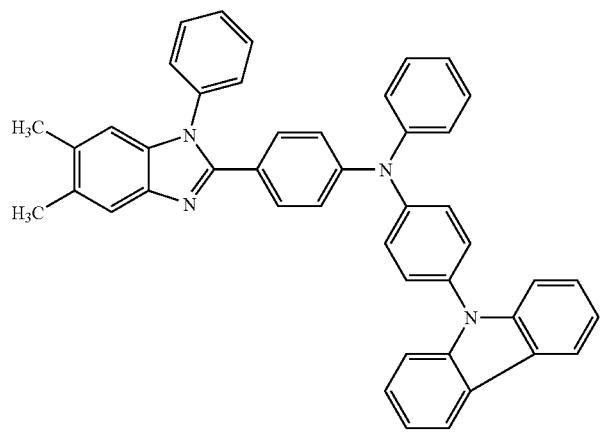
(244)
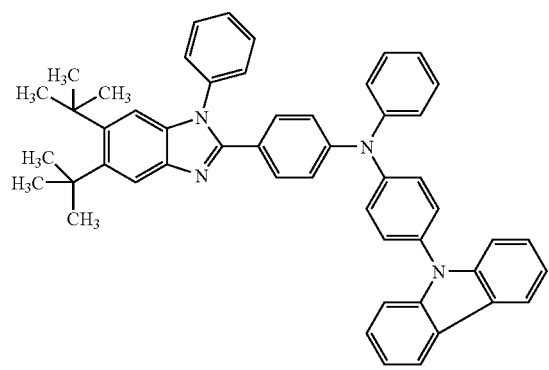
(245)
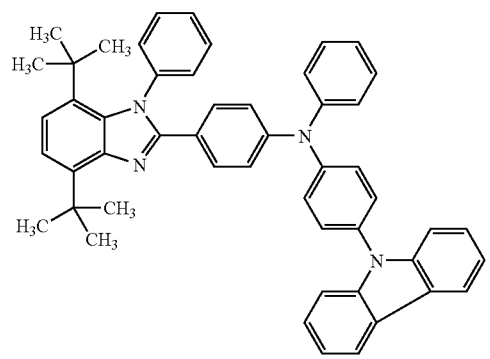

-continued
(246)
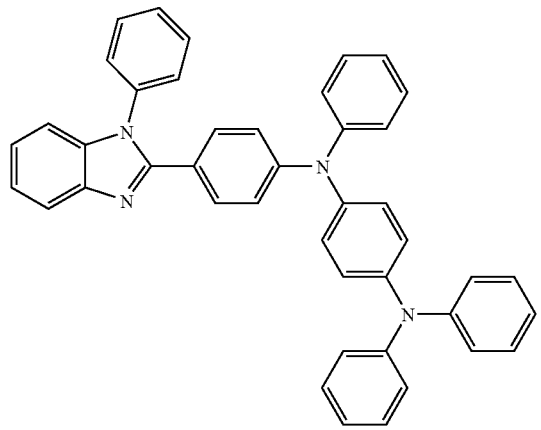
(247)
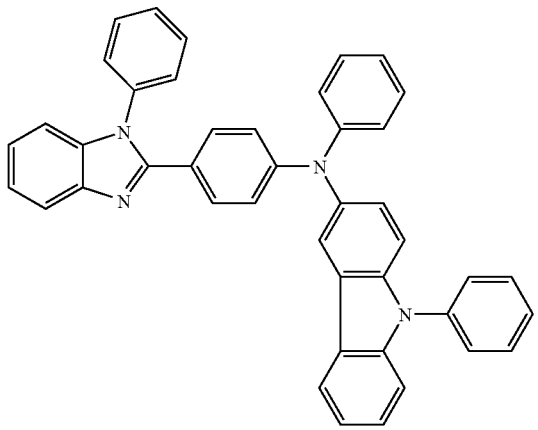
(248)
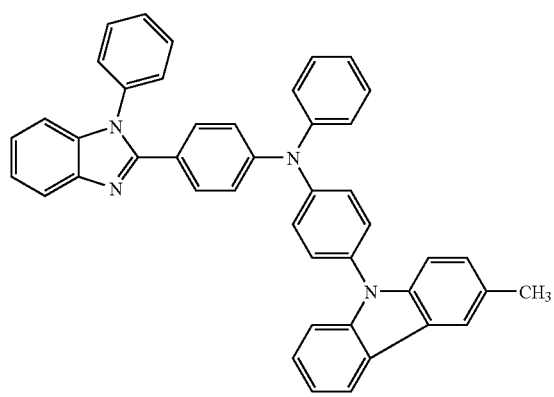
(249)
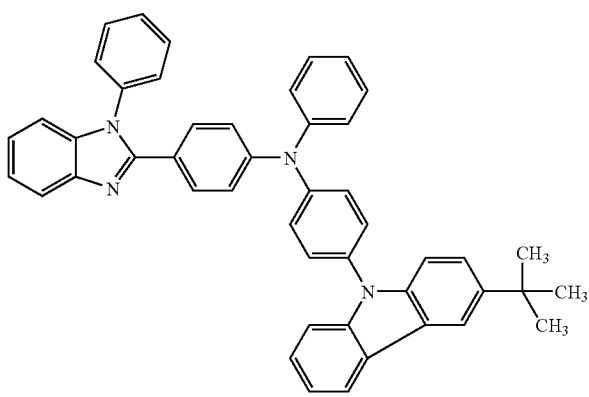
(250)
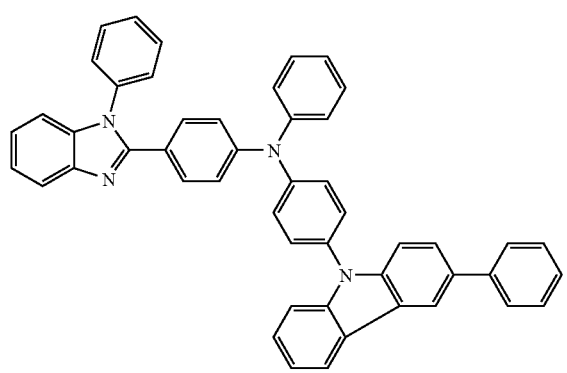
(251)
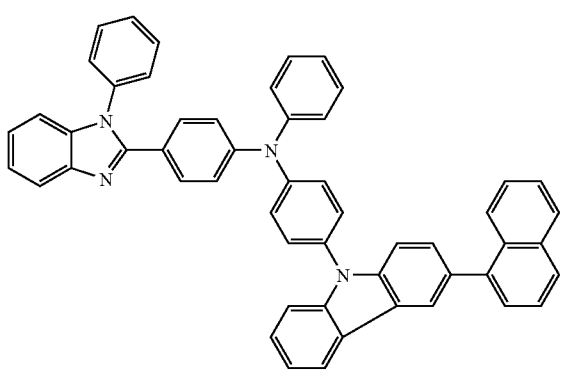
(252)
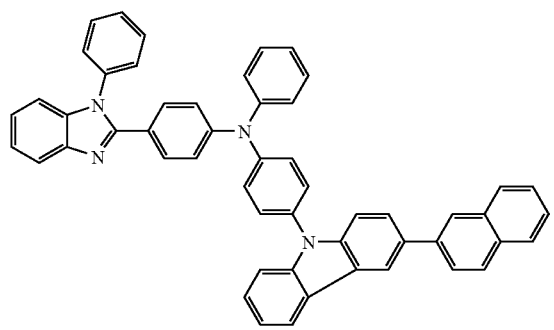
(253)
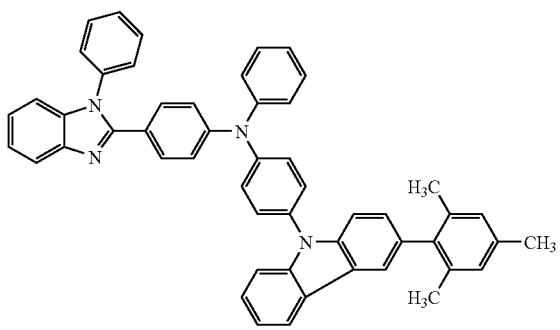

(254)
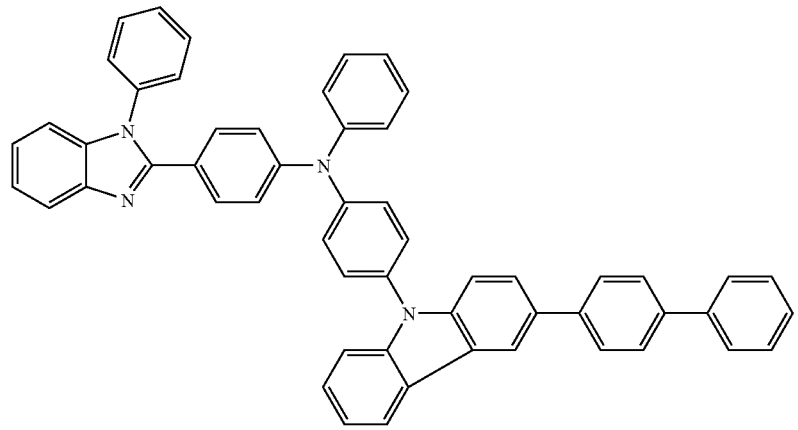
(255)
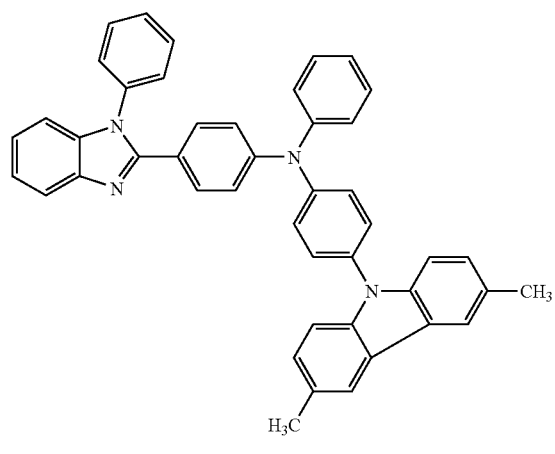
(256)
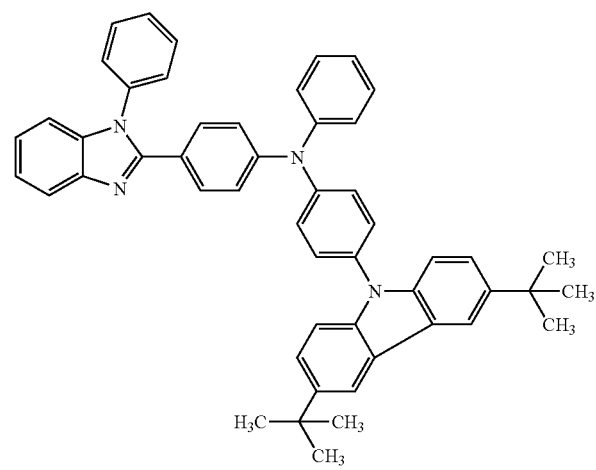
(257)
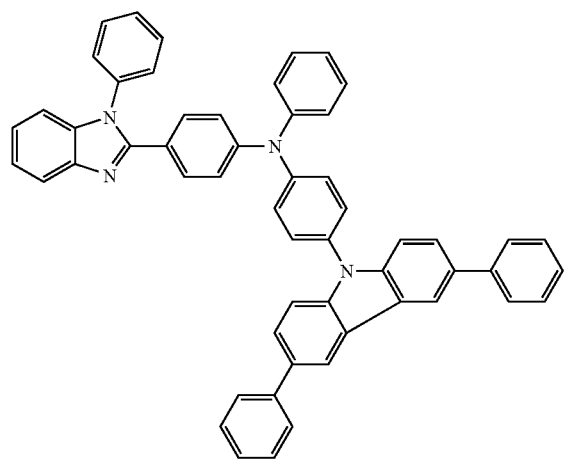
(258)
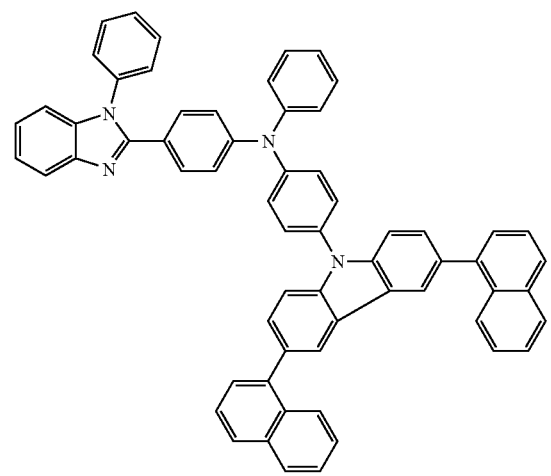

(259)
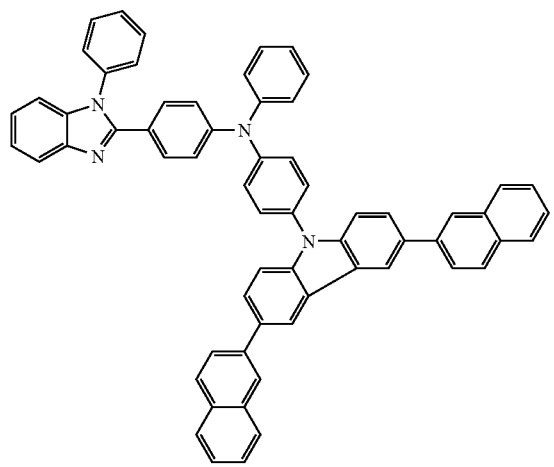
(260)
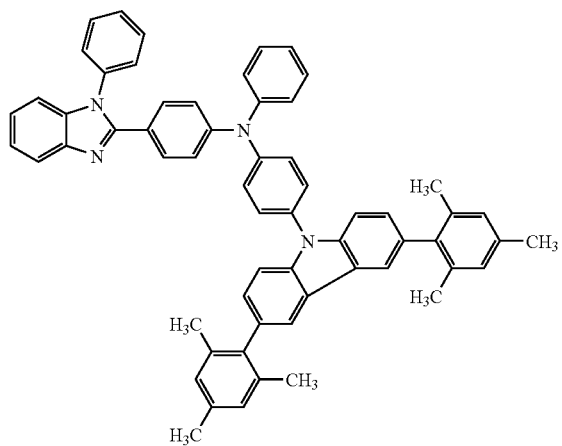
(261)
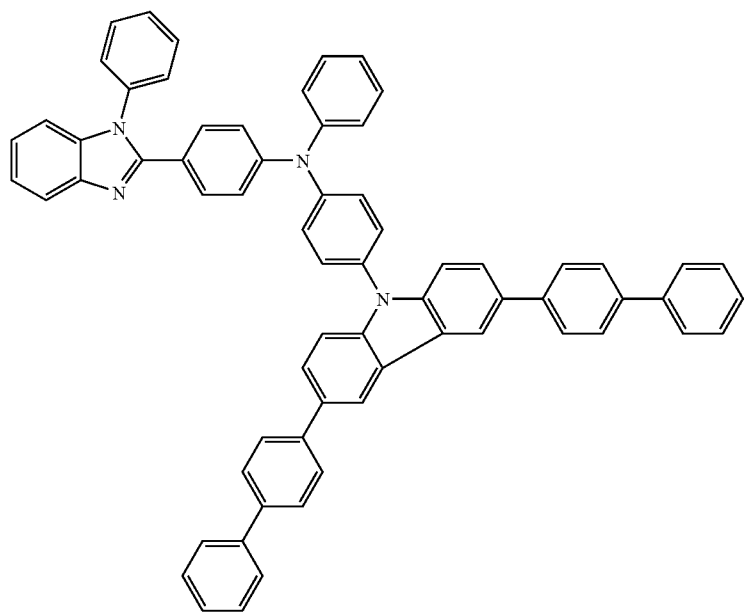
(262)
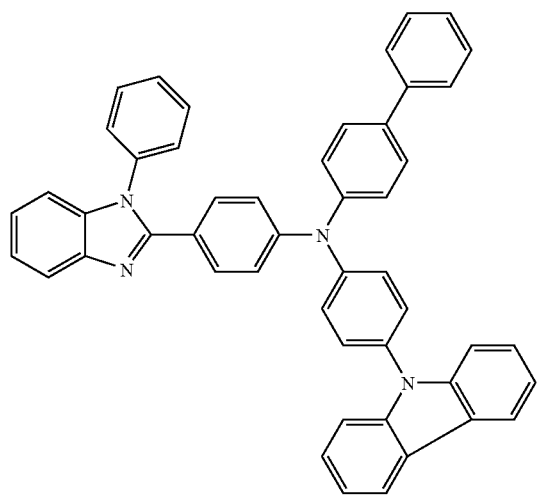
(263)
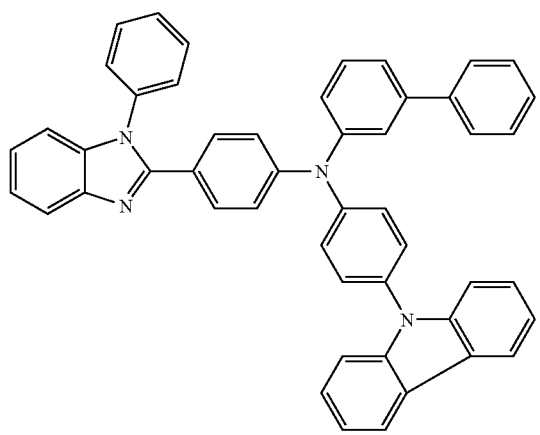

-continued
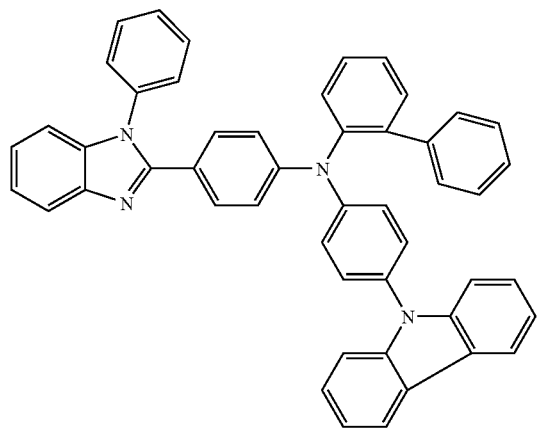
(264)
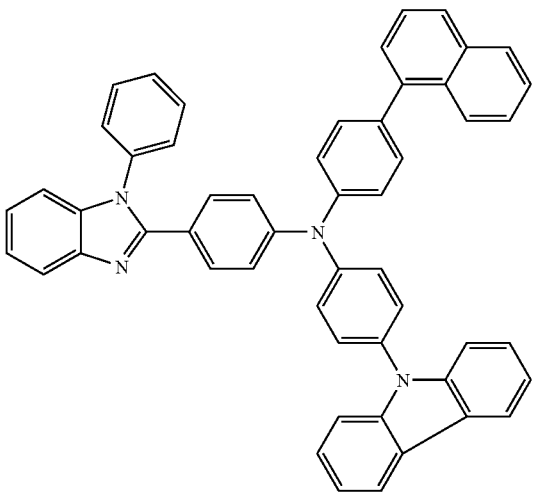
(265)
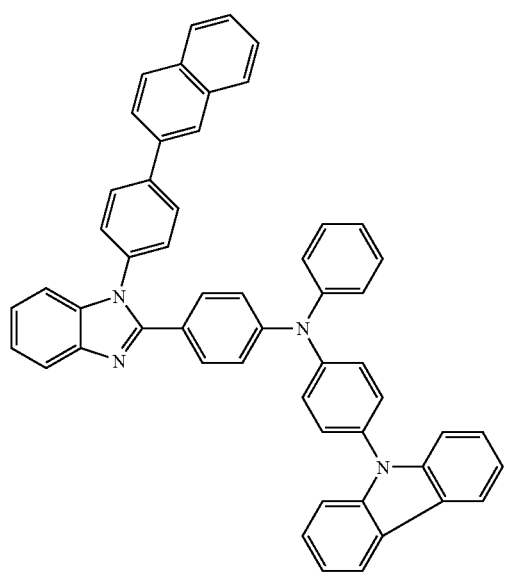
(266)
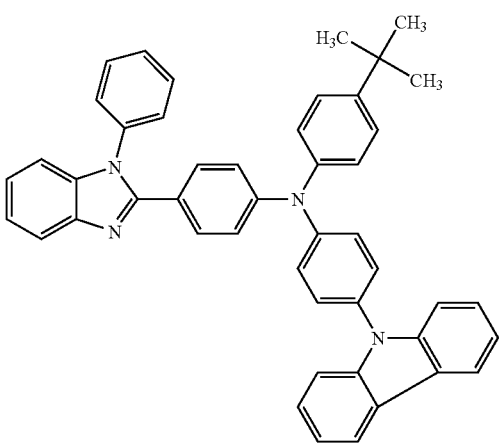
(267)
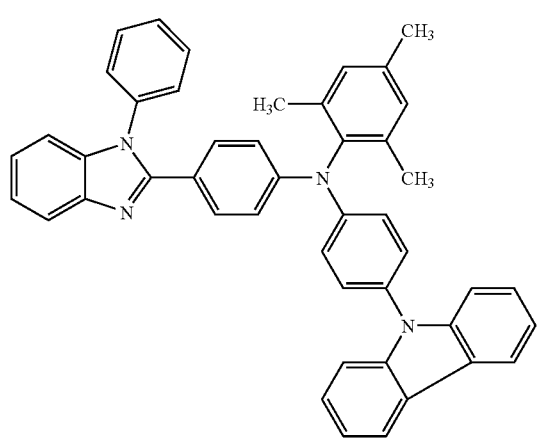
(268)
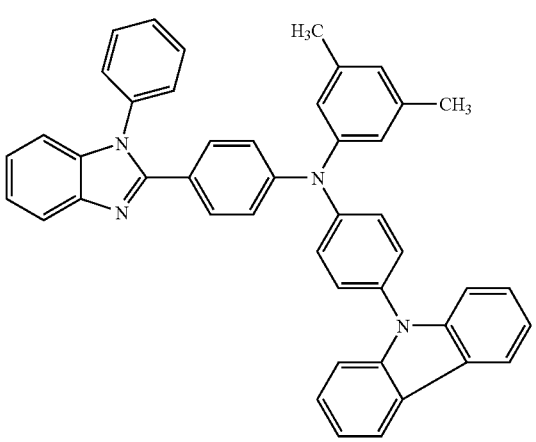
(269)

-continued
(270)
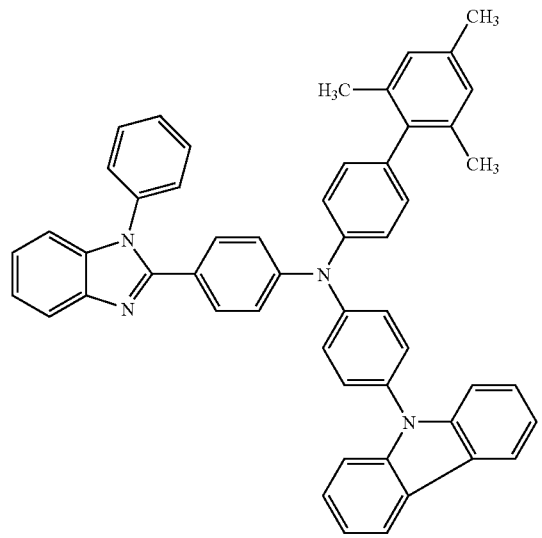
(271)
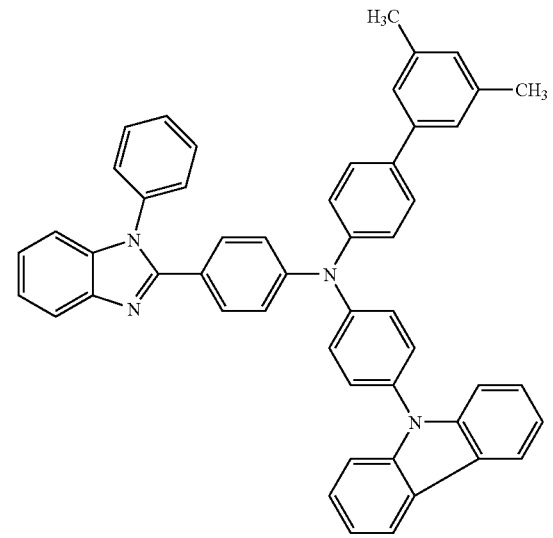
(272)
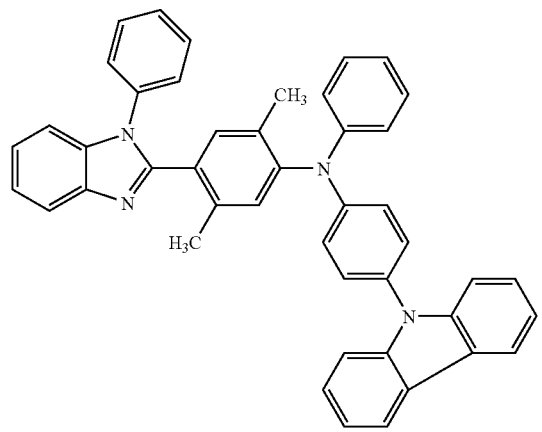
(273)
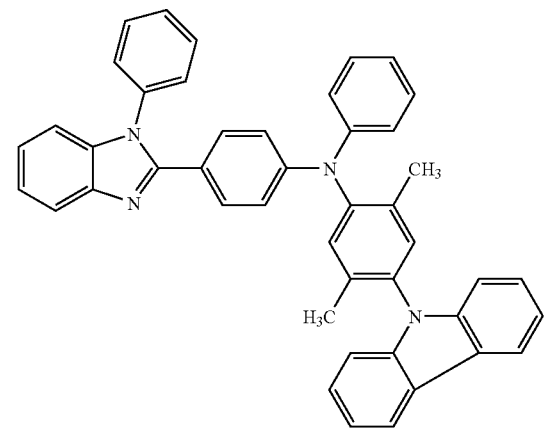
(274)
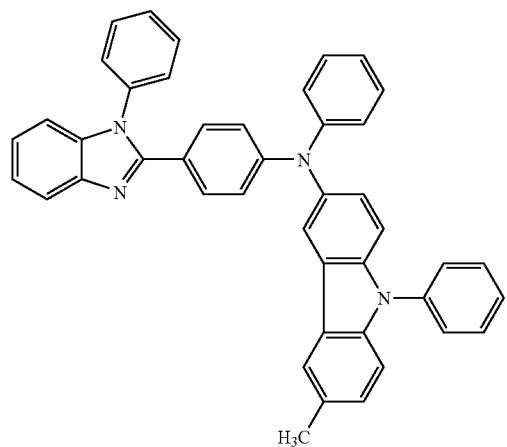
(275)
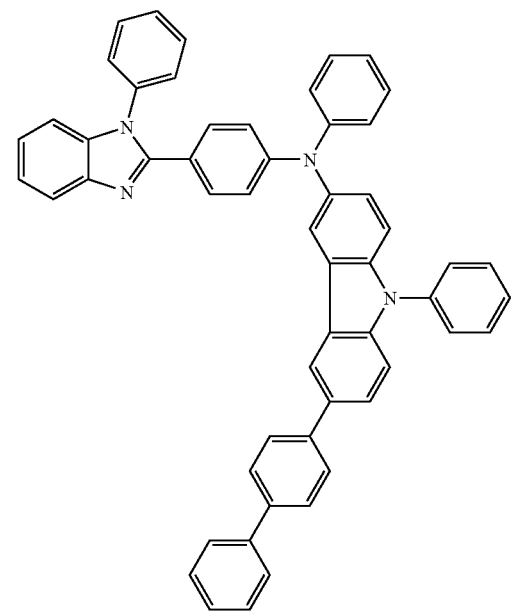

-continued
(276)
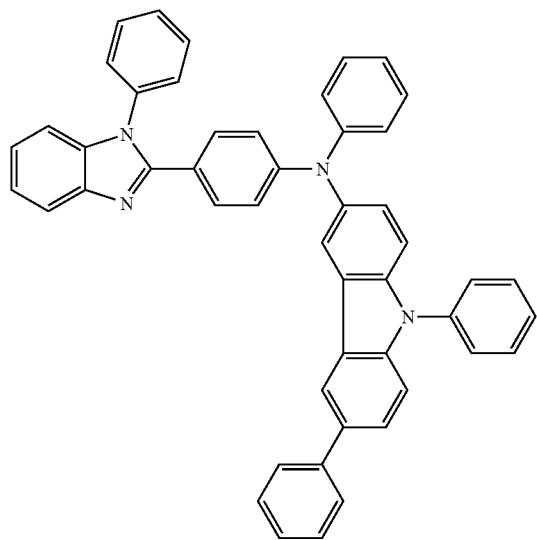
(277)
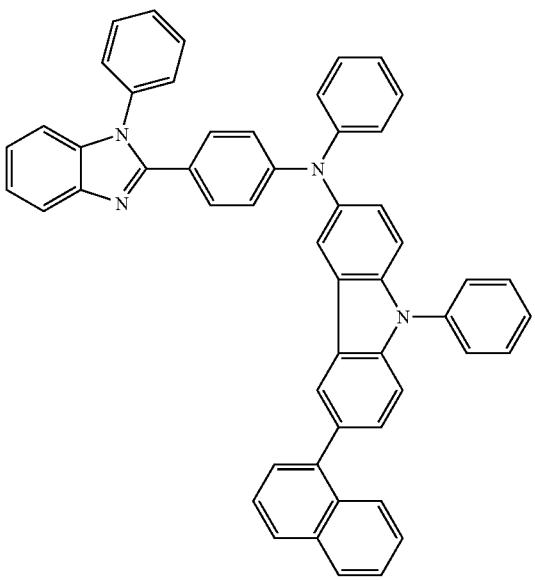
(278)
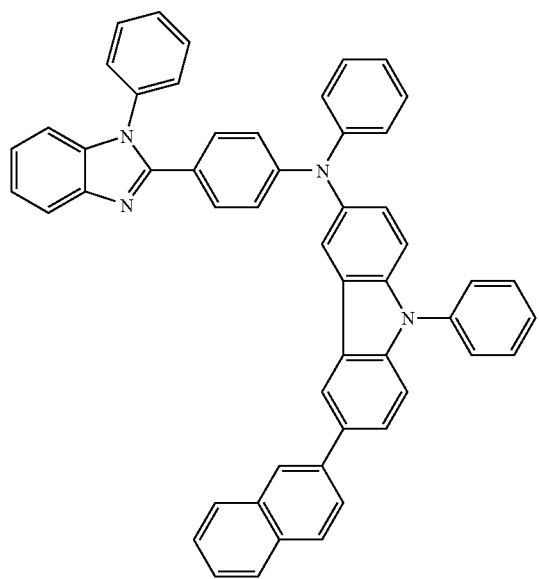
(279)
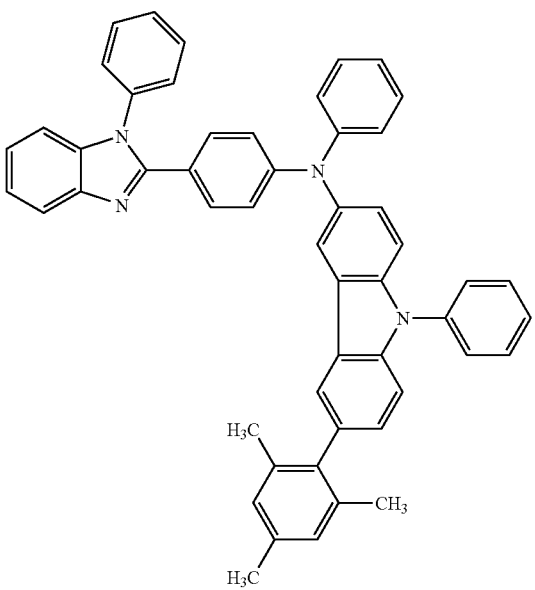
(280)
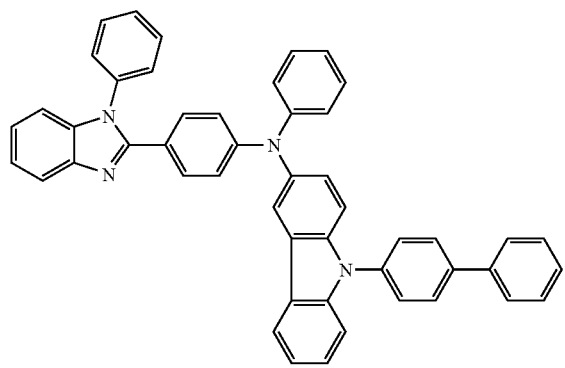
(281)
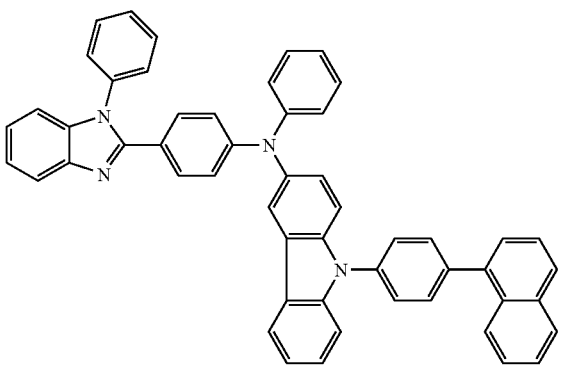

-continued
(282)
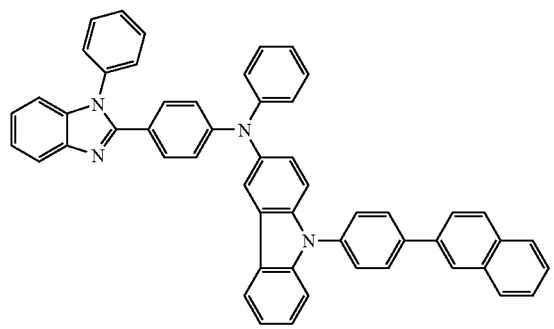
(283)
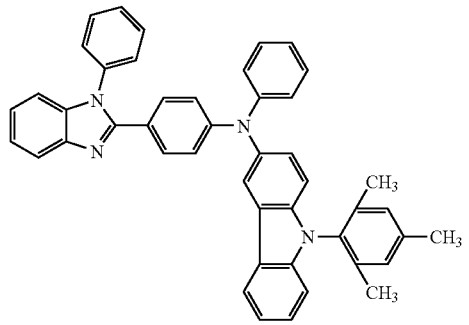
(284)
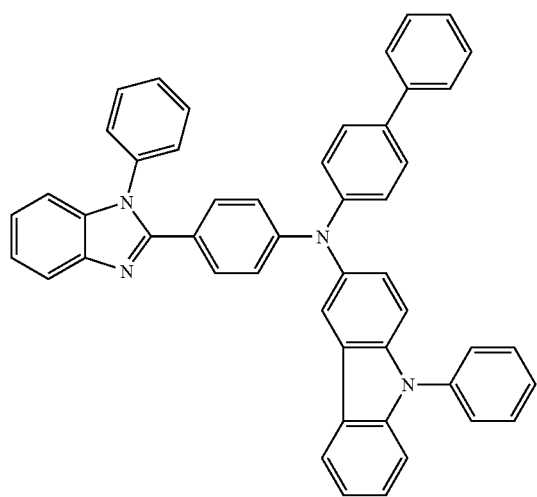
(285)
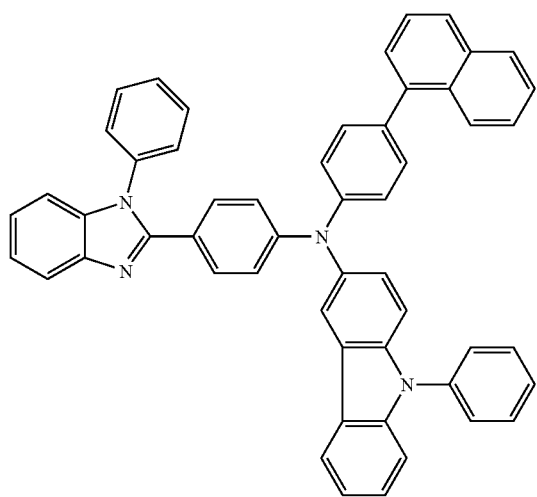
(286)
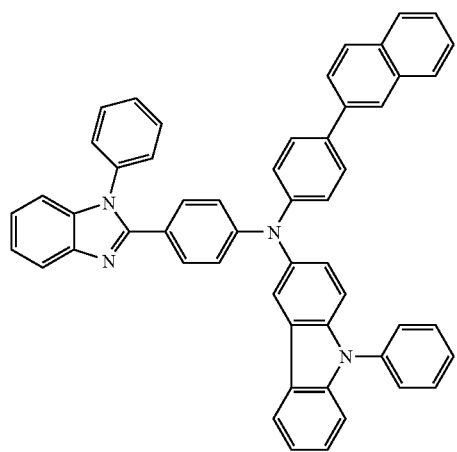
(287)
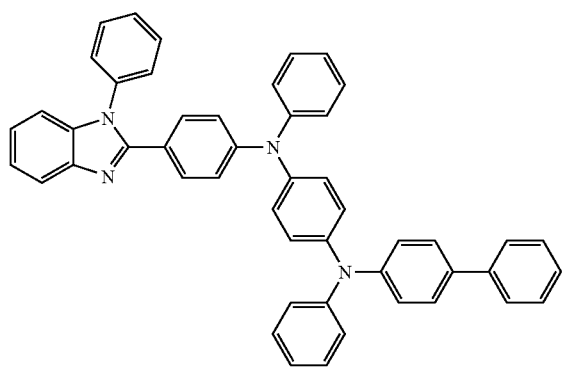

(288)
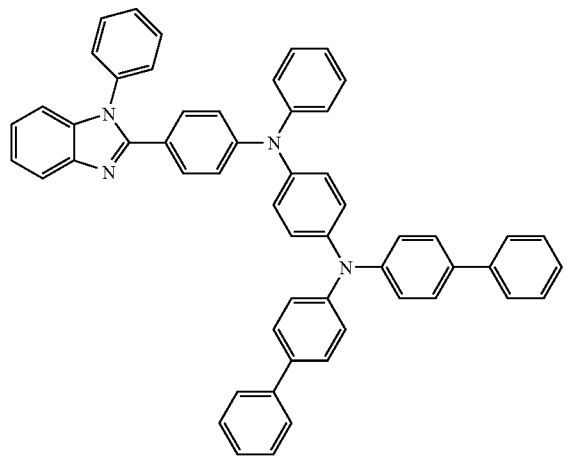

(289)
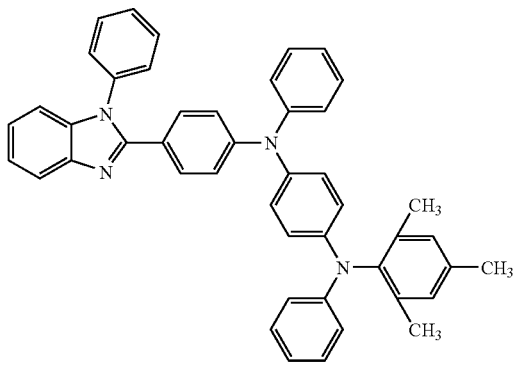

(290)
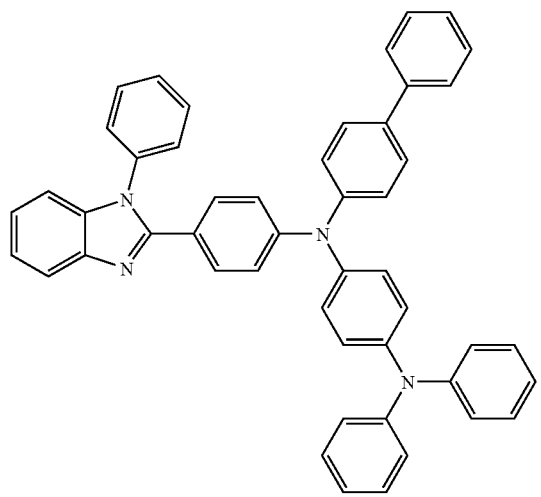

(291)
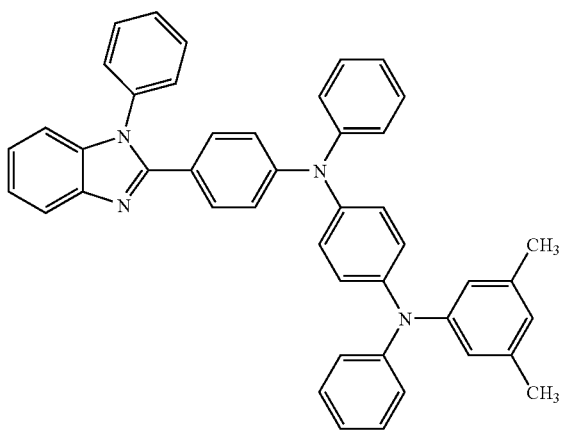

A variety of reactions can be applied to a synthesis method of the heterocyclic compound of this embodiment. For example, when a synthesis scheme (A-1) shown below is performed, the heterocyclic compound of this embodiment, which is represented by the general formula (G1), can be synthesized. Note that the synthesis method of the heterocyclic compound of this embodiment is not limited to the following synthesis method.

(A-1)

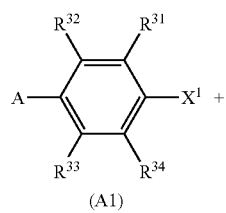

(A1)

-continued

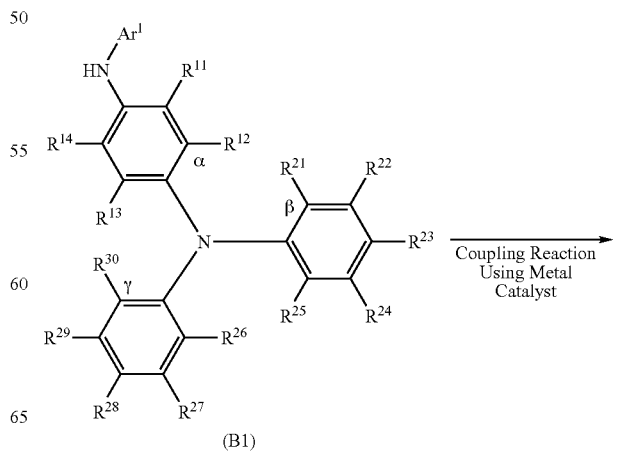

(B1)

Coupling Reaction Using Metal Catalyst →

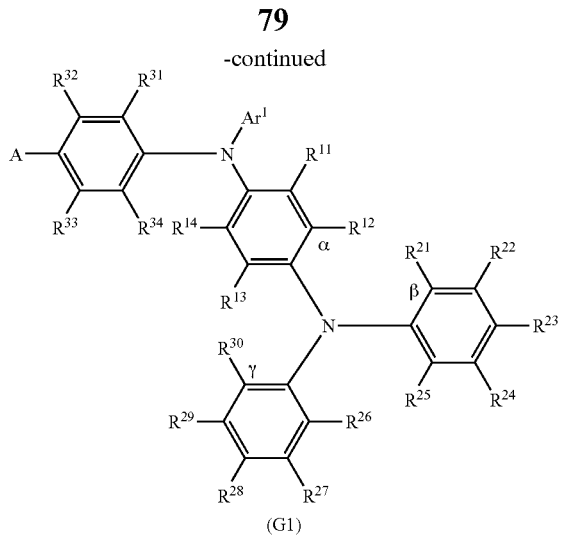

(G1)

When a halogenated heteroaryl derivative (Compound A1) and an aryl amine derivative (Compound B1) are coupled by the Buchwald-Hartwig reaction using a palladium catalyst or the Ullmann reaction using copper or a copper compound, the heterocyclic compound of this embodiment, which is represented by the general formula (G1), can be synthesized (synthesis scheme (A-1)).

In the synthesis scheme (A-1), $Ar^1$ represents a substituted or unsubstituted aryl group having 6 to 10 carbon atoms which form a ring. $R^{11}$ to $R^{14}$ and $R^{31}$ to $R^{34}$ each independently represent any one of a hydrogen atom, an alkyl group having 1 to 4 carbon atoms, or an aryl group having 6 to 10 carbon atoms which form a ring. $R^{21}$ to $R^{30}$ each independently represent any one of a hydrogen atom, an alkyl group having 1 to 4 carbon atoms, or a substituted or unsubstituted aryl group having 6 to 10 carbon atoms which form a ring. A represents any one of substituents represented by the following general formulae (S1-1) to (S1-3). In addition, any two of a carbon atom α, a carbon atom β, and a carbon atom γ may be combined to form a carbazole ring.

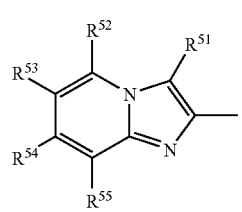

(S1-1)

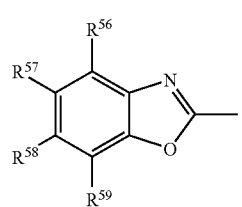

(S1-2)

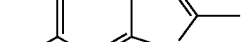

(S1-3)

In the general formulae (S1-1) to (S1-3), $R^{51}$ to $R^{64}$ each independently represent any one of a hydrogen atom, an alkyl group having 1 to 4 carbon atoms, or an aryl group having 6 to 10 carbon atoms which form a ring.

In the synthesis scheme (A-1), $X^1$ represents halogen. As halogen, iodine or bromine is preferable.

In the case where the Hartwig-Buchwald reaction is performed in the synthesis scheme (A-1), as a palladium catalyst which can be used, bis(dibenzylideneacetone)palladium(0), palladium(II)acetate, and the like are given. In the synthesis scheme (A-1), as examples of a ligand in the palladium catalyst which can be used, tri(tert-butyl)phosphine, tri(n-hexyl)phosphine, tricyclohexylphosphine, and the like are given.

In the synthesis scheme (A-1), as examples of a base which can be used, an organic base such as sodium tert-butoxide, an inorganic base such as potassium carbonate, and the like are given. In the synthesis scheme (A-1), a solvent which can be used, toluene, xylene, benzene, tetrahydrofuran, and the like are given.

The case where the Ullmann reaction is performed in the synthesis scheme (A-1) is described. In the synthesis scheme (A-1), as examples of a copper compound which can be used, copper(I) iodide, copper(II)acetate, and the like are given. Copper can be used instead of the copper compound. In the synthesis scheme (A-1), as a base which can be used, an inorganic base such as potassium carbonate is given. In the synthesis scheme (A-1), as examples of a solvent which can be used, 1,3-dimethyl-3,4,5,6-tetrahydro-2(1H)pyrimidinone (DMPU), toluene, xylene, benzene, and the like are given. In the Ullmann reaction, a target substance can be obtained in a shorter time and in a higher yield when the reaction temperature is 100° C. or higher; therefore, it is preferable to use DMPU or xylene that has a high boiling point. The reaction temperature is preferably 150° C. or higher; therefore, DMPU is more preferably used.

As described above, the heterocyclic compound of this embodiment can be synthesized.

The heterocyclic compound of this embodiment has high excitation energy, particularly high triplet excitation energy. Thus, the heterocyclic compound of this embodiment can be used as a host material of a light-emitting layer. When a guest material which serves as a light-emitting substance is dispersed in the heterocyclic compound of this embodiment, light can be emitted from the guest material which serves as a light-emitting substance. Further, the heterocyclic compound described in this embodiment has high triplet excitation energy; thus, a material which emits phosphorescence can be used as the guest material which serves as a light-emitting substance.

Further, the heterocyclic compound of this embodiment is a bipolar material having high electron injecting and transporting properties and high hole-injecting and transporting properties. Therefore, the heterocyclic compound of this embodiment can be used as a carrier transporting material for a function layer of a light-emitting element. The heterocyclic compound of this embodiment can be used for, for example, a hole-transporting layer, a hole-injecting layer, an electron-transporting layer, or an electron-injecting layer which is a carrier-transporting layer.

Further, when a light-emitting element is formed using the heterocyclic compound of this embodiment, the light-emitting element can have improved characteristics.

Embodiment 2

In Embodiment 2, an example of a light-emitting element in which any of the heterocyclic compounds described in Embodiment 1 is used for a light-emitting layer will be described with reference to the drawing.

FIG. 1 illustrates an example of a light-emitting element in which an EL layer 102 including a light-emitting layer 113 is interposed between a first electrode 101 and a second electrode 103.

When a voltage is applied to such a light-emitting element, holes injected from the first electrode 101 side and electrons injected from the second electrode 103 side are recombined in the light-emitting layer 113 to bring a light-emitting organic compound to an excited state. Then, the organic compound in the excited state emits light when it returns to the ground state. Note that, in the light-emitting element described in this embodiment, the first electrode 101 functions as an anode and the second electrode 103 functions as a cathode. Needless to say, the order of stacking layers may be reversed in the structure illustrated in FIG. 1.

The first electrode 101 which functions as an anode is preferably formed using a metal, an alloy, an electrically conductive compound, a mixture thereof, or the like which has a high work function (specifically, a work function of 4.0 eV or more). Specific examples include indium oxide-tin oxide (ITO: indium tin oxide), indium oxide-tin oxide containing silicon or silicon oxide, indium oxide-zinc oxide (IZO: indium zinc oxide), and indium oxide containing tungsten oxide and zinc oxide, and the like. Gold (Au), platinum (Pt), nickel (Ni), tungsten (W), chromium (Cr), molybdenum (Mo), iron (Fe), cobalt (Co), copper (Cu), palladium (Pd), titanium (Ti), or the like may be used.

Note that, when a layer in contact with the first electrode 101 which is included in the EL layer 102 is formed using a composite material of an organic compound and an electron acceptor (acceptor), a substance used for the first electrode 101 can be selected without being limited by the work function. For example, aluminum (Al), silver (Ag), an alloy containing aluminum (e.g., AlSi), or the like can be used.

Note that the first electrode 101 can be formed by, for example, a sputtering method, an evaporation method (e.g., a vacuum evaporation method), or the like.

The EL layer 102 formed over the first electrode 101 has at least the light-emitting layer 113 and is formed to contain any of the heterocyclic compounds described in Embodiment 1. For part of the EL layer 102, a known substance can be used, and either a low molecular compound or a high molecular compound may be used. Note that the substances forming the EL layer 102 may partly contain an inorganic compound.

Further, as illustrated in FIG. 1, the EL layer 102 includes, in addition to the light-emitting layer 113, the following layers stacked in appropriate combination: a hole-injecting layer 111 containing a substance having a high hole-injecting property, a hole-transporting layer 112 containing a substance having a high hole-transporting property, an electron-transporting layer 114 containing a substance having a high electron-transporting property, an electron-injecting layer 115 containing a substance having a high electron-injecting property, and the like.

The hole-injecting layer 111 is a layer containing a substance having a high hole-injecting property. As the substance having a high hole-injecting property, metal oxide such as molybdenum oxide, titanium oxide, vanadium oxide, rhenium oxide, ruthenium oxide, chromium oxide, zirconium oxide, hafnium oxide, tantalum oxide, silver oxide, tungsten oxide, or manganese oxide can be used. A phthalocyanine compound such as phthalocyanine (abbreviation: $H_2Pc$), copper(II) phthalocyanine (abbreviation: CuPc), or vanadyl phthalocyanine (abbreviation: VOPc) can be used.

The following aromatic amine compounds which are low molecular organic compounds can be used: 4,4',4"-tris(N,N-diphenylamino)triphenylamine (abbreviation: TDATA), 4,4', 4"-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N"-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), or the like.

A high molecular compound (such as an oligomer, a dendrimer, or a polymer) can be used. For example, any of the following high molecular compounds can be used: poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl) methacrylamide] (abbreviation: PTPDMA), and poly[N,N'-bis(4-butylphenyl)-N,N'-bis(phenyl)benzidine] (abbreviation: Poly-TPD). A high molecular compound to which acid is added, such as poly(3,4-ethylenedioxythiophene)/poly(styrenesulfonic acid) (PEDOT/PSS), or polyaniline/poly(styrenesulfonic acid) (PAni/PSS), can be used.

A composite material in which an organic compound and an electron acceptor (acceptor) are mixed may be used for the hole-injecting layer 111. Such a composite material is superior in a hole-injecting property and a hole-transporting property because holes are generated in the organic compound by the electron acceptor. In this case, as the organic compound, a material which can efficiently transport the generated holes (a substance having a high hole-transporting property) is preferably used.

An organic compound used for the above composite material preferably has a high hole-transporting property. Specifically, a substance having a hole mobility of $10^{-6}$ cm$^2$/Vs or higher is preferably used. Note that the organic compound is not to be construed as being limited to the substances described above as long as it has a hole-transporting property which is higher than an electron-transporting property. Specific examples of organic compounds which can be used for the composite material are given below.

Examples of the organic compound that can be used for the composite material include aromatic amine compounds such as TDATA, MTDATA, DPAB, DNTPD, DPA3B, PCzPCA1, PCzPCA2, PCzPCN1, 4,4'-bis[N-(1-naphthyl)-N-phenylamino]biphenyl (abbreviation: NPB), and N,N'-bis(3-methylphenyl)-N,N'-diphenyl-[1,1'-biphenyl]-4,4'-diamine (abbreviation: TPD) and carbazole derivatives such as 4,4'-di(N-carbazolyl)biphenyl (abbreviation: CBP), 1,3,5-tris[4-(N-carbazolyl)phenyl]benzene (abbreviation: TCPB), 9-[4-(N- carbazolyl)]phenyl-10-phenylanthracene (abbreviation: CzPA), and 1,4-bis[4-(N-carbazolyl)phenyl-2,3,5,6-tetraphenylbenzene.

Any of the following aromatic hydrocarbon compounds may be used: 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 9,10-bis[2-(1-naphthyl)phenyl]-2-tert-butylanthracene, 9,10-bis[2-(1-naphthyl)phenyl]anthracene, and 2,3,6,7-tetramethyl-9,10-di(1-naphthyl)anthracene.

Any of the following aromatic hydrocarbon compounds may be used: 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, pentacene, coronene, 4,4'-bis(2,2-diphenylvinyl)biphenyl (abbreviation: DPVBi), and 9,10-bis[4-(2,2-diphenylvinyl)phenyl]anthracene (abbreviation: DPVPA).

Any of the heterocyclic compounds described in Embodiment 1 may be used as the organic compound that is used for the composite material.

Further, as examples of electron acceptors that can be used for the composite material, there are organic compounds such as 7,7,8,8-tetracyano-2,3,5,6-tetrafluoroquinodimethane (abbreviation: $F_4$-TCNQ) and chloranil; transition metal oxide; and the like. Oxide of a metal belonging to Group 4 to Group 8 of the periodic table may be used. For example, vanadium oxide, niobium oxide, tantalum oxide, chromium oxide, molybdenum oxide, tungsten oxide, manganese oxide, and rhenium oxide are suitable because of their high electron-accepting properties. Among these, molybdenum oxide is easy to handle because of its stability in air and its low hygroscopic property.

Note that a composite material formed using any of the above high molecular compounds such as PVK, PVTPA, PTPDMA, and Poly-TPD and any of the above electron acceptors may be used for the hole-injecting layer 111.

The hole-transporting layer 112 is a layer containing a substance having a high hole-transporting property. As a substance having a high hole-transporting property, there are aromatic amine compounds such as NPB, TPD, 4,4'-bis[N-(9,9-dimethylfluoren-2-yl)-N-phenylamino]biphenyl (abbreviation: DFLDPBi), and 4,4'-bis[N-(spiro-9,9'-bifluoren-2-yl)-N-phenylamino]biphenyl (abbreviation: BSPB). The substances mentioned here are mainly ones that have a hole mobility of $10^{-6}$ cm$^2$/Vs or higher. Note that the hole-transporting layer 112 may have a single-layer structure or a stacked-layer structure.

For the hole-transporting layer 112, a high molecular compound such as PVK, PVTPA, PTPDMA, or Poly-TPD can be used.

Any of the heterocyclic compounds described in Embodiment 1 can be used for the hole-transporting layer 112.

The light-emitting layer 113 is a layer containing a substance having a high light-emitting property. Note that in this embodiment, a case where any of the heterocyclic compounds described in Embodiment 1 is used for a light-emitting layer is described. The above heterocyclic compounds are suitably used as a host material in a light-emitting layer where a substance having a high light-emitting property (a guest material) is dispersed in another substance (a host material). However, embodiments of the disclosed invention are not to be construed as being limited to this. Any of the above heterocyclic compounds may be used alone for the light-emitting layer.

In the case where any of the heterocyclic compounds described in Embodiment 1 is used as a host material and a material that emits fluorescence is used as a guest material, it is preferable to use, as the guest material, a material whose lowest unoccupied molecular orbital (LUMO) level is lower and highest occupied molecular orbital (HOMO) level is higher than those of the heterocyclic compounds described in Embodiment 1. As examples of materials emitting blue light, N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), and the like are given. In addition, examples of materials emitting green light, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), N-[9,10-bis(1,1'-biphenyl-2-yl)]-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), and the like are given. As examples of materials emitting yellow light, rubrene, 5,12-bis(1,1'-biphenyl-4-yl)-6,11-diphenyltetracene (abbreviation: BPT), and the like are given. As examples of materials emitting red light, N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-α]fluoranthene-3,10-diamine (abbreviation: p-mPhAFD), and the like are given.

In the case where any of the heterocyclic compounds described in Embodiment 1 is used as a host material and a material which emits phosphorescence is used as a guest material, a material having lower triplet excitation energy than the heterocyclic compound described in Embodiment 1 is preferably used as the guest material. As examples of such materials, the following are given: organometallic complexes such as bis[2-(3',5'-bistrifluoromethylphenyl)pyridinato-N,$C^{2'}$]iridium(III) picolinate (abbreviation: Ir(CF$_3$ppy)$_2$(pic)), bis[2-(4',6'-difluorophenyl)pyridinato-N,$C^{2'}$]iridium(III) acetylacetonate (abbreviation: FIracac), tris(2-phenylpyridinato-N,$C^{2'}$)iridium(III) (abbreviation: Ir(ppy)$_3$), bis(2-phenylpyridinato)iridium(III) acetylacetonato (abbreviation: Ir(ppy)$_2$(acac)), tris(acetylacetonato)(monophenanthroline)terbium(III) (abbreviation: Tb(acac)$_3$(Phen)), bis(benzo[h]quinolinato)iridium(III) acetylacetonate (abbreviation: Ir(bzq)$_2$(acac)), bis(2,4-diphenyl-1,3-oxazolato-N,$C^{2'}$)iridium(III) acetylacetonate (abbreviation: Ir(dpo)$_2$(acac)), bis[2-(4'-perfluorophenylphenyl)pyridinato]iridium(III)acetylacetonate (abbreviation: Ir(p-PF-ph)$_2$(acac)), bis(2-phenylbenzothiazolato-N,$C^{2'}$)iridium(III) acetylacetonate (abbreviation: Ir(bt)$_2$(acac)), bis[2-(2'-benzo[4,5-α]thienyl)pyridinato-N,$C^{3'}$]iridium(III) acetylacetonate (abbreviation: Ir(btp)$_2$(acac)), bis(1-phenylisoquinolinato-N,$C^{2'}$)iridium(III) acetylacetonate (abbreviation: Ir(piq)$_2$(acac)), (acetylacetonato)bis[2,3-bis(4-fluorophenyl)quinoxalinato]iridium(III) (abbreviation: Ir(Fdpq)$_2$(acac)), (acetylacetonato)bis(2,3,5-triphenylpyrazinato)iridium(III) (abbreviation: Ir(tppr)$_2$(acac)), 2,3,7,8,12,13,17,18-octaethyl-21H,23H-porphyrin platinum(II) (abbreviation: PtOEP), tris(1,3-diphenyl-1,3-propanedionato)(monophenanthroline)europium(III) (abbreviation: Eu(DBM)$_3$(Phen)), and tris[1-(2-thenoyl)-3,3,3-trifluoroacetonato](monophenanthroline)europium(III) (abbreviation: Eu(TTA)$_3$(Phen)).

The heterocyclic compounds described in Embodiment 1 have an electron-transporting property. Therefore, when any of the heterocyclic compounds is used for a light-emitting layer, the light-emitting layer can have a high electron-transporting property. In the case where a guest material having a high electron-trapping property is used for the light-emitting layer having such a structure, light emission with extremely high efficiency can be obtained.

As the substance (host material) into which the substance having a light-emitting property (guest material) is dispersed, plural kinds of substances can be used. Therefore, the light-emitting layer may include a second host material in addition to any of the heterocyclic compounds described in Embodiment 1.

Any of the above heterocyclic compounds can be used alone as a light-emitting substance, and further can be used as a guest material.

The electron-transporting layer 114 is a layer containing a substance having a high electron-transporting property. For the electron-transporting layer 114, it is possible to use a metal complex such as Alq$_3$, tris(4-methyl-8-quinolinolato) aluminum (abbreviation: Almq$_3$), bis(10-hydroxybenzo[h] quinolinato)beryllium (abbreviation: BeBq$_2$), BAlq, Zn(BOX)$_2$, or bis[2-(2-hydroxyphenyl)benzothiazolato]zinc (II) (abbreviation: Zn(BTZ)$_2$). It is possible to use a heteroaromatic compound such as 2-(4-biphenylyl)-5-(4-tert-butylphenyl)-1,3,4-oxadiazole (abbreviation: PBD), 1,3-bis [5-(p-tert-butylphenyl)-1,3,4-oxadiazol-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), or 4,4'-bis(5-methylbenzoxazol-2-yl)stilbene (abbreviation: BzOs). A high molecular compound such as poly(2,5-pyridinediyl) (abbreviation: PPy), poly[(9,9-dihexylfluorene-2,7-diyl)-co-(pyridine-3,5-diyl)] (abbreviation: PF-Py), or poly [(9,9-dioctylfluorene-2,7-diyl)-co-(2,2'-bipyridine-6,6'-diyl)] (abbreviation: PF-BPy) may be used. The substances given here are mainly substances which have an electron mobility of $10^{-6}$ cm$^2$/Vs or higher.

Further, the electron-transporting layer 114 may have a single-layer structure or a stacked-layer structure.

The electron-injecting layer 115 is a layer containing a substance having a high electron-injecting property. For the electron-injecting layer 115, an alkali metal, an alkaline earth metal, or a compound thereof, such as lithium fluoride (LiF), cesium fluoride (CsF), calcium fluoride (CaF$_2$), or lithium oxide (LiO$_x$) can be used. A rare earth metal compound like erbium fluoride (ErF$_3$) can be used. Any of the above-described substances that are used for forming the electron-transporting layer 114 may be used.

For the electron-injecting layer 115, a composite material in which an organic compound and an electron donor (donor) are mixed may be used. Such a composite material is superior in an electron-injecting property and an electron-transporting property because electrons are generated in the organic compound by the electron donor. In this case, as the organic compound, a material that is excellent in transporting generated electrons is preferably used: for example, any of the above-described substances that are used for forming the electron-transporting layer 114 can be used. Any of the heterocyclic compounds described in Embodiment 1 may be used. As the electron donor, a substance exhibiting an electron-donating property with respect to the organic compound may be used. Specifically, it is preferable to use any of an alkali metal, an alkaline earth metal, or a rare earth metal, such as lithium, cesium, magnesium, calcium, erbium, or ytterbium. It is preferable to use any of alkali metal oxide or alkaline earth metal oxide, such as lithium oxide, calcium oxide, or barium oxide. Lewis base such as magnesium oxide can be used. An organic compound such as tetrathiafulvalene (abbreviation: TTF) can be used.

Note that each of the above-described hole-injecting layer 111, hole-transporting layer 112, light-emitting layer 113, electron-transporting layer 114, and electron-injecting layer 115 can be formed by a method such as an evaporation method (e.g., a vacuum evaporation method), an inkjet method, or a coating method.

The second electrode 103 which functions as a cathode is preferably formed using a metal, an alloy, an electrically conductive compound, a mixture thereof, or the like which has a low work function (preferably, 3.8 eV or lower), or the like. Specifically, any of the following materials can be used: Al, silver, and the like, as well as elements that belong to Group 1 or Group 2 of the periodic table, that is, alkali metals such as lithium (Li) and cesium (Cs) or alkaline earth metals such as magnesium (Mg), calcium (Ca), and strontium (Sr), or alloys thereof (e.g., MgAg and AlLi); rare earth metals such as europium (Eu) and ytterbium (Yb), or alloys thereof.

Note that, when a layer in contact with the second electrode 103 which is included in the EL layer 102 is formed using the above-described composite material of the organic compound and the electron donor, a material used for the second electrode 103 can be selected without being limited by the work function. For example, any of a variety of conductive materials such as Al, Ag, ITO (indium oxide-tin oxide), and indium oxide-tin oxide containing silicon or silicon oxide can be used.

Note that the second electrode 103 can be formed by a vacuum evaporation method or a sputtering method. When a silver paste or the like is used, a coating method, an inkjet method, or the like may be used.

In the above-described light-emitting element of the present invention, light is emitted when holes and electrons generated by a potential difference between the first electrode 101 and the second electrode 103 are recombined in the EL layer 102. Then, this light emission is extracted through either the first electrode 101 or the second electrode 103, or both of them. Accordingly, either the first electrode 101 or the second electrode 103 or both of them have a light-transmitting property.

Note that with the use of the light-emitting element described in this embodiment, a passive matrix light-emitting device or an active matrix light-emitting device in which driving of the light-emitting element is controlled by a thin film transistor (TFT) can be manufactured.

Note that there is no particular limitation on the structure of the TFT in the case of manufacturing an active matrix light-emitting device. Further, either an n-type TFT or a p-type TFT may be used. Furthermore, there is also no particular limitation on a semiconductor material used for the TFT. For example, any of the following materials can be used: silicon-based semiconductor materials (which may be amorphous, crystalline, or single crystal), germanium-based semiconductor materials, chalcogenide-based semiconductor materials, or other variety of semiconductor materials. Needless to say, an oxide semiconductor material may be used.

In this embodiment, the light-emitting layer 113 is formed using any of the above heterocyclic compounds. Accordingly, a light-emitting element with high power efficiency and long lifetime can be provided.

Note that this embodiment can be used in appropriate combination with the structure described in the above embodiment.

Embodiment 3

A light-emitting element which is an embodiment of the disclosed invention may have a plurality of light-emitting layers. When light is emitted from the plurality of light-emitting layers, light which is a combination thereof can be obtained. Thus, for example, white light emission can be obtained. In Embodiment 3, one embodiment of a light-emitting element having a plurality of light-emitting layers will be described with reference to the drawing.

Figure 2:
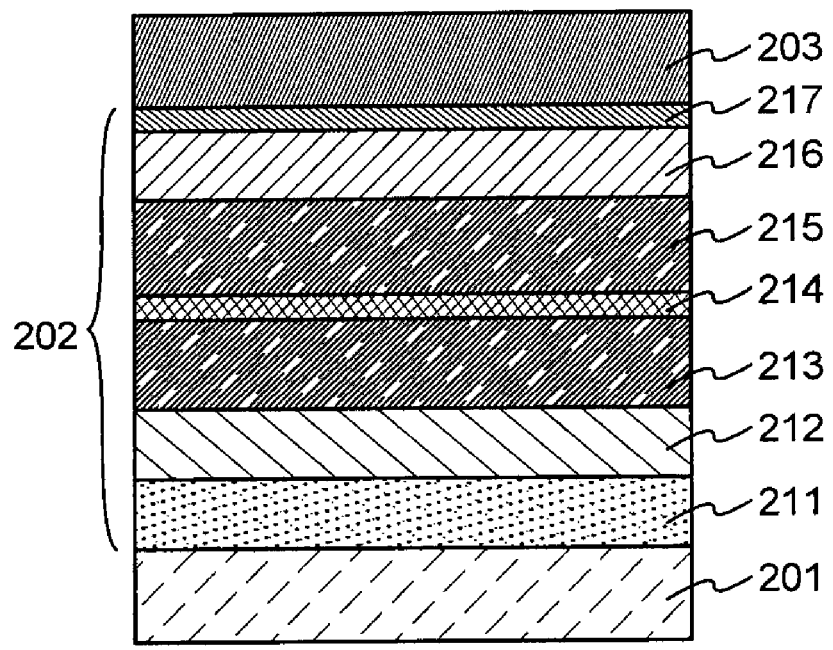
FIG. 2 is a view illustrating a light-emitting element.

In FIG. 2, a first light-emitting layer 213 and a second light-emitting layer 215 are provided between a first electrode 201 and a second electrode 203. Light which is a combination of light emitted from the first light-emitting layer 213 and light emitted from the second light-emitting layer 215 can be obtained. A separation layer 214 is preferably formed between the first light-emitting layer 213 and the second light-emitting layer 215.

When a voltage is applied so that the potential of the first electrode 201 is higher than that of the second electrode 203, a current flows between the first electrode 201 and the second electrode 203, and holes or electrons move to the first light-emitting layer 213, the second light-emitting layer 215, or the separation layer 214. Accordingly, a first light-emitting substance contained in the first light-emitting layer 213 and a second light-emitting substance contained in the second light-emitting layer 215 are raised to an excited state. Then, the light-emitting substances in the excited state emit light when they return to the ground state.

The first light-emitting layer 213 contains the first light-emitting substance typified by a fluorescent compound such as perylene, 2,5,8,11-tetra(tert-butyl)perylene (abbreviation: TBP), DPVBi, 4,4'-bis[2-(N-ethylcarbazol-3-yl)vinyl]biphenyl (abbreviation: BCzVBi), BAlq, or bis(2-methyl-8-quinolinolato)galliumchloride (abbreviation: $Gamq_2Cl$); or a phosphorescent substance such as bis{2-[3,5-bis(trifluoromethyl)phenyl]pyridinato-N,$C^{2'}$}iridium(III) picolinate (abbreviation: Ir($CF_3$ppy)$_2$(pic)), bis[2-(4,6-difluorophenyl)pyridinato-N,$C^{2'}$]iridium(III)acetylacetonate (abbreviation: FIr(acac)), bis[2-(4,6-difluorophenyl)pyridinato-N,$C^{2'}$]iridium(III) picolinate (abbreviation: FIrpic), or bis[2-(4,6-difluorophenyl)pyridinato-N,$C^{2'}$]iridium(III)tetra(1-pyrazolyl)borate (abbreviation: FIr6), from which light emission having a peak at 450 nm to 510 nm in an emission spectrum (i.e., blue light to blue green light) can be obtained.

When a fluorescent compound is used as the first light-emitting substance, the first light-emitting layer 213 preferably has a structure in which a substance having higher singlet excited energy than the first light-emitting substance is used as a first host and the first light-emitting substance is dispersed as a guest. When a phosphorescent compound is used as the first light-emitting substance, the first light-emitting layer 213 preferably has a structure in which a substance having higher triplet excited energy than the first light-emitting substance is used as a first host and the first light-emitting substance is dispersed as a guest. As the first host, DNA, t-BuDNA, or the like can be used in addition to the above-described NPB, CBP, TCTA, and the like. Note that the singlet excitation energy refers to a difference in energy between a ground state and a singlet excited state. The triplet excitation energy refers to a difference in energy between a ground state and a triplet excited state.

In contrast, the second light-emitting layer 215 contains any of the heterocyclic compounds described in Embodiment 1. The structure of the second light-emitting layer 215 is similar to that of the light-emitting layer 113 which is described in Embodiment 2.

Further, the separation layer 214 can be formed using, for example, TPAQn, NPB, CBP, TCTA, $Znpp_2$, ZnBOX or the like described above. The provision of such a separation layer 214 makes it possible to prevent an undesirable increase in the emission intensity of only either the first light-emitting layer 213 or the second light-emitting layer 215. Note that the separation layer 214 is not a necessary component. For example, the separation layer 214 may be provided in the case where the ratio of the emission intensity of the first light-emitting layer 213 to that of the second light-emitting layer 215 needs to be adjusted. Further, any of the heterocyclic compounds each of which is an embodiment of the disclosed invention may be used for the separation layer 214.

In this embodiment, any of the heterocyclic compounds described in Embodiment 1 is used for the second light-emitting layer 215 and another light-emitting substance is used for the first light-emitting layer 213 in this embodiment. However, any of the heterocyclic compounds described in Embodiment 1 may be used for the first light-emitting layer 213 and another light-emitting substance may be used for the second light-emitting layer 215.

Further, although a light-emitting element including two light-emitting layers is described in this embodiment, the number of light-emitting layers is not limited to two and may be three or more.

Note that the first electrode 201 has a structure similar to that of the first electrode 101 which is described in Embodiment 2. Also, the second electrode 203 has a structure similar to that of the second electrode 103 which is described in Embodiment 2.

Further, in this embodiment, an example in which a hole-injecting layer 211, a hole-transporting layer 212, an electron-transporting layer 216, and an electron-injecting layer 217 are provided. The structures described in Embodiment 2 can be applied to these layers. However, they are not necessary components. These layers are provided in accordance with element characteristics.

Note that this embodiment can be used in appropriate combination with any of the structures described in the above embodiments.

Embodiment 4

In Embodiment 4, a light-emitting element having a plurality of EL layers (hereinafter, referred to as a stacked-type element) will be described with reference to the drawing.

Figure 3:
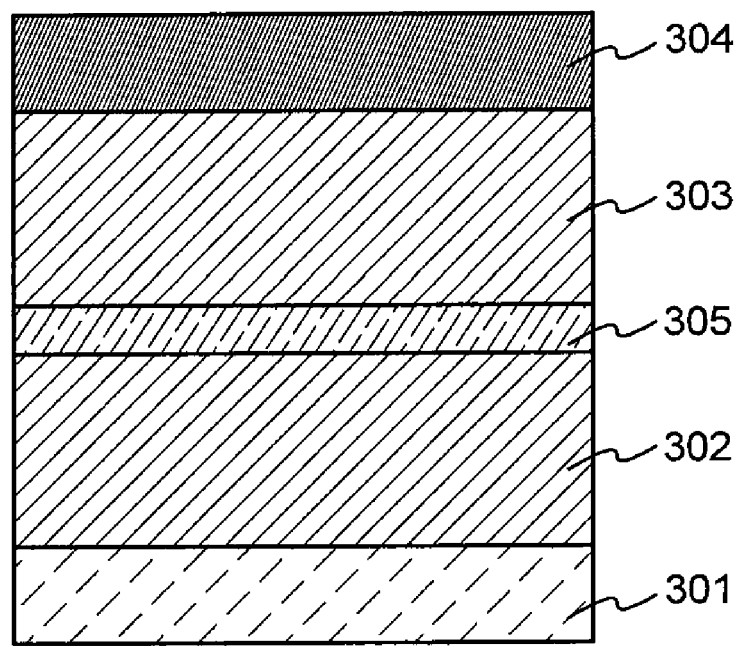
FIG. 3 is a view illustrating a light-emitting element.

FIG. 3 illustrates a stacked-type light-emitting element which has a plurality of EL layers (a first EL layer 302 and a second EL layer 303) between a first electrode 301 and a second electrode 304. Note that although a structure in which two EL layers are formed is described in this embodiment, three or more EL layers may be formed.

In this embodiment, the first electrode 301 functions as an anode and the second electrode 304 functions as a cathode. Note that the first electrode 301 and the second electrode 304 can have structures similar to those described in the above embodiments. Further, although the plurality of EL layers (the first EL layer 302 and the second EL layer 303) may be formed as described in the above embodiments, either layer may have a structure different from that described in the above embodiments. In other words, the structures of the first EL layer 302 and the second EL layer 303 may be the same or different from each other.

Further, a charge generation layer 305 is provided between the plurality of EL layers (the first EL layer 302 and the second EL layer 303). The charge generation layer 305 has a function of injecting electrons into one of the EL layers and injecting holes into the other of the EL layers when a voltage is applied to the first electrode 301 and the second electrode 304. In this embodiment, when a voltage is applied so that the potential of the first electrode 301 is higher than that of the second electrode 304, electrons are injected into the first EL layer 302 and holes are injected into the second EL layer 303 from the charge generation layer 305.

Note that the charge generation layer 305 preferably has a light-transmitting property in terms of light extraction efficiency. Further, the electric conductivity of the charge generation layer 305 may be lower than that of the first electrode 301 or the second electrode 304.

The charge generation layer 305 may contain an organic compound having a high hole-transporting property and an electron acceptor (acceptor). The charge generation layer 305 may contain an organic compound having a high electron-transporting property and an electron donor (donor). The charge generation layer 305 may contain the above components stacked.

The description in the above embodiment can be referred to for details of the organic compound having a high hole-transporting property and the electron acceptor. Similarly, the description in the above embodiment can be referred to for details of the organic compound having a high electron-transporting property and the electron donor.

When the charge generation layer 305 is formed using the above materials, an increase in drive voltage which is caused by the stack of the EL layers can be suppressed.

By arrangement in which the charge generation layer partitions the plurality of EL layers, as in the light-emitting element according to this embodiment, luminance can be increased while current density is kept low. Thus, a light-emitting element which emits light with high luminance and has long lifetime can be achieved.

Further, when the EL layers are formed to emit light of different colors, an emission color that is provided by the whole light-emitting element can be controlled. For example, when a light-emitting element having two EL layers are formed so that the emission color of the first EL layer and the emission color of the second EL layer are complementary colors, the light-emitting element can provide white light emission as a whole. Note that "complementary colors" refer to colors that can produce an achromatic color when mixed. In other words, when light of complementary colors is mixed, white light emission can be obtained. This can be applied to a light-emitting element having three or more EL layers.

Note that this embodiment can be used in appropriate combination with any of the structures described in the above embodiments.

Embodiment 5

In Embodiment 5, as an embodiment of the disclosed invention, a passive matrix light-emitting device and an active matrix light-emitting device in each of which a light-emitting element is used will be described.

FIGS. 4A to 4D and FIG. 5 illustrate examples of passive-matrix light-emitting devices.

In a passive matrix (also referred to as simple matrix) light-emitting device, a plurality of anodes arranged in stripes (in a stripe form) are provided orthogonal to a plurality of cathodes arranged in stripes. A light-emitting layer is formed at each intersection. Therefore, light is emitted from a light-emitting layer (hereinafter, referred to as a pixel) at an intersection of an anode selected (to which a voltage is applied) and a cathode selected.

Figure 4A:
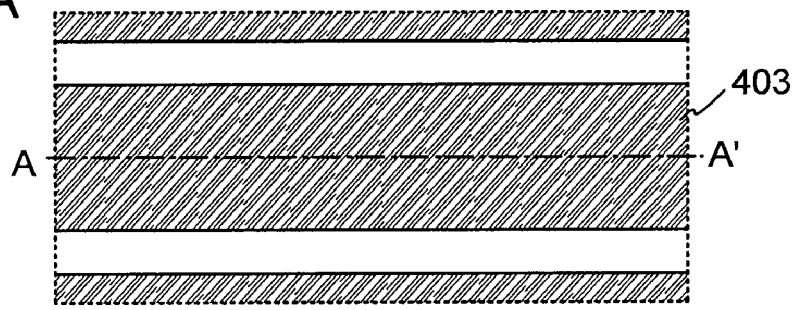
FIGS. 4A to 4D are views illustrating a passive matrix light-emitting device.
Figure 4B:
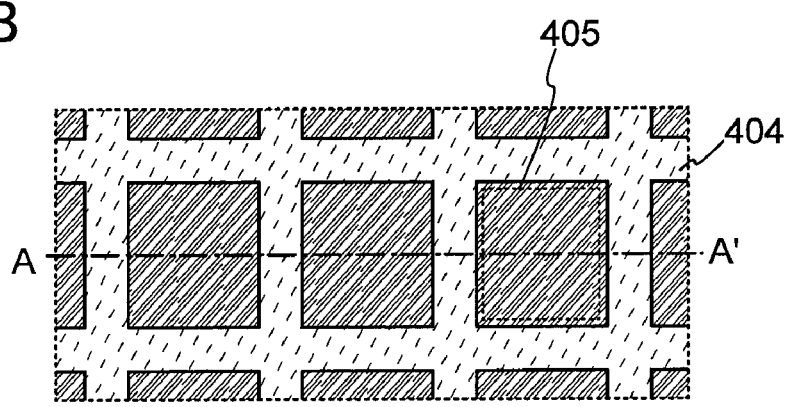
Figure 4C:
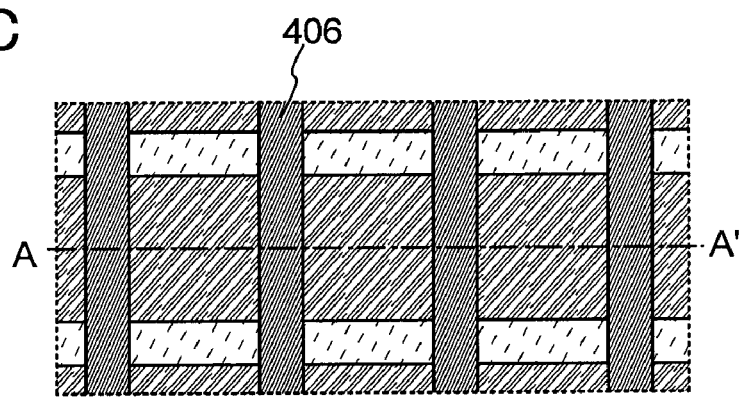
Figure 4D:
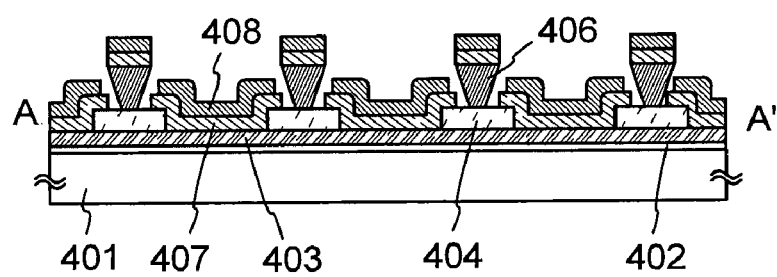

FIGS. 4A to 4C are top views of a pixel portion before sealing. FIG. 4D is a cross-sectional view taken along dashed line A-A' in each of FIGS. 4A to 4C.

Over a substrate 401, an insulating layer 402 is formed as a base insulating layer. Note that the base insulating layer is not a necessary component, and thus may be formed as needed. A plurality of first electrodes 403 are arranged at regular intervals over the insulating layer 402 (see FIG. 4A).

In addition, a partition 404 having openings in regions corresponding to pixels is provided over the first electrodes 403. The partition 404 having openings is formed using an organic material (polyimide, acrylic, polyamide, polyimide amide, resist, or benzocyclobutene), an inorganic material (e.g., SiOx including an alkyl group), or the like. Note that openings 405 corresponding to the pixels serve as light-emitting regions (see FIG. 4B).

Over the partition 404, a plurality of partitions 406 are provided so as to intersect with the first electrodes 403 (see FIG. 4C). The plurality of partitions 406 are each reversely tapered and arranged in parallel to one another.

In regions over the first electrodes 403, in which the partitions 406 are not formed, EL layers 407 and second electrodes 408 are provided in this order (see FIG. 4D). Here, the EL layers 407 and the second electrodes 408 are formed as plural portions which are electrically isolated. The EL layer 407 and the second electrode 408 having such a structure can be formed when the partition 406 is formed so that the height thereof is larger than the sum of the thicknesses of the EL layer 407 and the second electrode 408.

The second electrodes 408 extend in the direction in which they intersect with the first electrodes 403. Note that over the partition 406, a layer formed using the same material as the EL layer 407 and a layer formed using the same material as the second electrode 408 are also formed, which are separated from the EL layer 407 and the second electrode 408.

Note that the first electrode 403 and the second electrode 408 may serve as an anode and a cathode, respectively, or vice versa. The stacked-layer structure of the EL layer 407 is adjusted as appropriate depending on the polarity of the electrodes.

Further, the substrate 401 may be sealed so that a light-emitting element is provided in a sealed space. Sealing is performed using an adhesive such as a sealing material to attach the substrate 401 to a sealing can or a sealant. Such sealing makes it possible to suppress deterioration of the light-emitting element. Note that the sealed space may be filled with a filler, a dried inert gas, a drying agent (a desiccant), or the like. When sealing a drying agent is put, a minute amount of moisture is removed; therefore, deterioration of the light-emitting element which is caused by moisture is suppressed. Note that as a drying agent, a substance that adsorbs moisture by chemical adsorption can be used. For example, oxide of an alkaline earth metal such as calcium oxide or barium oxide can be used. A substance that adsorbs moisture by physical adsorption, such as zeolite or silica gel, may be used.

Figure 5:
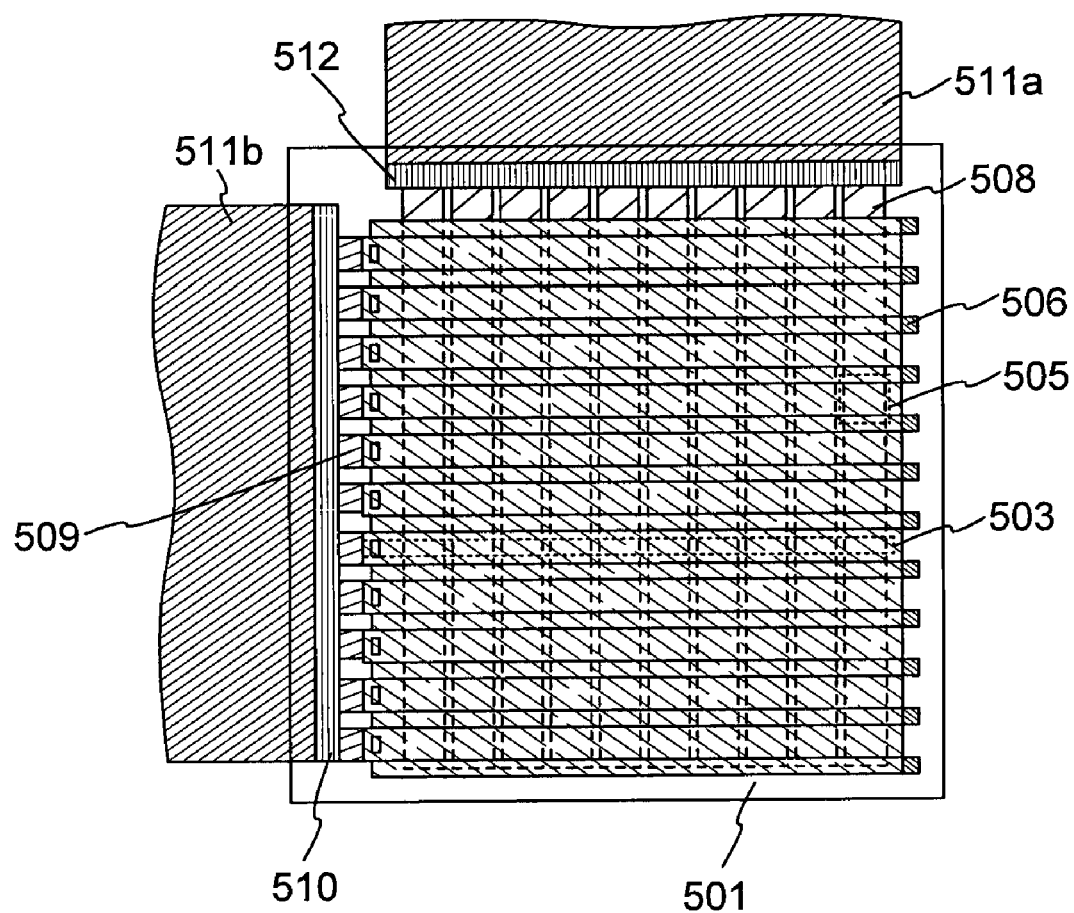
FIG. 5 is a view illustrating a passive matrix light-emitting device.

Next, FIG. 5 illustrates a structure of a passive matrix light-emitting device illustrated in FIGS. 4A to 4D, on which an FPC and the like are mounted.

In a pixel portion in FIG. 5, scan lines and data lines intersect with each other so as to be orthogonal to each other. Note that the first electrodes 403 in FIGS. 4A to 4D correspond to scan lines 503 in FIG. 5, the second electrodes 408 in FIGS. 4A to 4D correspond to data lines 508 in FIG. 5, and the partitions 406 in FIGS. 4A to 4D correspond to partitions 506 in FIG. 5. An EL layer is formed between the data line 508 and the scan line 503, and a region 505 corresponds to one pixel.

Note that the scan lines 503 are electrically connected at their ends to connection wirings 509, and the connection wirings 509 are connected to an FPC 511b through an input terminal 510. The data lines 508 are connected to an FPC 511a through an input terminal 512.

For example, a surface where light is extracted may be provided with an optical film such as a polarizing plate, a circularly polarizing plate (including an elliptically polarizing plate), a retardation plate (a λ/4 plate or a λ/2 plate), a color filter, or an anti-reflection film. In addition, the surface where light is extracted or a surface of the various films may be subjected to treatment. For example, when a surface is provided with slight projection and depression, reflected light diffuses to reduce glare.

Note that although FIG. 5 illustrates the example in which an IC chip including a driver circuit is not provided over the substrate, an IC chip may be mounted on the substrate. As a method for mounting an IC chip, a COG method, a wire bonding method, TCP, or the like can be used.

Figure 6A:
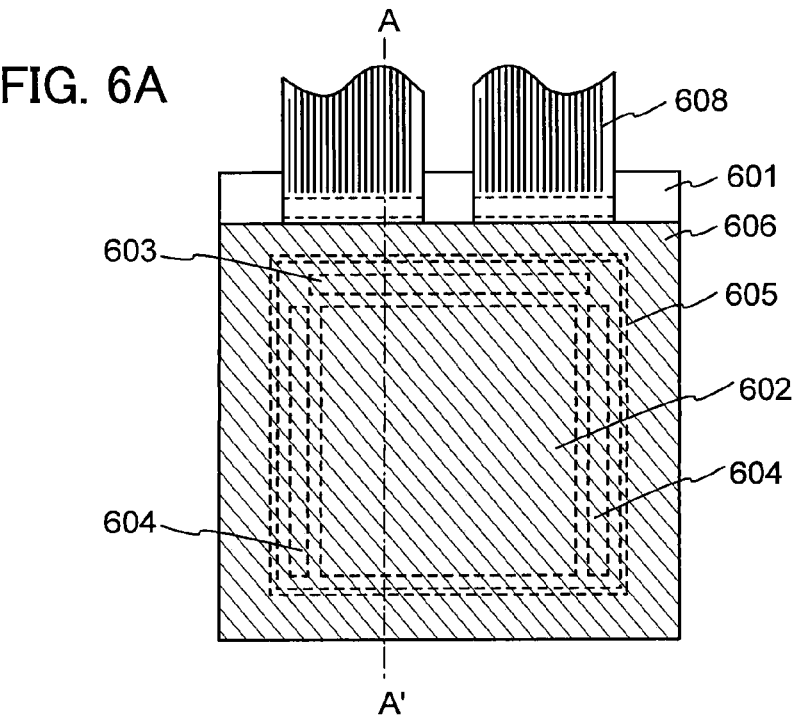
FIGS. 6A and 6B are views illustrating an active matrix light-emitting device.
Figure 6B:
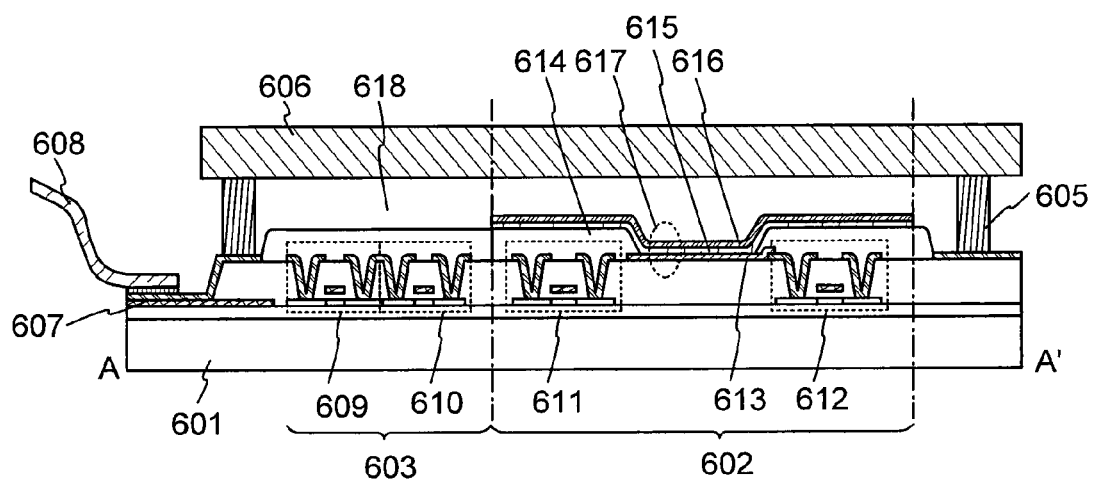

FIGS. 6A and 6B illustrate an example of an active matrix light-emitting device.

FIG. 6A is a top view of the light-emitting device. FIG. 6B is a cross-sectional view taken along dashed line A-A' in FIG. 6A.

The active matrix light-emitting device of this embodiment includes a pixel portion 602, a driver circuit portion 603 (a source side driver circuit), and a driver circuit portion 604 (a gate side driver circuit) which are provided over an element substrate 601. The pixel portion 602, the driver circuit portion 603, and the driver circuit portion 604 are sealed with a sealing material 605 between the element substrate 601 and a sealing substrate 606 (see FIG. 6A).

In addition, over the element substrate 601, a lead wiring 607 for connecting an external input terminal is provided. Note that an example is described here in which an FPC is provided as the external input terminal. Although only the FPC 608 is illustrated in FIGS. 6A and 6B, this FPC may be provided with a printed wiring board (PWB). The "light-emitting device" in this specification and the like includes not only a light-emitting device body but also a light-emitting device to which an FPC, a PWB, or the like is attached.

In the driver circuit portion 603, a CMOS circuit which is a combination of an n-channel TFT 609 and a p-channel TFT 610 is formed (see FIG. 6B). Needless to say, the circuit configuration is not limited to this example, and any of a variety of circuits such as CMOS circuits, PMOS circuits, or NMOS circuits can be applied. In addition, although a driver circuit-integrated type where the driver circuit is formed over the substrate is described in this embodiment, the present invention is not to be construed as being limited to this structure. The driver circuit can be formed outside. Note that FIG. 6B illustrates just the driver circuit portion 603 which is the source side driver circuit and the pixel portion 602 as an example.

The pixel portion 602 has plural pixels, each of which includes a switching TFT 611, a current control TFT 612, and an anode 613 which is electrically connected to an electrode (a source or drain electrode) of the current control TFT 612.

Note that an insulator 614 is formed so as to cover the edge portion of the anode 613. Further, for the insulator 614, either a negative photosensitive material which becomes insoluble in an etchant by light or a positive photosensitive material which becomes soluble in an etchant by light can be used. Without limitation to an organic compound, an inorganic compound such as silicon oxide or silicon oxynitride can be used.

An upper edge portion or a lower edge portion of the insulator 614 is preferably a curved surface having a specific curvature radius. The curved surface contributes to improvement of coverage by a film which is to be formed over the insulator 614. For example, when a positive photosensitive acrylic resin is used as a material for the insulator 614, the upper edge portion thereof is preferably formed as a curved surface having a curvature radius of 0.2 μm to 3 μm.

Over the anode 613, an EL layer 615 and a cathode 616 are stacked. Here, when an ITO film is applied to the anode 613, a stack of a titanium nitride film and a film containing aluminum as its main component or a stack of a titanium nitride film, a film containing aluminum as its main component, and a titanium nitride film is applied to a wiring of the current control TFT 612 which is connected to the anode 613, ohmic contact with the ITO film can be obtained, and resistance of the wiring can be kept low. Note that, although not illustrated in FIGS. 6A and 6B, the cathode 616 is electrically connected to an FPC 608 which is an external input terminal.

Note that at least a light-emitting layer is provided in the EL layer 615. In addition to the light-emitting layer, a hole-injecting layer, a hole-transporting layer, an electron-transporting layer, an electron-injecting layer, and/or the like may be provided. The anode 613, the EL layer 615, and the cathode 616 are stacked to form a light-emitting element 617.

In addition, although one light-emitting element 617 is illustrated in the cross-sectional view of FIG. 6B, a plurality of light-emitting elements are arranged in matrix in the pixel portion 602. Further, full-color display can be achieved by providing light-emitting elements that emit light of three colors (R, G, and B) as selected in the pixel portion 602. Color filters may be used in combination to perform full-color display.

The light-emitting element 617 is provided in a space 618 surrounded by the element substrate 601, the sealing substrate 606, and the sealing material 605. Note that the space 618 may be filled with an inert gas (nitrogen, argon, or the like) or any other material such as the sealing material 605.

An epoxy-based resin is preferably used for the sealing material 605. As a material used for these, a material that allows as little moisture or oxygen as possible to permeate. As the element substrate 601 or the sealing substrate 606, a plastic substrate formed of fiberglass-reinforced plastics (FRP), polyvinyl fluoride (PVF), polyester, acrylic, or the like can be used as well as a glass substrate or a quartz substrate.

Note that this embodiment can be used in appropriate combination with any of the structures described in the above embodiments.

Embodiment 6

In Embodiment 6, examples of a variety of electronic devices and lighting devices that are completed using the light-emitting device which is an embodiment of the present invention will be described with reference to FIGS. 7A to 7E and FIG. 8.

Examples of the electronic devices to which the light-emitting device is applied include television sets (also referred to as televisions or television receivers), monitors of computers or the like, cameras such as digital cameras or digital video cameras, digital photo frames, cellular phones (also referred to as cellular phones or cellular phone sets), portable game consoles, portable information terminals, audio reproducing devices, large-sized game machines such as pachinko machines, and the like. Specific examples of these electronic devices and lighting device are illustrated in FIGS. 7A to 7E.

Figure 7A:
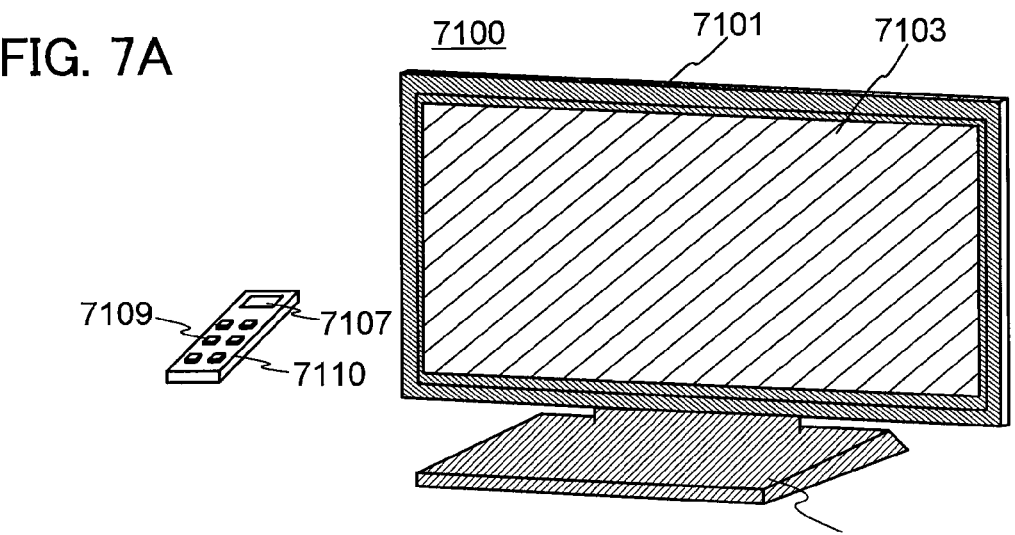
FIGS. 7A to 7E are views each illustrating an electronic device.

FIG. 7A illustrates an example of a television device. In a television device 7100, a display portion 7103 is incorporated in a housing 7101. Images can be displayed by the display portion 7103, and the light-emitting device can be used for the display portion 7103. In addition, here, the housing 7101 is supported by a stand 7105.

The television device 7100 can be operated with an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device 7100 is provided with a receiver, a modem, and the like. Moreover, when the display device is connected to a communication network with or without wires via the modem, one-way (from a sender to a receiver) or two-way (between a sender and a receiver or between receivers) information communication can be performed.

Figure 7B:
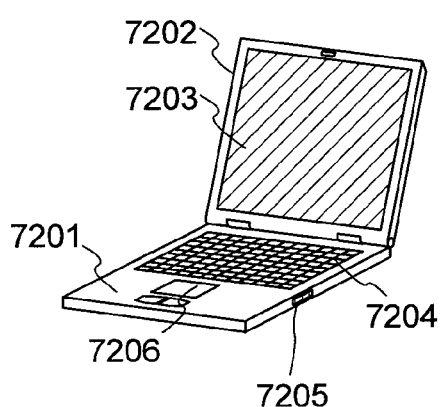

FIG. 7B illustrates an example of a computer. This computer includes a main body 7201, a housing 7202, a display portion 7203, a keyboard 7204, an external connecting port 7205, a pointing device 7206, and the like. This computer is manufactured by using a light-emitting device for the display portion 7203.

Figure 7C:
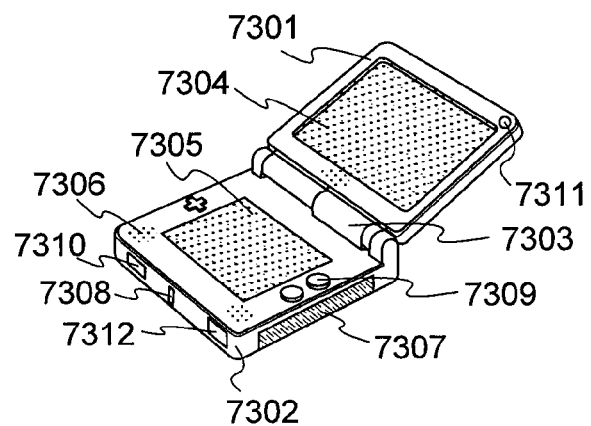

FIG. 7C illustrates an example of a portable amusement machine. This portable amusement machine includes two housings: a housing 7301 and a housing 7302. The housings 7301 and 7302 are connected with a connection portion 7303 so as to be opened and closed. A display portion 7304 is incorporated in the housing 7301, and a display portion 7305 is incorporated in the housing 7302. In addition, the portable amusement machine illustrated in FIG. 7C includes a speaker portion 7306, a recording medium insertion portion 7307, an LED lamp 7308, an input means (an operation key 7309, a connection terminal 7310, a sensor 7311 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, tilt angle, vibration, smell, or infrared rays), or a microphone 7312), and the like. Needless to say, the structure of the portable amusement machine is not limited to the above structure as long as the light-emitting device is used for at least either the display portion 7304 or the display portion 7305, or both of them. The portable amusement machine illustrated in FIG. 7C has a function of reading a program or data stored in a recording medium to display it on the display portion, and a function of sharing information with another portable amusement machine by wireless communication. The portable game machine illustrated in FIG. 7C can have a variety of functions without limitation to the above.

Figure 7D:
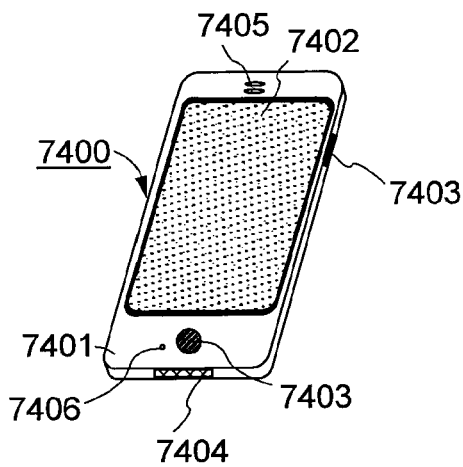

FIG. 7D illustrates an example of a cellular phone. A cellular phone 7400 is provided with a display portion 7402 incorporated in a housing 7401, operation buttons 7403, an external connection port 7404, a speaker 7405, a microphone 7406, and the like. Note that the light-emitting device is used for the display portion 7402 of the cellular phone 7400.

When the display portion 7402 of the cellular phone 7400 illustrated in FIG. 7D is touched with a finger or the like, data can be input into the cellular phone 7400. Furthermore, operations such as making calls and composing mails can be performed by touching the display portion 7402 with a finger or the like.

There are mainly three screen modes for the display portion 7402. The first mode is a display mode mainly for displaying images. The second mode is an input mode mainly for inputting data such as text. The third mode is a display-and-input mode in which two modes of the display mode and the input mode are combined.

For example, for operations such as making calls and composing mails, the display portion 7402 is set to a text input mode (second mode) mainly for inputting text so that text can be input. In this case, a keyboard or number buttons are preferably displayed on the display portion 7402.

When a detection device which includes a sensor for detecting inclination, such as a gyroscope or an acceleration sensor, is provided inside the cellular phone 7400, the direction of the cellular phone 7400 is determined so that display on the screen of the display portion 7402 can be automatically switched.

In addition, the screen mode is switched by, for example, touching the display portion 7402 or operating the operation buttons 7403 of the housing 7401. Alternatively, the screen mode may be switched depending on the kind of images displayed on the display portion 7402. For example, when a signal of an image to be displayed on the display portion is of moving image data, the screen mode is switched to the display mode (first mode). When the signal is of text data, the screen mode is switched to the input mode (second mode).

Furthermore, when input by touching the display portion 7402 is not performed for a certain period, a controlling operation may be performed: for example, the screen mode may be switched from the input mode (first mode) to the display mode (second mode).

The display portion 7402 may function as an image sensor. For example, an image of a palm print, a fingerprint, or the like is taken by touching the display portion 7402 with the palm or the finger, whereby personal authentication can be performed. Further, when a backlight or a sensing light source which emits a near-infrared light is provided in the display portion, an image of a finger vein, a palm vein, or the like can be taken.

Figure 7E:
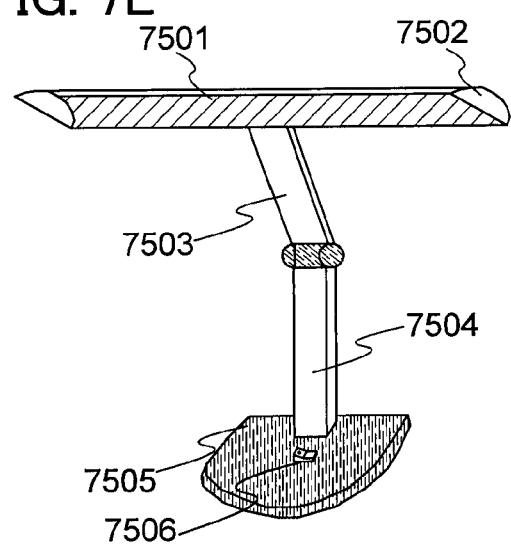

FIG. 7E illustrates a desk lamp including a lighting portion 7501, a shade 7502, an adjustable arm 7503, a support 7504, a base 7505, and a power supply 7506. The desk lamp is manufactured using a light-emitting device for the lighting portion 7501. Note that the lighting equipment includes a ceiling light, a wall light, and the like.

Figure 8:
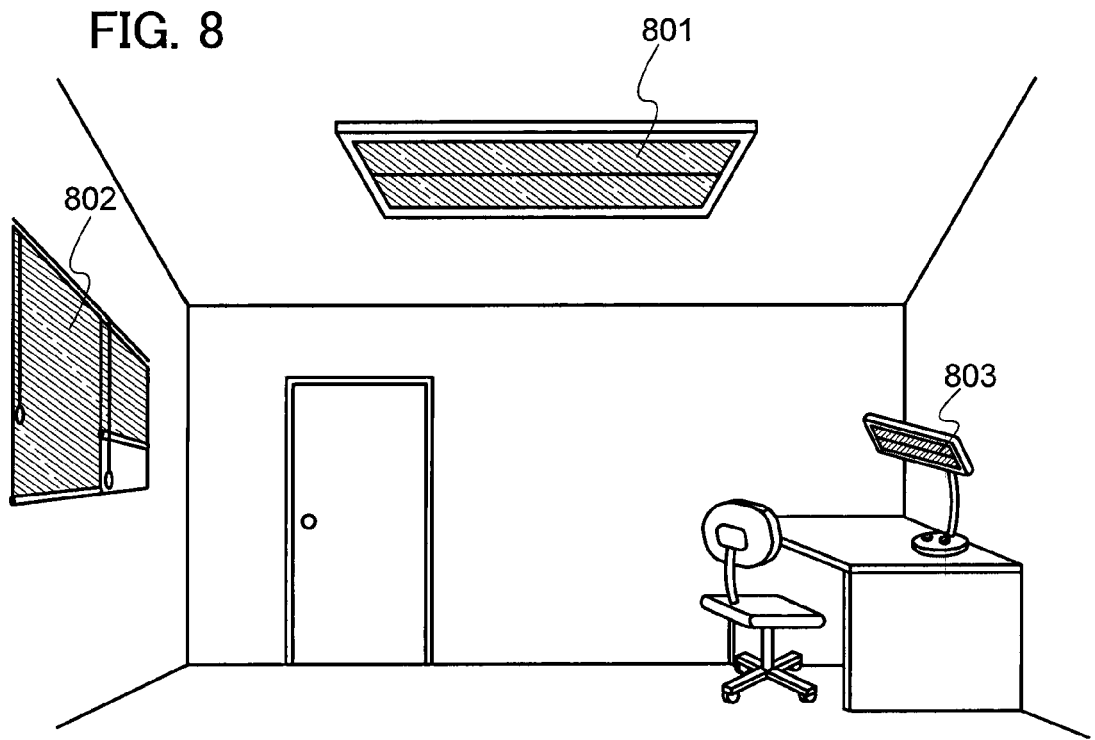
FIG. 8 is a view illustrating lighting devices.

FIG. 8 illustrates an example in which the light-emitting device is used for an indoor lighting device 801. The light-emitting device enables an increase in emission area, and therefore can be used as a large-sized lighting device. Furthermore, the light-emitting device may be used as a lighting device 802 which can be rolled up. In addition, a desk lamp 803 illustrated in FIG. 7E may be used together in the room provided with the interior lighting device 801.

The electronic devices, lighting devices, and the like as illustrated above can be provided by application of the light-emitting device described in the above embodiment, for example. Thus, the applicable range of the light-emitting device is wide so that the light-emitting device can be applied to electronic devices in a variety of fields.

Note that this embodiment can be used in appropriate combination with any of the structures described in the above embodiments.

Example 1

In Example 1, an example of a synthesis method of 4-(benzo[d]oxazol-2-yl)-4'-(9H-carbazol-9-yl)triphenylamine (abbreviation: YGABOx) which is represented by a structural formula (165) will be described.

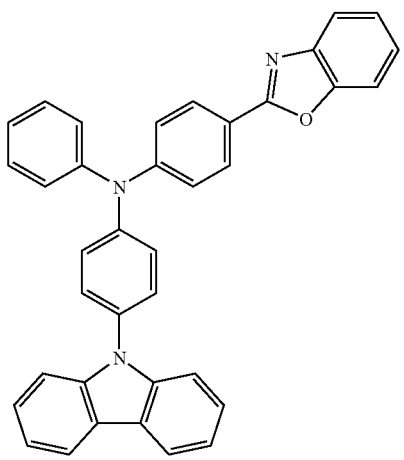

(165)

A synthesis scheme is shown in the following (E1-1).

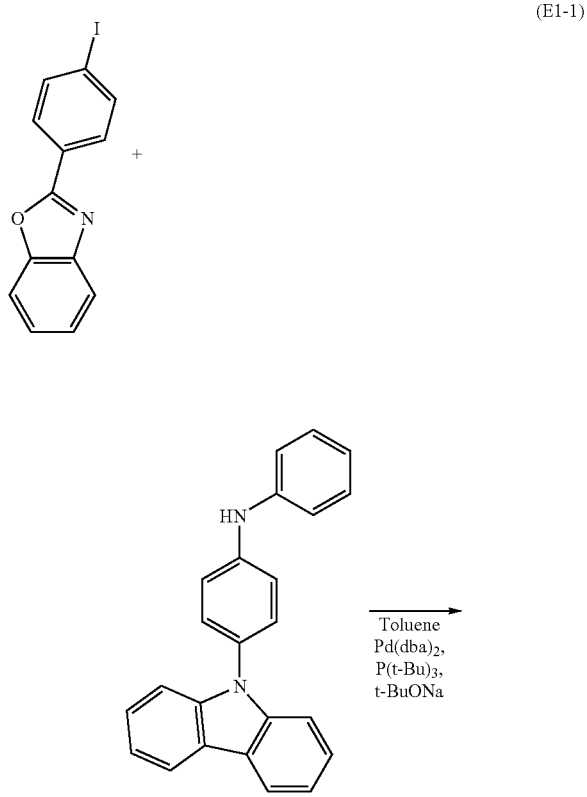

(E1-1)

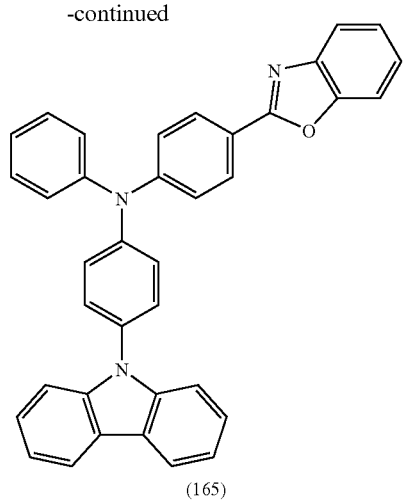

(165)

In a 100 mL three-necked flask were placed 1.0 g (3.1 mmol) of 2-(4-iodophenyl)benzo[d]oxazole, 1.0 g (3.1 mmol) of 4-(9H-carbazol-9-yl)diphenylamine, and 0.66 g (6.9 mmol) of sodium tert-butoxide, and the atmosphere in the flask was replaced with nitrogen. To this mixture were added 10 mL of toluene and 0.10 mL of a 10% hexane solution of tri(tert-butyl)phosphine. This mixture was degassed by reducing the pressure in the flask. After that, the atmosphere in the flask was replaced with nitrogen.

To this mixture was added 0.050 g (0.087 mmol) of bis(dibenzylideneacetone)palladium(0), followed by stirring under a nitrogen stream at 80° C. for 3 hours. After the stirring, toluene was added to this mixture, and this suspension was subjected to suction filtration through Celite (produced by Wako Pure Chemical Industries, Ltd., Catalog No. 531-16855) to give a filtrate. The obtained filtrate was washed with a saturated sodium hydrogen carbonate solution and a saturated saline solution. After that, the organic layer was dried by addition of magnesium sulfate. After the drying, this mixture was subjected to suction filtration to give a filtrate. The obtained filtrate was concentrated to give a solid. The obtained solid was dissolved in toluene and purified by silica gel column chromatography. The silica gel column chromatography was performed using toluene as a developing solvent. The obtained fraction was concentrated to give a solid. This solid was recrystallized with a mixed solvent of chloroform and methanol to give 1.4 g of a light yellow powdered solid in a yield of 88%.

In addition, 1.4 g of the obtained solid was sublimated and purified by train sublimation. The sublimation purification was performed under a reduced pressure of 7.0 Pa, with a flow rate of argon at 3.0 mL/min, at 240° C., and for 16 hours. After the sublimation purification, 0.50 g of a target substance was obtained in a yield of 36%.

By a nuclear magnetic resonance (NMR) method, this compound was confirmed to be 4-(benzo[d]oxazol-2-yl)-4'-(9H-carbazol-9-yl)triphenylamine (abbreviation: YGABOx).

$^1$H NMR data of the obtained compound is shown below: $^1$H NMR (CDCl$_3$, 300 MHz): δ=4.17-7.52 (m, 19H), 7.54-7.59 (m, 1H), 7.73-7.77 (m, 1H), 8.15 (d, j=8.3 Hz, 4H)

Figure 9A:
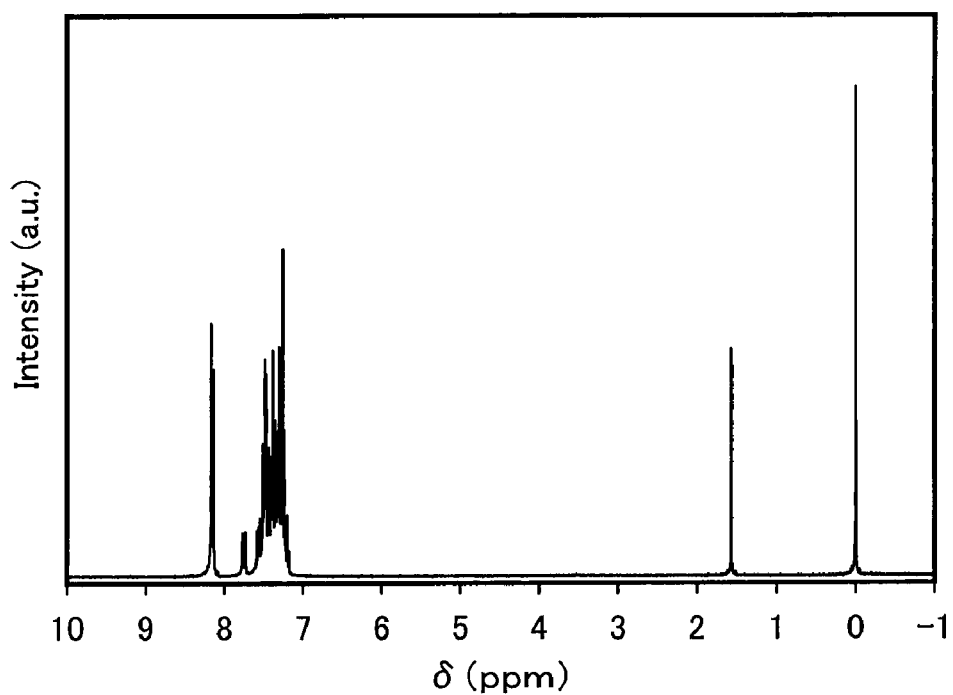
FIGS. 9A and 9B are $^1$H NMR charts of YGABOx (abbreviation)
Figure 9B:
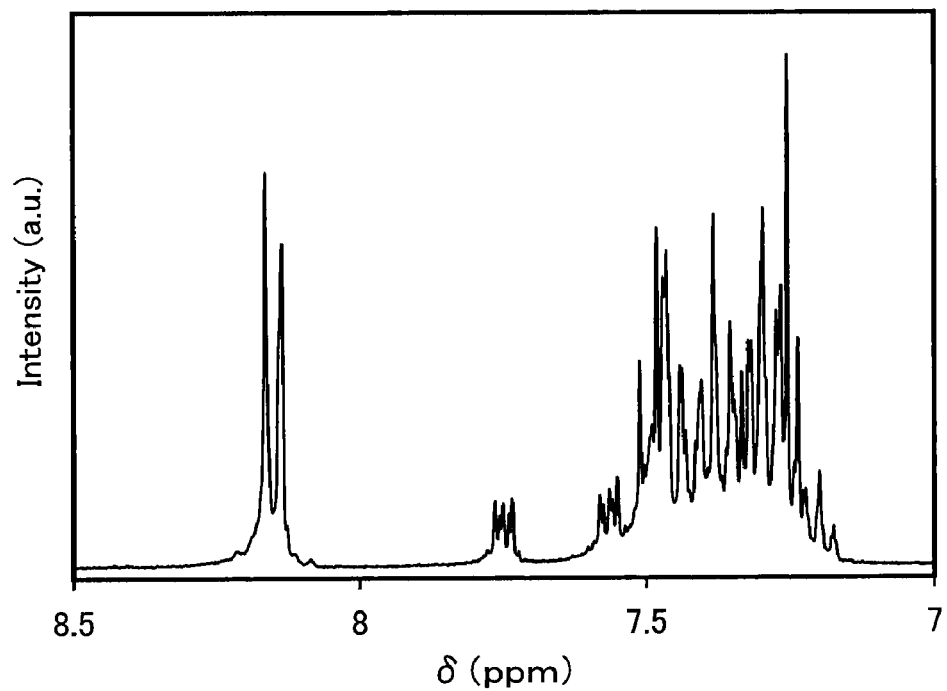

$^1$H-NMR charts are shown in FIGS. 9A and 9B. Note that FIG. 9B is a chart in which the range of 7.0 ppm to 8.5 ppm in FIG. 9A is enlarged.

Figure 10A:
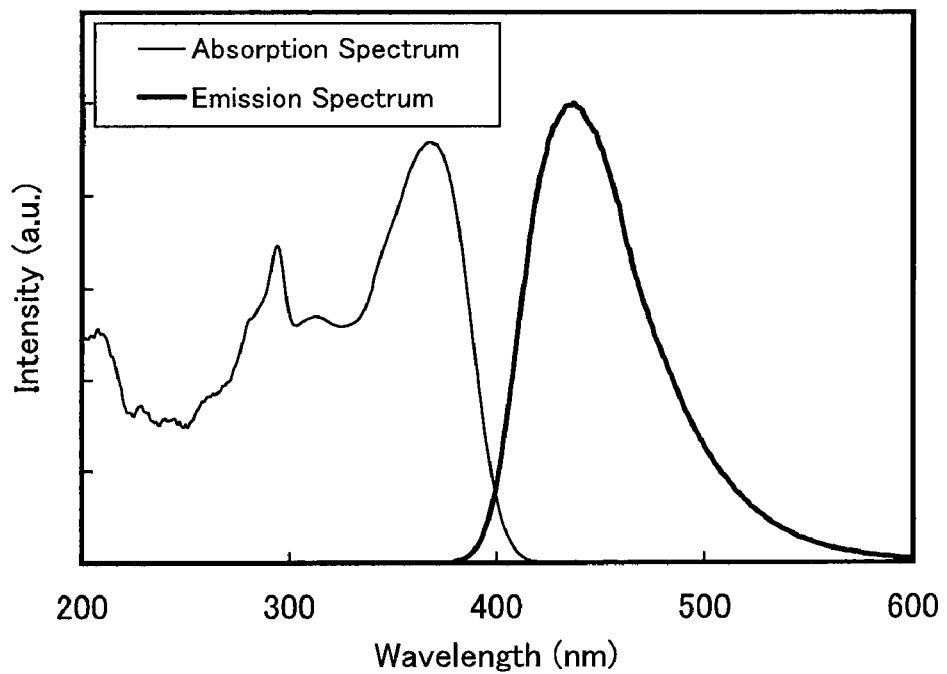
FIGS. 10A and 10B are graphs each showing absorption and emission spectra of YGABOx (abbreviation)
Figure 10B:
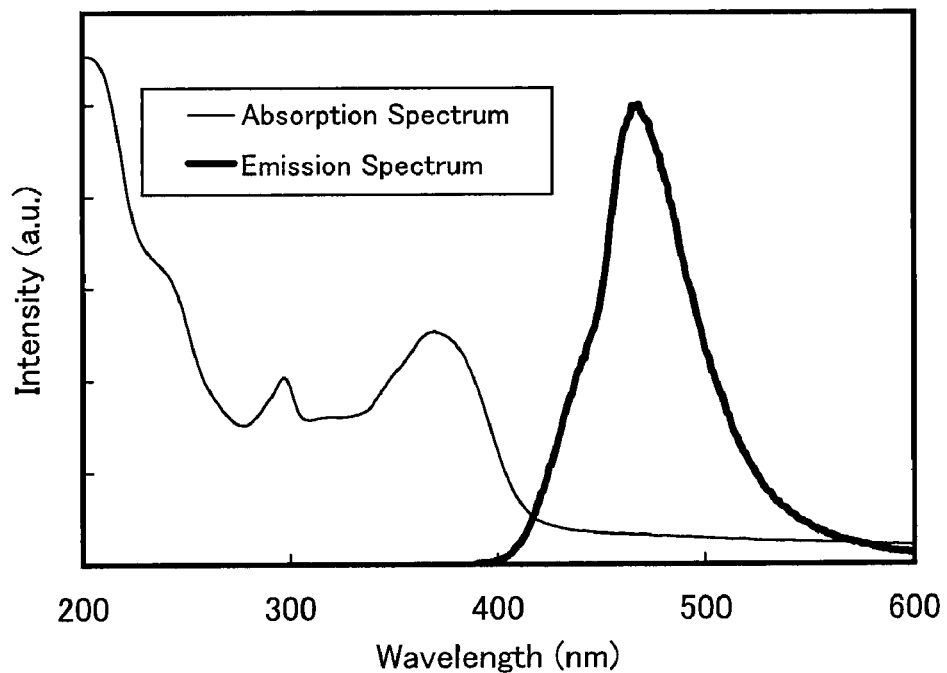

FIG. 10A shows an absorption spectrum and an emission spectrum of YGABOx in a toluene solution. FIG. 10B shows an absorption spectrum and an emission spectrum of YGA-BOx in a thin-film form. The measurement of the absorption spectra was performed using an ultraviolet-visible spectrophotometer (V-550, manufactured by JASCO Corporation). As for samples for the measurement, the solution was put into a quartz cell and the thin film was obtained by evaporation of YGABOx onto a quartz substrate. The absorption spectrum of YGABOx in the solution, which is shown in FIG. 10A, was obtained by subtraction of the absorption spectra of the quartz cell and toluene from the raw absorption spectra. The absorption spectrum of YGABOx in the thin-film form, which is shown in FIG. 10B, was obtained by subtraction of the absorption spectrum of the quartz substrate from the raw absorption spectra. In FIGS. 10A and 10B, the horizontal axis represents wavelength (nm) and the vertical axis represents intensity (arbitrary unit). In the case of YGABOx in the toluene solution, the maximum point of the absorption was observed at about 366 nm, and the maximum emission wavelength was 440 nm (excitation wavelength: 373 nm). In the case of YGABOx in the thin-film form, the absorption was observed at about 370 nm, and the maximum emission wavelength was 467 nm (excitation wavelength: 376 nm).

The HOMO level and the LUMO level of YGABOx in the thin-film form were measured. The HOMO level was obtained by converting the ionization potential in air, which was measured by photoelectron spectrometer (AC-2, manufactured by Riken Keiki Co., Ltd.), into a negative value. In addition, the LUMO level was obtained in such a manner that the absorption edge was obtained from Tauc plot, with an assumption of direct transition, using data on the absorption spectrum of the thin film of YGABOx in FIG. 10B, and the absorption edge was added to the HOMO level as an optical energy gap. Accordingly, the HOMO level, energy gap, and LUMO level of YGABOx were −5.56 eV, 3.06 eV, and −2.50 eV, respectively.

Thus, it was found that YGABOx has a large energy gap over 3.00 eV.

Further, the optimal molecular structure of YGABOx in the ground state was calculated using the density functional theory (DFT). In the DFT, the total energy is represented as the sum of potential energy, electrostatic energy between electrons, electronic kinetic energy, and exchange-correlation energy including all the complicated interactions between electrons. Also in the DFT, an exchange-correlation interaction is approximated by a functional (a function of another function) of one electron potential represented in terms of electron density; thus, high-speed and high-accuracy calculation is obtained. Here, B3LYP, which is a hybrid functional, was used to specify the weight of each parameter related to exchange-correlation energy. In addition, as a basis function, 6-311 (a basis function of a triple-split valence basis set using three contraction functions for each valence orbital) was applied to all the atoms. By the above basis function, for example, orbits of 1s to 3s are considered in the case of hydrogen atoms while orbits of 1 s to 4s and 2p to 4p are considered in the case of carbon atoms. Furthermore, for improvement of the calculation accuracy, the p function and the d function as polarization basis sets were added respectively to hydrogen atoms and atoms other than hydrogen atoms.

Note that Gaussian 03 was used as a quantum chemistry computational program. A high performance computer (Altix 4700, manufactured by SGI Japan, Ltd., was used for the calculations.

Figure 32A:
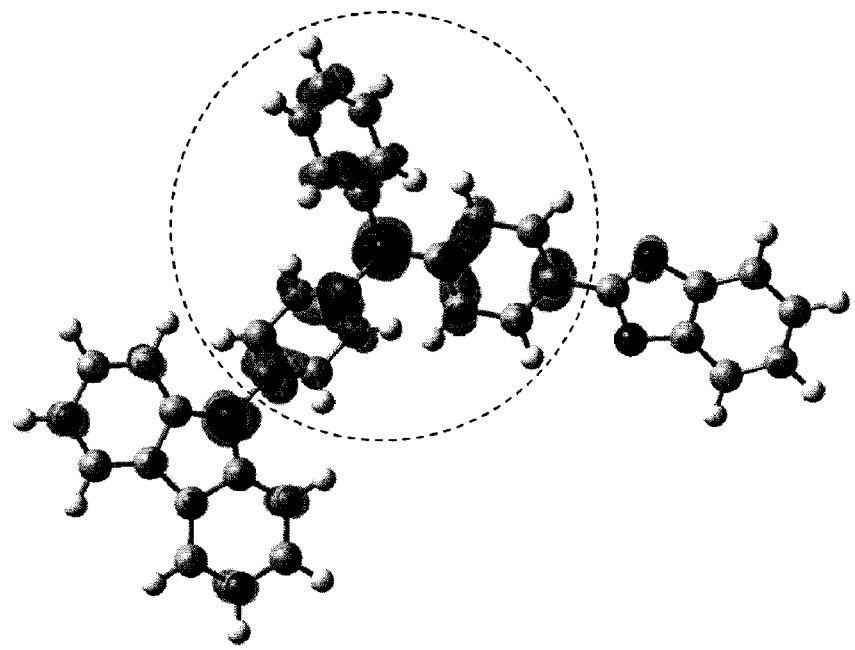
FIGS. 32A and 32B are views showing the highest occupied molecular orbital and lowest unoccupied molecular orbital of YGABOx which were obtained by calculation.
Figure 32B:
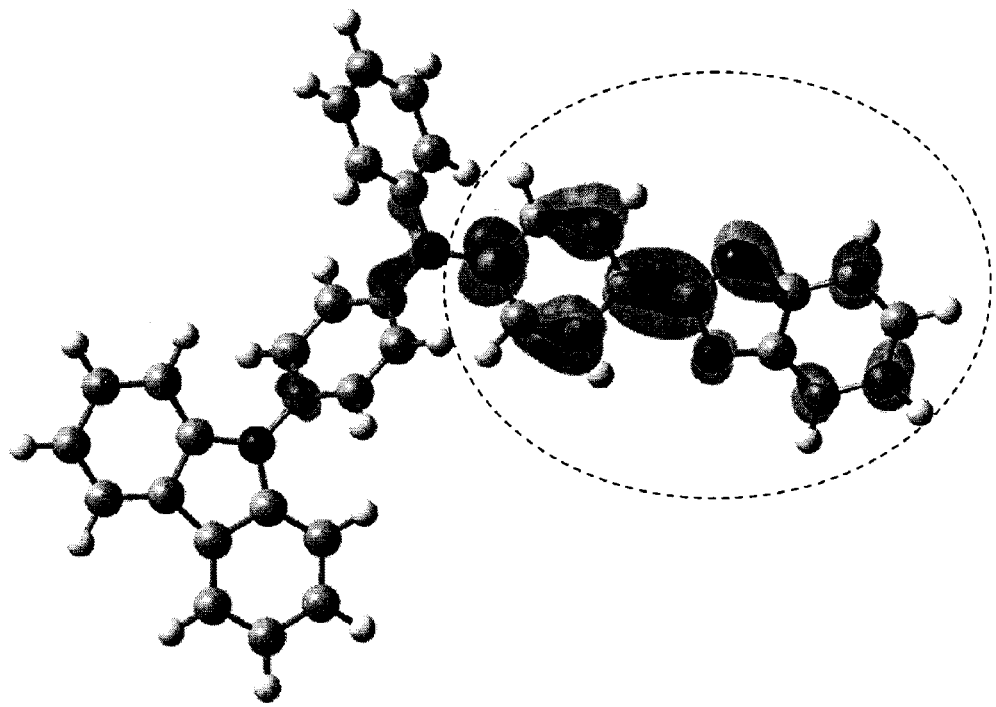

The highest occupied molecular orbital (HOMO) and lowest unoccupied molecular orbital (LUMO) of YGABOx in a suitable molecular structure which were obtained by the calculations, were visualized by Gauss View 4.1 to be shown in FIGS. 32A and 32B. FIG. 32A shows the highest occupied molecular orbital (HOMO), and FIG. 32B shows the lowest unoccupied molecular orbital (LUMO). In FIGS. 32A and 32B, the spheres represent atoms forming YGABOx and cloud-like objects around the atoms represent the highest occupied molecular orbital (HOMO) and the lowest unoccupied molecular orbital (LUMO).

According to FIGS. 32A and 32B, the highest occupied molecular orbital exists near amine, which shows that an amino group greatly contributes to the hole-transporting property of YGABOx. In addition, the lowest occupied molecular orbital exists near benzoxazole, which shows that a benzoxazolyl group greatly contributes to the electron-transporting property of YGABOx. Thus, a benzoxazole skeleton having an electron-transporting property, which is a hetero aromatic ring, and an amine skeleton having a hole-transporting property are introduced in a molecule. Accordingly, it is found that YGABOx is a bipolar material having electron- and hole-transporting properties.

Example 2

In Example 2, an example of a synthesis method of 4-(imidazo[1,2-a]pyridine-2-yl)-4'-(9H-carbazol-9-yl)triphenylamine (abbreviation: YGAPIM) which is represented by a structural formula (146) will be described.

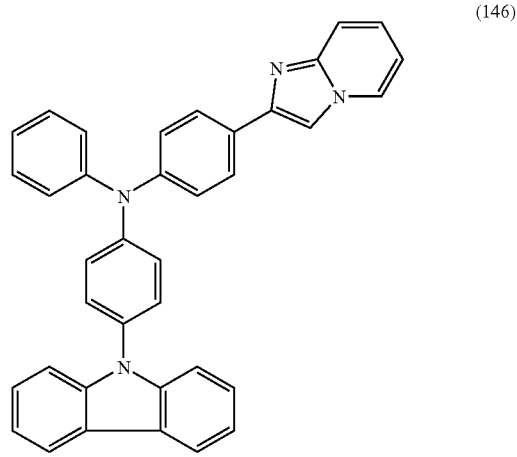

(146)

A synthesis scheme is shown in the following (E2-1).

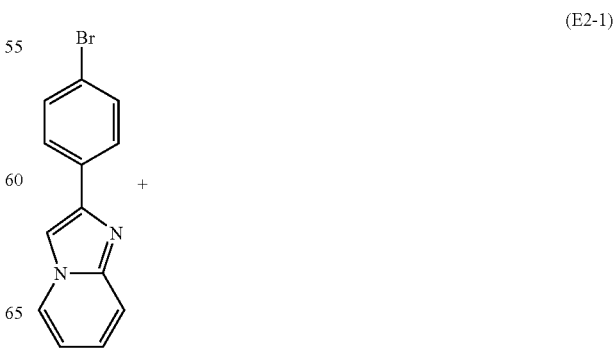

(E2-1)

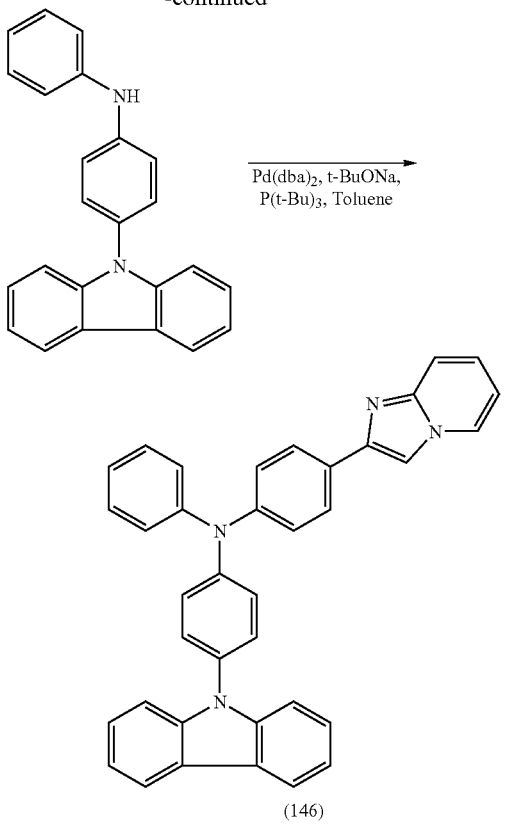

(146)

In a 100 mL three-necked flask were placed 1.0 g (3.7 mmol) of 2-(4-bromophenyl)imidazo[1,2-a]pyridine, 0.82 g (8.5 mmol) of sodium tert-butoxide, 1.2 g (3.7 mmol) of 9-[4-(N-phenylamino)phenyl]carbazole (abbreviation: YGA), and 0.10 g (0.17 mmol) of bis(dibenzylideneacetone)palladium(0), and the atmosphere in the flask was replaced with nitrogen. To this mixture were added 20 mL of toluene and 0.1 mL of a 10% hexane solution of tri(tert-butyl)phosphine. This mixture was stirred under a nitrogen stream at 120° C. for 5 hours.

After the stirring, chloroform was added to this mixture, followed by suction filtration through Celite (produced by Wako Pure Chemical Industries, Ltd., Catalog No. 531-16855), Florisil (produced by Wako Pure Chemical Industries, Ltd., Catalog No. 540-00135), and alumina to give a filtrate. The obtained filtrate was washed with water and a saturated saline solution in this order, and then the organic layer was dried with magnesium sulfate. After the drying, the mixture was subjected to suction filtration to give a filtrate. The obtained filtrate was concentrated to give a compound. The obtained compound was purified by silica gel column chromatography. The silica gel column chromatography was performed using toluene as a developing solvent. The obtained fraction was concentrated to give a solid. This solid was recrystallized with a mixed solvent of chloroform and hexane to give 1.4 g of a light yellow powdered solid in a yield of 72%.

In addition, 1.4 g of the obtained solid was sublimated and purified by train sublimation. The sublimation purification was performed under a reduced pressure of 7.0 Pa, with a flow rate of argon at 3.0 mL/min, at 300° C., and for 15 hours. After the sublimation purification, 1.1 g of a target substance was obtained in a yield of 79%.

By a nuclear magnetic resonance (NMR) method, this compound was confirmed to be 4-(imidazo[1,2-a]pyridine-2-yl)-4'-(9H-carbazol-9-yl)triphenylamine (abbreviation: YGAPIM), which was a target substance.

$^1$H NMR data of the obtained compound is shown below: $^1$H NMR (CDCl$_3$, 300 MHz): δ=6.79 (t, J=6.4 Hz, 1H), 7.07-7.49 (m, 18H), 7.65 (d, J=9.3 Hz, 1H), 7.82 (s, 1H), 7.91 (d, J=7.8 Hz, 2H), 8.09-8.16 (m, 3H)

Figure 11A:
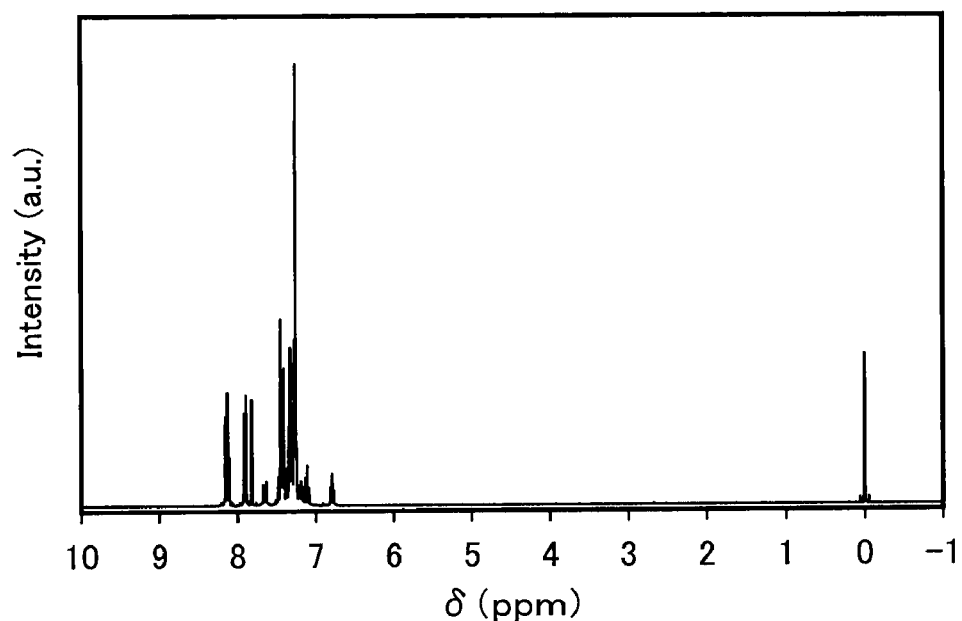
FIGS. 11A and 11B are $^1$H NMR charts of YGAPIM (abbreviation)
Figure 11B:
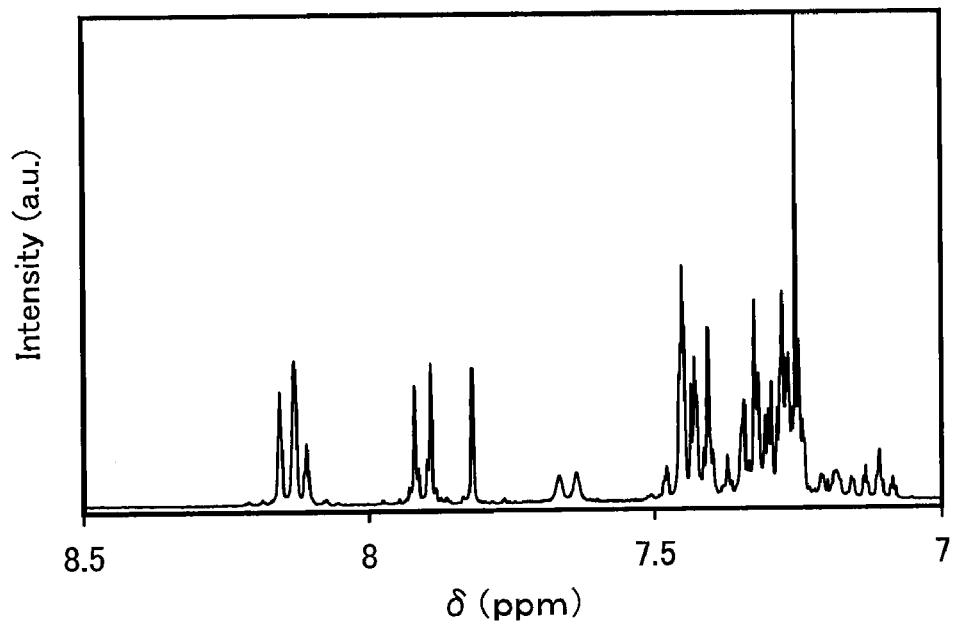

$^1$H-NMR charts are shown in FIGS. 11A and 11B. Note that FIG. 11B is a chart in which the range of 7.0 ppm to 8.5 ppm in FIG. 11A is enlarged.

Figure 12A:
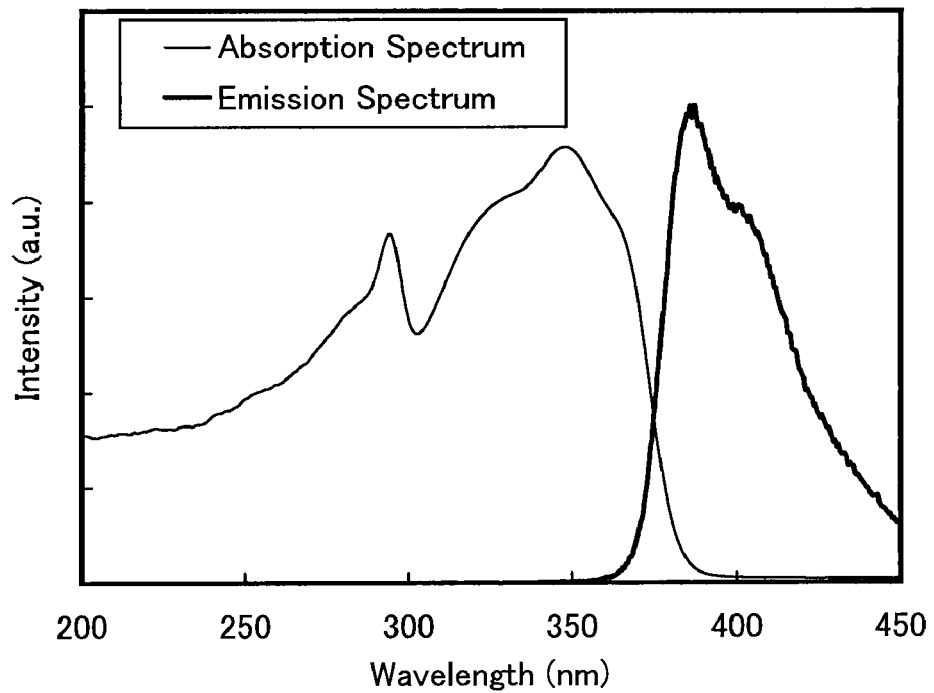
FIGS. 12A and 12B are graphs each showing absorption and emission spectra of YGAPIM (abbreviation)
Figure 12B:
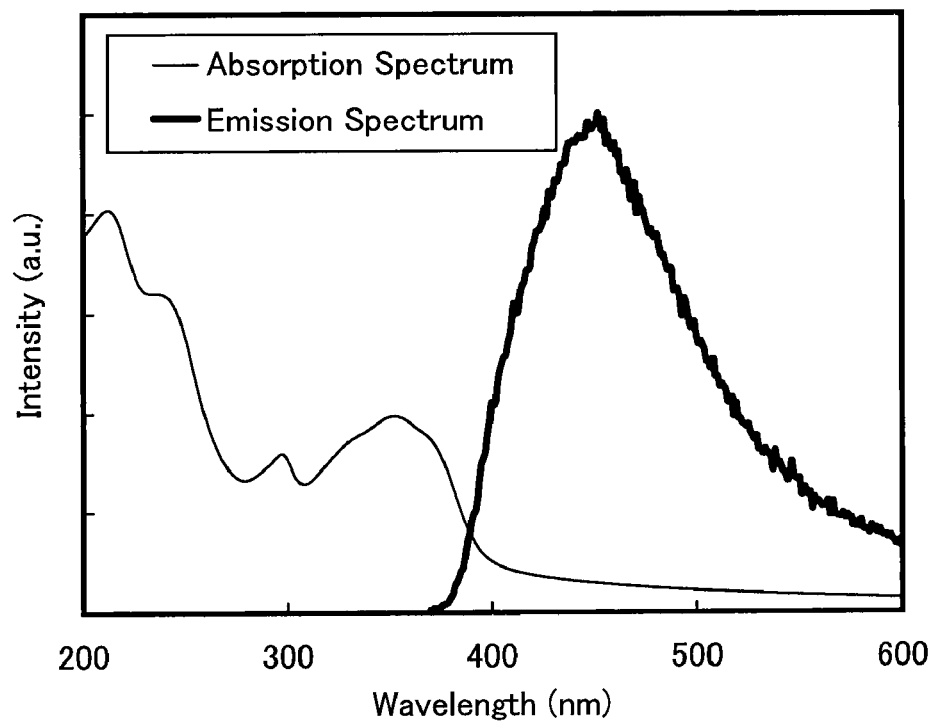

FIG. 12A shows an absorption spectrum and an emission spectrum of YGAPIM in a toluene solution. FIG. 12B shows an absorption spectrum and an emission spectrum of YGAPIM in a thin-film form. The measurement of the absorption spectra was performed using an ultraviolet-visible spectrophotometer (V-550, manufactured by JASCO Corporation). As for the samples for the measurement, the solution was put into a quartz cell and the thin film was obtained by evaporation of YGAPIM onto a quartz substrate. The absorption spectrum of YGAPIM in the solution, which is shown in FIG. 12A, was obtained by subtraction of the absorption spectra of the quartz cell and toluene from the raw absorption spectra. The absorption spectrum of YGAPIM in the thin-film form, which is shown in FIG. 12B, was obtained by subtraction of the absorption spectrum of the quartz substrate from the raw absorption spectra. In FIGS. 12A and 12B, the horizontal axis represents wavelength (nm) and the vertical axis represents intensity (arbitrary unit). In the case of YGAPIM in the toluene solution, the absorption was observed at about 361 nm, and the maximum emission wavelengths were 387 nm and 402 nm (excitation wavelength: 332 nm). In the case of YGAPIM in the thin-film form, the absorption was observed at about 352 nm, and the maximum emission wavelength was 452 nm (excitation wavelength: 352 nm).

The HOMO level and the LUMO level of YGAPIM in the thin-film form were measured. The HOMO level was obtained by converting the ionization potential in air, which was measured by photoelectron spectrometer (AC-2, manufactured by Riken Keiki Co., Ltd.), into a negative value. In addition, the LUMO level was obtained in such a manner that the absorption edge was obtained from Tauc plot, with an assumption of direct transition, using data on the absorption spectrum of the thin film of YGAPIM in FIG. 12B, and the absorption edge was added to the HOMO level as an optical energy gap. Accordingly, the HOMO level, energy gap, and LUMO level of YGAPIM were −5.33 eV, 3.17 eV, and −2.16 eV, respectively.

Thus, it was found that YGAPIM has a large energy gap.

Further, the optimal molecular structure of YGAPIM in the ground state was calculated using the density functional theory (DFT). In the DFT, the total energy is represented as the sum of potential energy, electrostatic energy between electrons, electronic kinetic energy, and exchange-correlation energy including all the complicated interactions between electrons. Also in the DFT, an exchange-correlation interaction approximates a functional (a function of another function) of one electron potential expressed as electron density; thus, high-speed and high-accuracy calculation is obtained. Here, B3LYP, which is a hybrid functional, was used to specify the weight of each parameter related to exchange-correlation energy. In addition, as a basis function, 6-311 (a basis function of a triple-split valence basis set using three contraction functions for each valence orbital) was applied to all the atoms. By the above basis function, for example, orbits of 1s to 3s are considered in the case of hydrogen atoms while orbits of 1 s to 4s and 2p to 4p are considered in the case of carbon atoms. Furthermore, for improvement of the calculation accuracy, the p function and the d function as polarization basis sets were added respectively to hydrogen atoms and atoms other than hydrogen atoms.

Note that Gaussian 03 was used as a quantum chemistry computational program. A high performance computer (Altix 4700, manufactured by SGI Japan, Ltd., was used for the calculations.

Figure 33A:
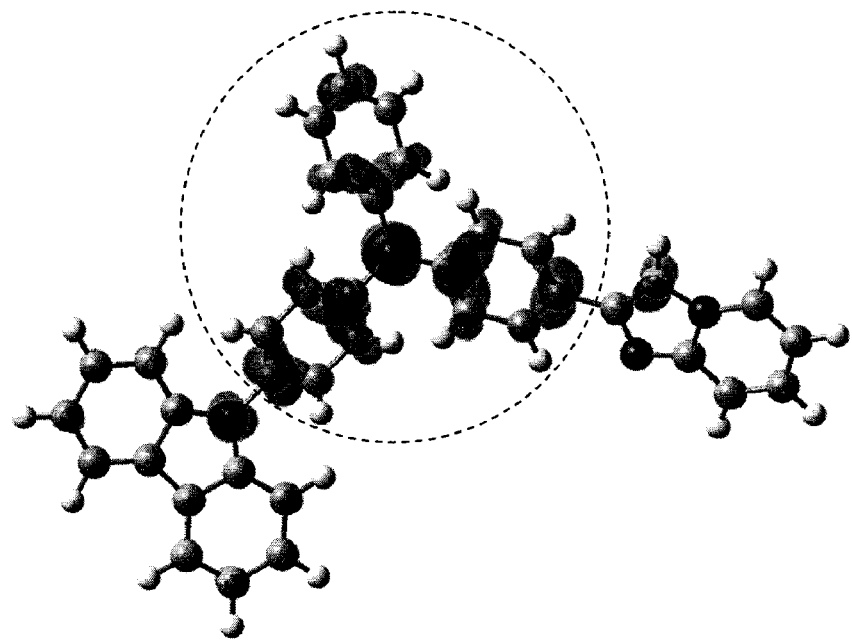
FIGS. 33A and 33B are views showing the highest occupied molecular orbital and lowest unoccupied molecular orbital of YGAPIM which were obtained by calculation.
Figure 33B:
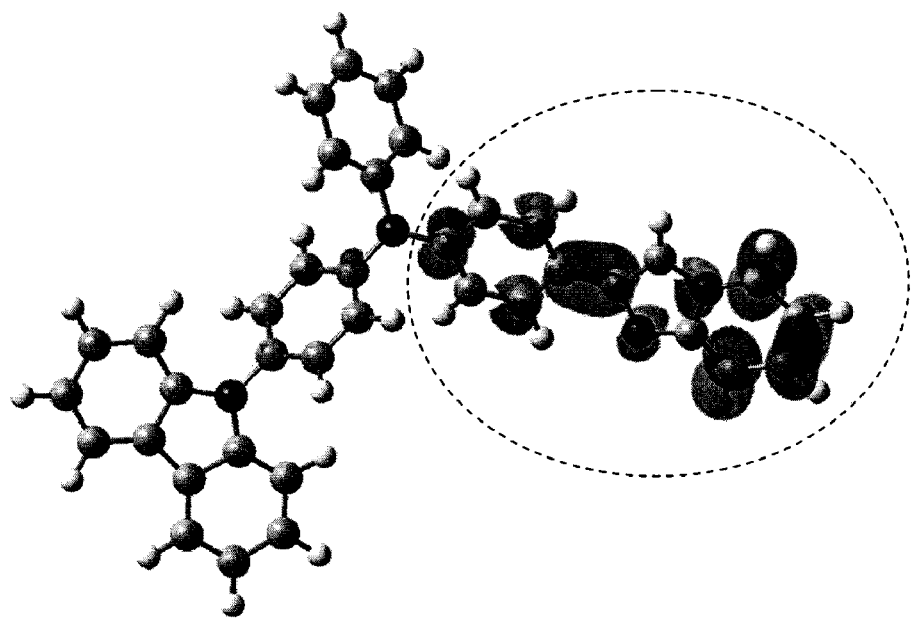

The highest occupied molecular orbital (HOMO) and lowest unoccupied molecular orbital (LUMO) of YGAPIM in a suitable molecular structure, which were obtained by the calculations, were visualized by Gauss View 4.1 to be shown in FIGS. 33A and 33B. FIG. 33A shows the highest occupied molecular orbital (HOMO), and FIG. 33B shows the lowest unoccupied molecular orbital (LUMO). In FIGS. 33A and 33B, the spheres represent atoms forming YGAPIM and cloud-like objects around the atoms represent the highest occupied molecular orbital (HOMO) and the lowest unoccupied molecular orbital (LUMO).

According to FIGS. 33A and 33B, the highest occupied molecular orbital exists near amine, which shows that an amino group greatly contributes to the hole-transporting property of YGAPIM. In addition, the lowest occupied molecular orbital exists near imidazopyridine, which shows that an imidazopyridyl group greatly contributes to the electron-transporting property of YGAPIM. Thus, an imidazopyridine skeleton having an electron-transporting property, which is a hetero aromatic ring, and an amine skeleton having a hole-transporting property are introduced in a molecule. Accordingly, it is found that YGAPIM is a bipolar material having electron- and hole-transporting properties.

Example 3

In Example 3, an example of a synthesis method of N-[4-(imidazo[1,2-a]pyridin-2-yl)phenyl]-N,9-diphenyl-9H-carbazole-3-amine (abbreviation: PCAPIM) which is represented by a structural formula (137) will be described.

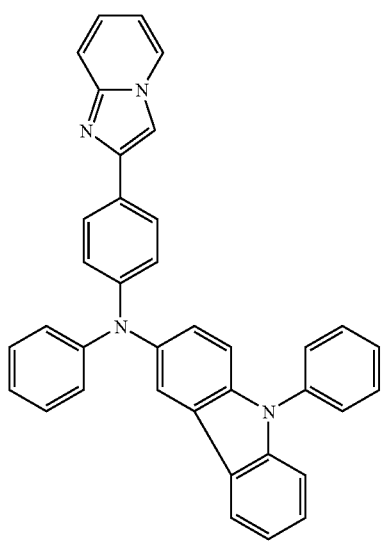

(137)

A synthesis scheme is shown in the following (E3-1).

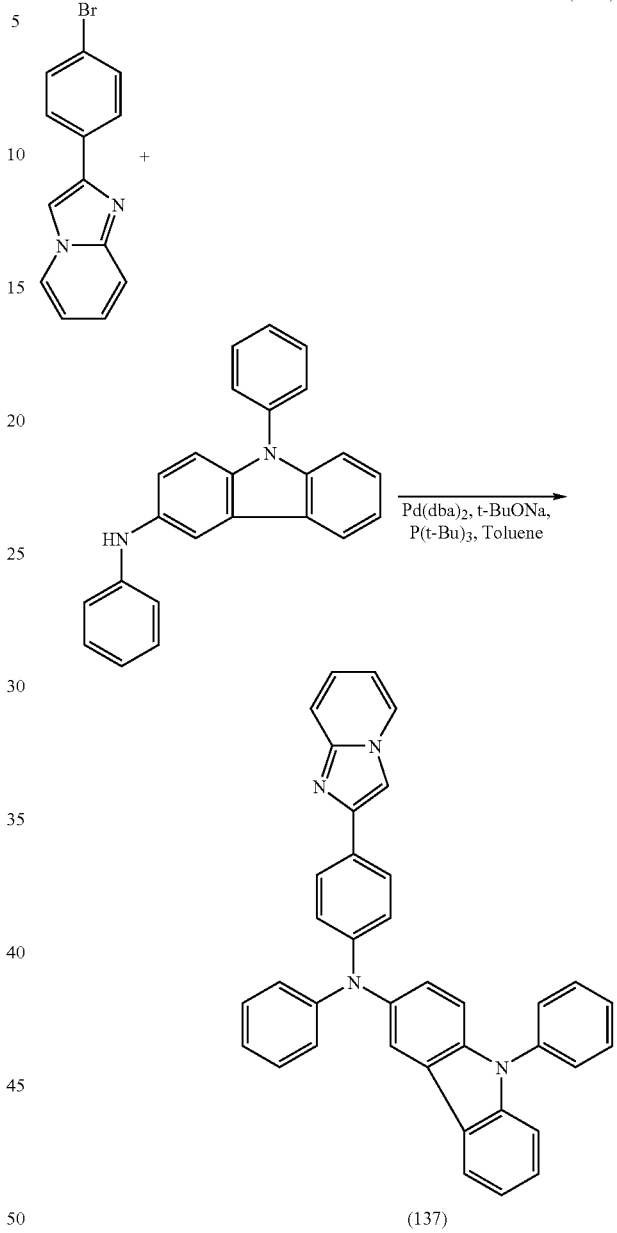

(E3-1)

(137)

In a 100 mL three-necked flask were placed 1.0 g (3.7 mmol) of 2-(4-bromophenyl)imidazo[1,2-a]pyridine, 0.66 g (7.3 mmol) of sodium tert-butoxide, 1.2 g (3.7 mmol) of N-phenyl-(9-phenyl-9H-carbazol-3-yl)amine (abbreviation: PCA), and 0.10 g (0.17 mmol) of bis(dibenzylideneacetone) palladium(0), and the atmosphere in the flask was replaced with nitrogen.

To this mixture were added 20 mL of toluene and 1.0 mL of a 10% hexane solution of tri(tert-butyl)phosphine. This mixture was stirred under a nitrogen stream at 120° C. for 5 hours. After the stirring, chloroform was added to this mixture, and this suspension was subjected to suction filtration through Celite, Florisil, and alumina to give a filtrate. The obtained filtrate was washed with water and a saturated saline solution in this order, and then the organic layer was dried with magnesium sulfate. After the drying, this mixture was subjected to suction filtration to give a filtrate. The obtained filtrate was concentrated to give a compound. The obtained compound was purified by silica gel column chromatography. The silica gel column chromatography was performed using toluene as a developing solvent. The obtained fraction was concentrated to give a compound. The compound was recrystallized with a mixed solvent of chloroform and hexane to give 1.3 g of a light yellow powdered solid in a yield of 67%.

In addition, 1.3 g of the obtained solid was sublimated and purified by train sublimation. The sublimation purification was performed under a reduced pressure of 7.0 Pa, with a flow rate of argon at 3.0 mL/min, at 300° C., and for 15 hours. After the sublimation purification, 0.55 g of a target substance was obtained in a yield of 42%.

By a nuclear magnetic resonance (NMR) method, this compound was confirmed to be N-[4-(imidazo[1,2-a]pyridin-2-yl)phenyl]-N,9-diphenyl-9H-carbazole-3-amine (abbreviation: PCAPIM), which was a target substance.

$^1$H NMR data of the obtained compound is shown below:
$^1$H NMR (CDCl$_3$, 300 MHz): δ=6.75 (t, J=6.4 Hz, 1H), 6.99 (t, J=6.8 Hz, 1H), 7.10-7.66 (m, 18H), 7.75-7.84 (m, 3H), 7.95-8.02 (m, 2H), 8.09 (d, J=6.8 Hz, 1H)

Figure 13A:
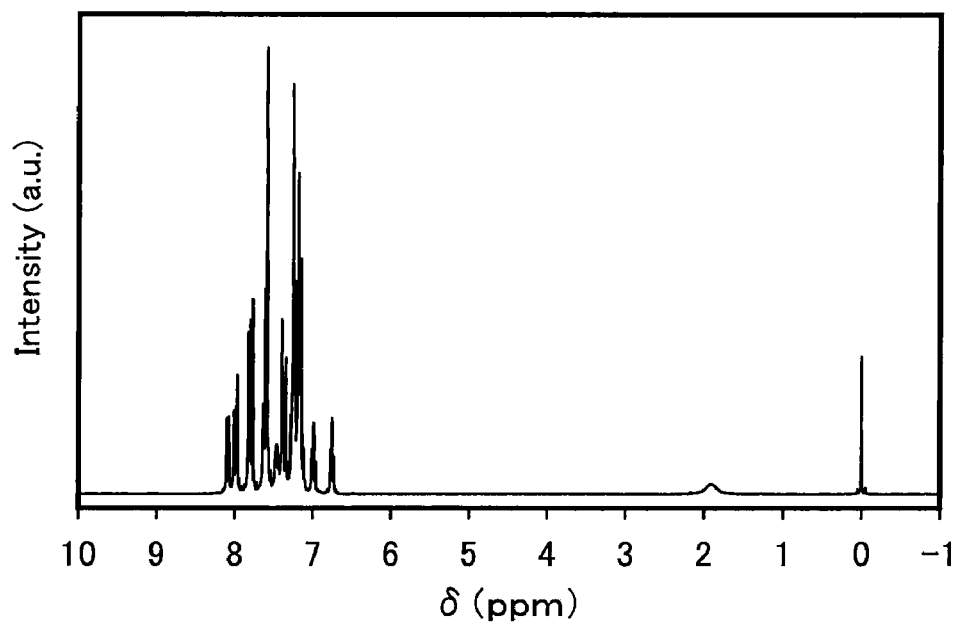
FIGS. 13A and 13B are $^1$H NMR charts of PCAPIM (abbreviation)
Figure 13B:
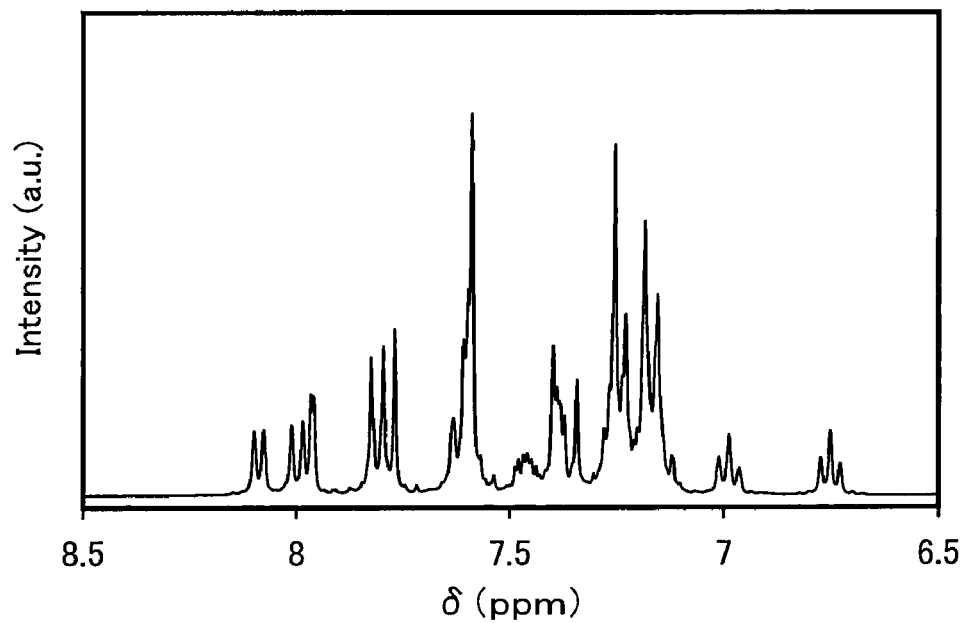

$^1$H-NMR charts are shown in FIGS. 13A and 13B. Note that FIG. 13B is a chart in which the range of 6.5 ppm to 8.5 ppm in FIG. 13A is enlarged.

Figure 14A:
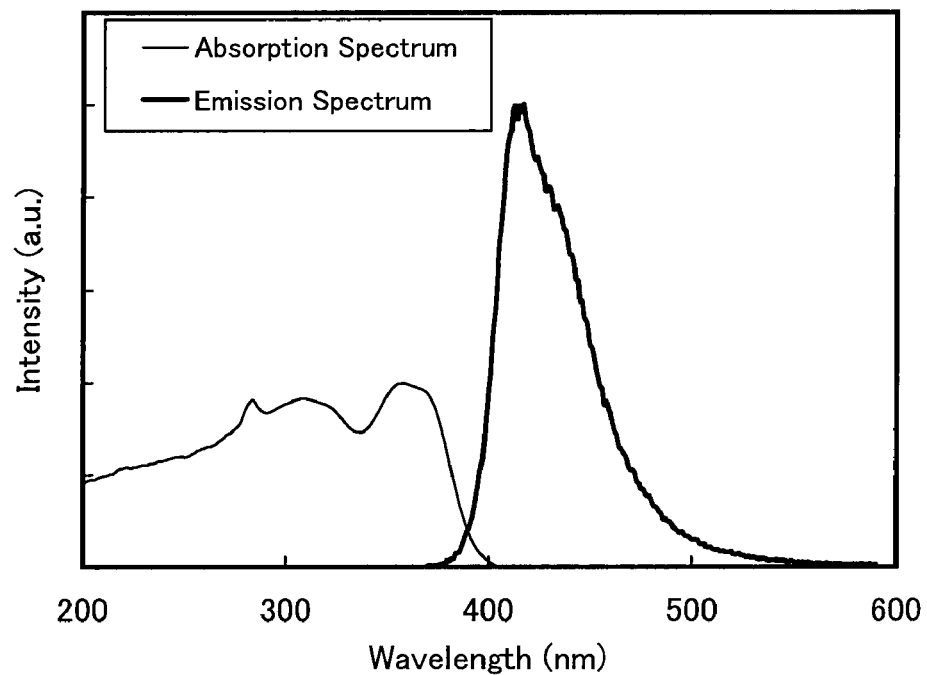
FIGS. 14A and 14B are graphs each showing an absorption spectrum and an emission spectrum of PCAPIM (abbreviation)
Figure 14B:
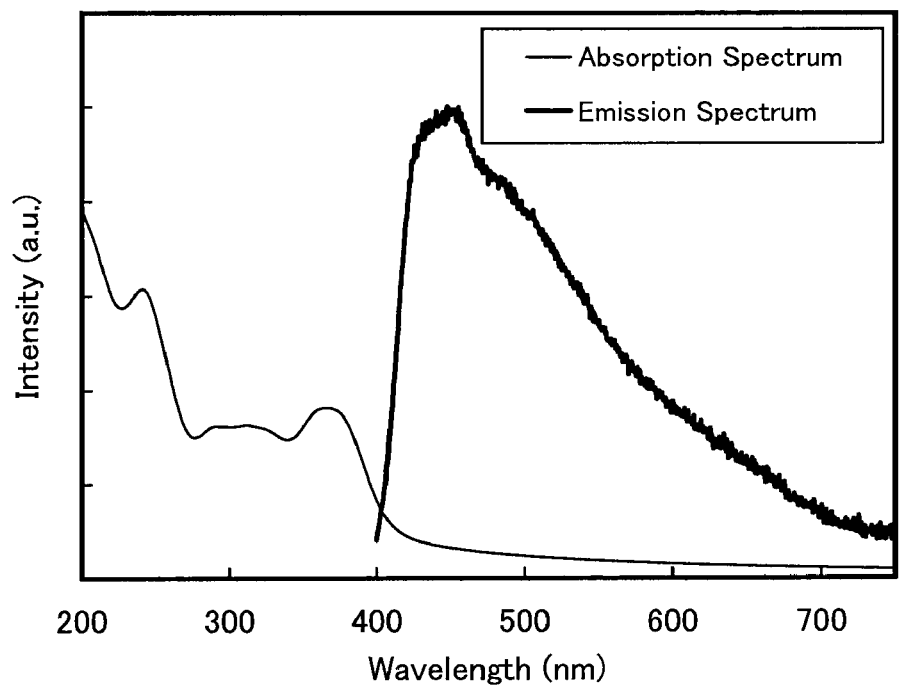

FIG. 14A shows an absorption spectrum and an emission spectrum of PCAPIM in a toluene solution. FIG. 14B shows an absorption spectrum and an emission spectrum of PCAPIM in a thin-film form. The measurement of the absorption spectra was performed using an ultraviolet-visible spectrophotometer (V-550, manufactured by JASCO Corporation). As for the samples for the measurement, the solution was put into a quartz cell and the thin film was obtained by evaporation of PCAPIM onto a quartz substrate. The absorption spectrum of PCAPIM in the solution, which is shown in FIG. 14A, was obtained by subtraction of the absorption spectra of the quartz cell and toluene from the raw absorption spectra. The absorption spectrum of PCAPIM in the thin-film form, which is shown in FIG. 14B, was obtained by subtraction of the absorption spectrum of the quartz substrate from the raw absorption spectra. In FIGS. 14A and 14B, the horizontal axis represents wavelength (nm) and the vertical axis represents intensity (arbitrary unit). In the case of PCAPIM in the toluene solution, the absorption was observed at about 357 nm, and the maximum emission wavelength was 415 nm (excitation wavelength: 357 nm). In the case of PCAPIM in the thin-film form, the absorption was observed at about 366 nm, and the maximum emission wavelength was 448 nm (excitation wavelength: 360 nm).

The HOMO level and the LUMO level of PCAPIM in the thin-film form were measured. The HOMO level was obtained by converting the ionization potential in air, which was measured by photoelectron spectrometer (AC-2, manufactured by Riken Keiki Co., Ltd.), into a negative value. In addition, the LUMO level was obtained in such a manner that the absorption edge was obtained from Tauc plot, with an assumption of direct transition, using data on the absorption spectrum of the thin film of PCAPIM in FIG. 14B, and the absorption edge was added to the HOMO level as an optical energy gap. Accordingly, the HOMO level, energy gap, and LUMO level of PCAPIM were −5.14 eV, 3.08 eV, and −2.06 eV, respectively.

Thus, it was found that PCAPIM has a large energy gap.

Example 4

In Example 4, an example of a synthesis method of N-[4-(imidazo[1,2-a]pyridin-2-yl)phenyl]-N,N',N'-triphenyl-1,4-phenylenediamine (abbreviation: DPAPIM) which is represented by a structural formula (100) will be described.

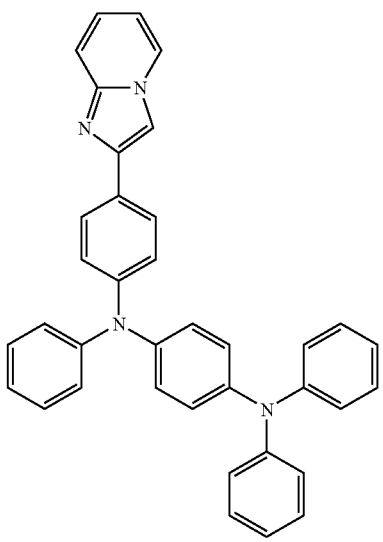

(100)

A synthesis scheme is shown in the following (E4-1).

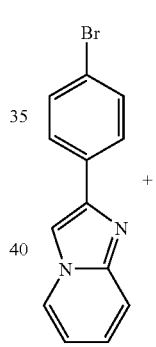

(E4-1)

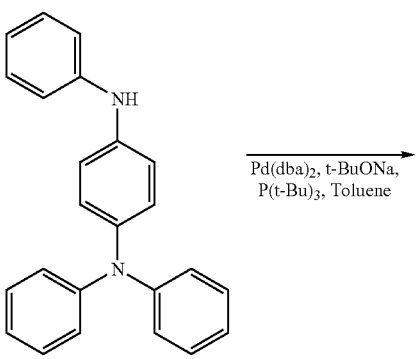

Pd(dba)$_2$, t-BuONa, P(t-Bu)$_3$, Toluene

-continued

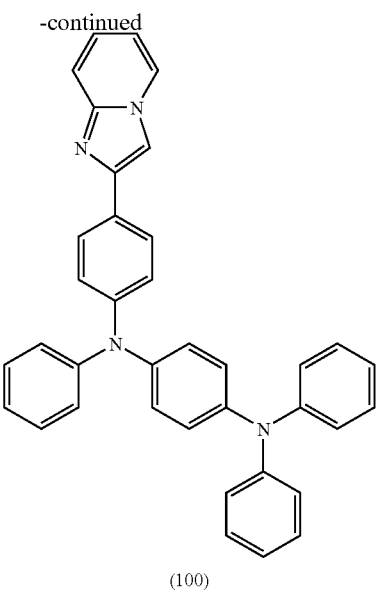

(100)

In a 100 mL three-necked flask were placed 1.6 g (5.9 mmol) of 2-(4-bromophenyl)imidazo[1,2-a]pyridine, 1.4 g (15 mmol) of sodium tert-butoxide, 2.0 g (5.9 mmol) of N,N',N'-triphenyl-1,4-phenylenediamine (abbreviation: DPA), and 0.20 g (0.35 mmol) of bis(dibenzylideneacetone) palladium(0), and the atmosphere in the flask was replaced with nitrogen.

To this mixture were added 30 mL of toluene and 0.20 mL of a 10% hexane solution of tri(tert-butyl)phosphine. This mixture was stirred under a nitrogen stream at 120° C. for 5 hours. After the stirring, toluene was added to this mixture, and this suspension was subjected to suction filtration through Celite to give a filtrate. The obtained filtrate was washed with water and a saturated saline solution in this order, and then the organic layer was dried with magnesium sulfate. After the drying, this mixture was subjected to suction filtration to give a filtrate. The obtained filtrate was concentrated to give a compound. The obtained compound was purified by silica gel column chromatography. The silica gel column chromatography was performed by, first, using a mixed solvent of toluene and hexane (toluene:hexane=1:2) as a developing solvent, and then using toluene as another developing solvent. The obtained fraction was concentrated to give a solid. This solid was recrystallized with a mixed solvent of chloroform and hexane to give 2.5 g of a white powdered solid in a yield of 80%.

In addition, 2.5 g of the obtained solid was sublimated and purified by train sublimation. The sublimation purification was performed under a reduced pressure of 7.0 Pa, with a flow rate of argon at 3.0 mL/min, at 281° C., and for 22 hours. After the sublimation purification, 2.0 g of a target substance was obtained in a yield of 80%.

By a nuclear magnetic resonance (NMR) method, this compound was confirmed to be N-[4-(imidazo[1,2-a]pyridin-2-yl)phenyl]-N,N',N'-triphenyl-1,4-phenylenediamine (abbreviation: DPAPIM), which was a target substance.

$^1$H NMR data of the obtained compound is shown below:
$^1$H NMR (CDCl$_3$, 300 MHz): δ=6.75 (td, J1=6.4 Hz, J2=0.98 Hz, 1H), 6.95-7.29 (m, 22H), 7.60 (d, J=9.8 Hz, 1H), 7.77 (s, 1H), 7.83 (d, J=8.8 Hz, 2H), 8.08 (d, J=6.8 Hz, 1H)

Figure 15A:
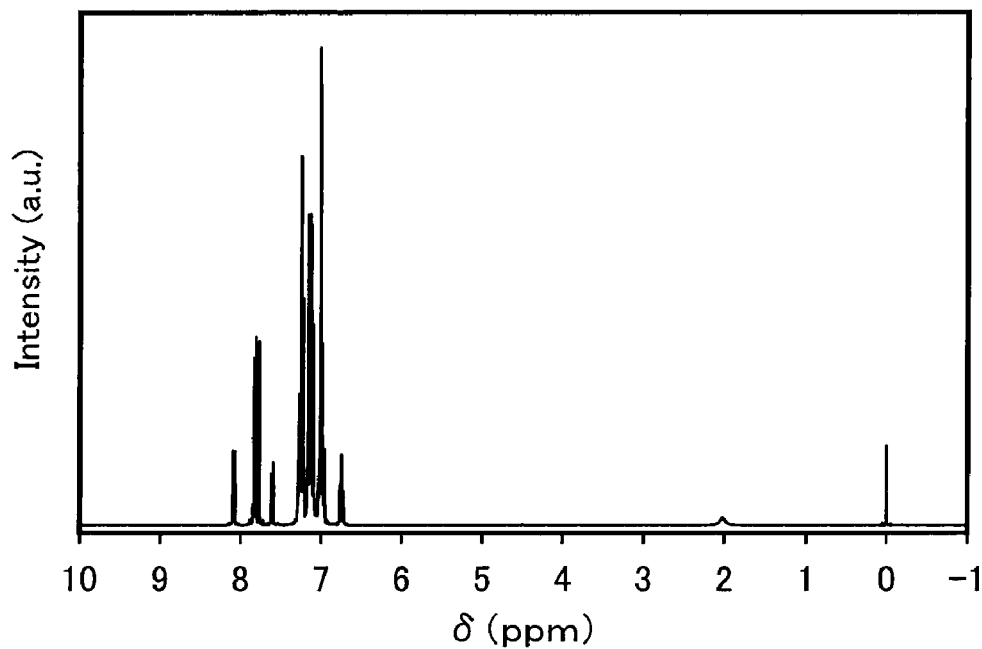
FIGS. 15A and 15B are $^1$H NMR charts of DPAPIM (abbreviation)
Figure 15B:
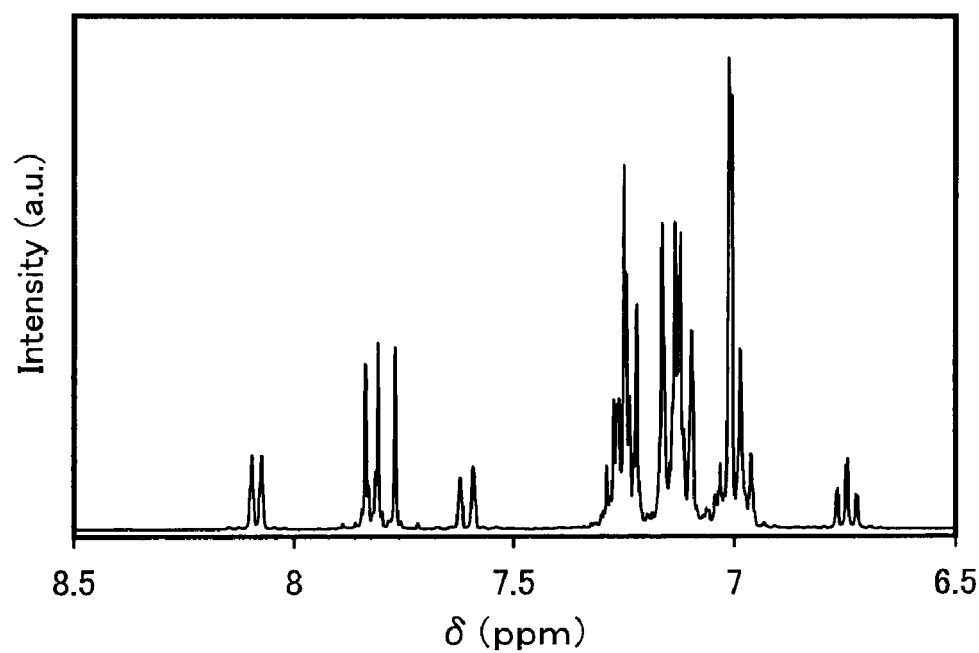

$^1$H-NMR charts are shown in FIGS. 15A and 15B. Note that FIG. 15B is a chart in which the range of 6.5 ppm to 8.5 ppm in FIG. 15A is enlarged.

Figure 16A:
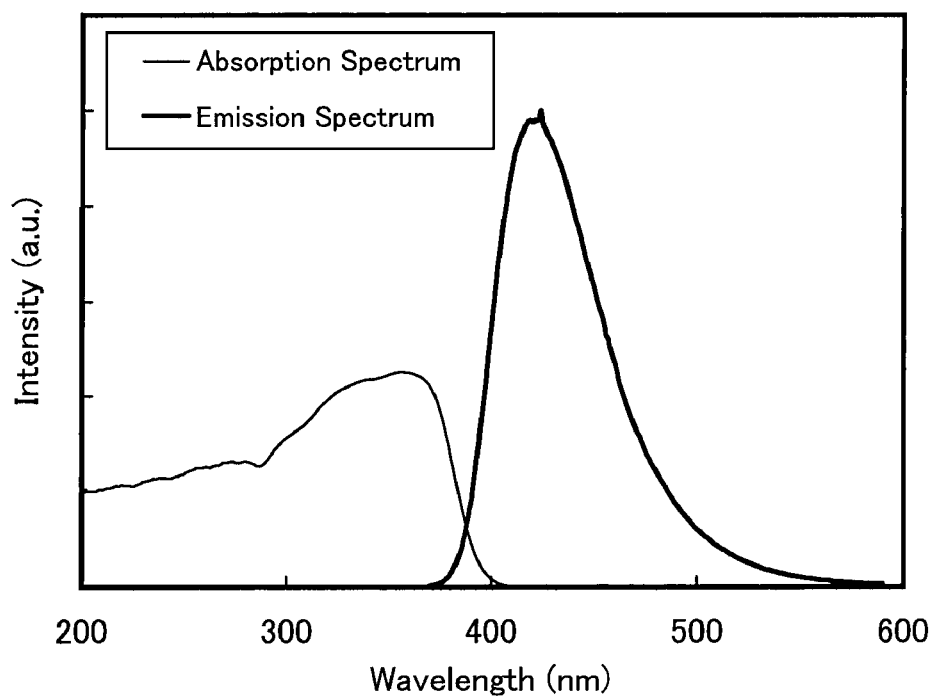
FIGS. 16A and 16B are graphs each showing absorption and emission spectra of DPAPIM (abbreviation)
Figure 16B:
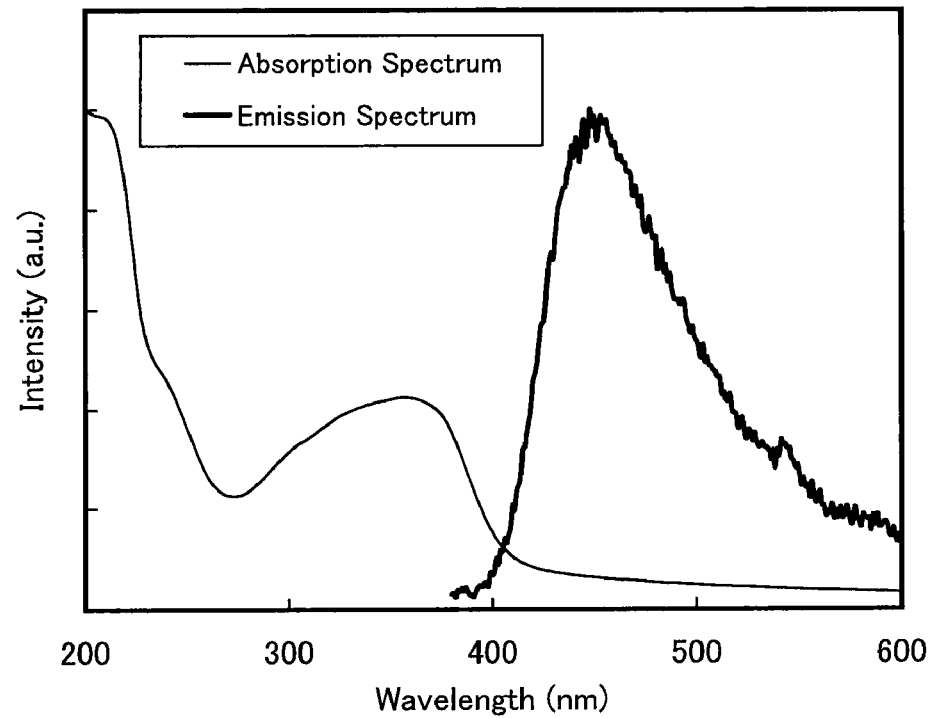

FIG. 16A shows an absorption spectrum and an emission spectrum of DPAPIM in a toluene solution. FIG. 16B shows an absorption spectrum and an emission spectrum of DPA-PIM in a thin-film form. The measurement of the absorption spectra was performed using an ultraviolet-visible spectrophotometer (V-550, manufactured by JASCO Corporation). As for samples for the measurement, the solution was put into a quartz cell and the thin film was obtained by evaporation of DPAPIM onto a quartz substrate. The absorption spectrum of DPAPIM in the solution, which is shown in FIG. 16A, was obtained by subtraction of the absorption spectra of the quartz cell and toluene from the raw absorption spectra. The absorption spectrum of DPAPIM in the thin-film form, which is shown in FIG. 16B, was obtained by subtraction of the absorption spectrum of the quartz substrate from the raw absorption spectra. In FIGS. 16A and 16B, the horizontal axis represents wavelength (nm) and the vertical axis represents intensity (arbitrary unit). In the case of DPAPIM in the toluene solution, the absorption was observed at about 361 nm, and the maximum emission wavelength was 424 nm (excitation wavelength: 356 nm). In the case of DPAPIM in the thin-film form, the absorption was observed at about 356 nm, and the maximum emission wavelength was 448 nm (excitation wavelength: 356 nm).

The HOMO level and the LUMO level of DPAPIM in the thin-film form were measured. The HOMO level was obtained by converting the ionization potential in air, which was measured by photoelectron spectrometer (AC-2, manufactured by Riken Keiki Co., Ltd.), into a negative value. In addition, the LUMO level was obtained in such a manner that the absorption edge was obtained from Tauc plot, with an assumption of direct transition, using data on the absorption spectrum of the thin film of DPAPIM in FIG. 16B, and the absorption edge was added to the HOMO level as an optical energy gap. Accordingly, the HOMO level, energy gap, and LUMO level of DPAPIM were −5.25 eV, 3.02 eV, and −2.23 eV, respectively.

Thus, it was found that DPAPIM has a large energy gap.

Example 5

In Example 5, an example of a synthesis method of 4-(9H-carbazol-9-yl)-4'-(1-phenyl-1H-benzo[d]imidazol-2-yl) triphenylamine (abbreviation: YGABIm) which is represented by a structural formula (227) will be described.

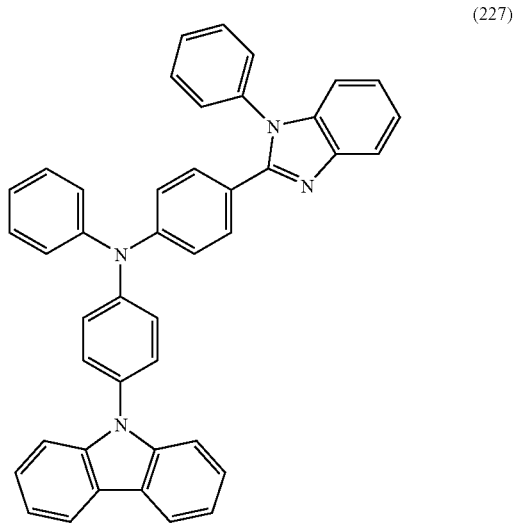

(227)

A synthesis scheme is shown in the following (E5-1).

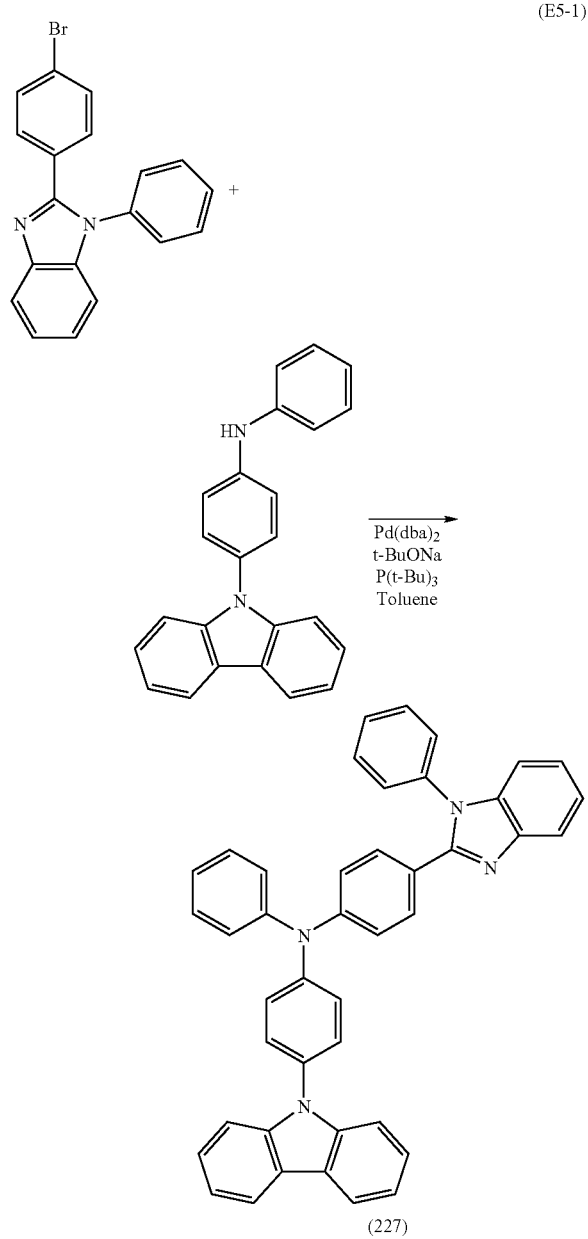

In a 100 mL three-necked flask were placed 1.0 g (2.7 mmol) of 2-(4-bromophenyl)-1-phenyl-1H-benzo[d]imidazole, 0.96 g (2.7 mmol) of 4-(carbazol-9-yl)diphenylamine (abbreviation: YGA), 0.60 g (6.3 mmol) of sodium tert-butoxide, and 0.050 g (0.086 mmol) of bis(dibenzylideneacetone)palladium(0), and the atmosphere in the flask was replaced with nitrogen.

To this mixture were added 15 mL of toluene and 0.050 mL of a 10% hexane solution of tri(tert-butyl)phosphine. This mixture was stirred at 80° C. for 5 hours. After the stirring, toluene was added to this mixture, and this suspension was subjected to suction filtration through Celite to give a filtrate. The obtained filtrate was washed with water, a saturated sodium hydrogen carbonate solution, and a saturated saline solution in this order. Then, the organic layer and the aqueous layer were separated, and magnesium sulfate was added to dry the organic layer. This mixture was subjected to suction filtration so that the magnesium sulfate was removed to give a filtrate. The obtained filtrate was concentrated to give a compound. The obtained compound was purified by silica gel column chromatography. The silica gel column chromatography was performed by, first, using toluene as a developing solvent, and then using a mixed solvent of toluene and ethyl acetate (toluene:ethyl acetate=5:1) as a developing solvent. The obtained fraction was concentrated to give a compound. The obtained compound was recrystallized with a mixed solvent of chloroform and hexane to give 1.2 g of a light yellow powdered solid in a yield of 74%.

Then, 1.2 g of the obtained solid was sublimated and purified by train sublimation. The sublimation purification was performed under a reduced pressure of 2.7 Pa, with a flow rate of argon at 5 mL/min, at 261° C., and for 14 hours. After the sublimation purification, 1.0 g of a target substance was obtained in a yield of 83%.

By a nuclear magnetic resonance (NMR) method, this compound was confirmed to be 4-(9H-carbazol-9-yl)-4'-(1-phenyl-1H-benzo[d]imidazol-2-yl)triphenylamine (abbreviation: YGABIm), which was a target substance.

$^1$H NMR data of the obtained compound is shown below:
$^1$H NMR (CDCl$_3$, 300 MHz): δ=7.30-7.56 (m, 27H), 7.87 (d, J=8.3 Hz, 1H), 8.13 (d, J=7.8 Hz, 2H)

Figure 17A:
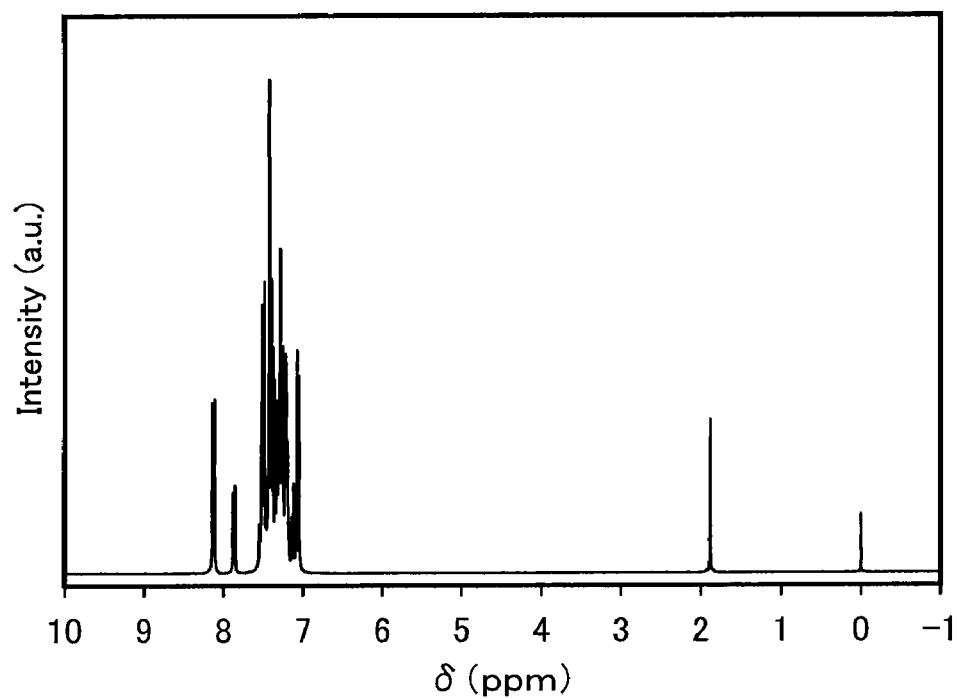
FIGS. 17A and 17B are $^1$H NMR charts of YGABIm (abbreviation)
Figure 17B:
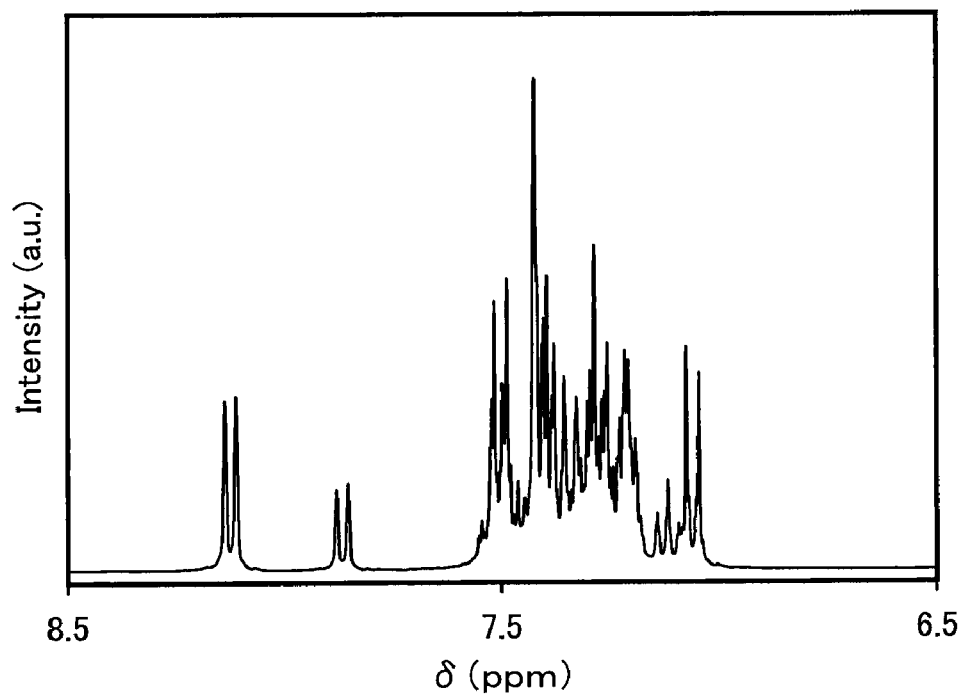

$^1$H-NMR charts are shown in FIGS. 17A and 17B. Note that FIG. 17B is a chart in which the range of 6.5 ppm to 8.5 ppm in FIG. 17A is enlarged.

Figure 18A:
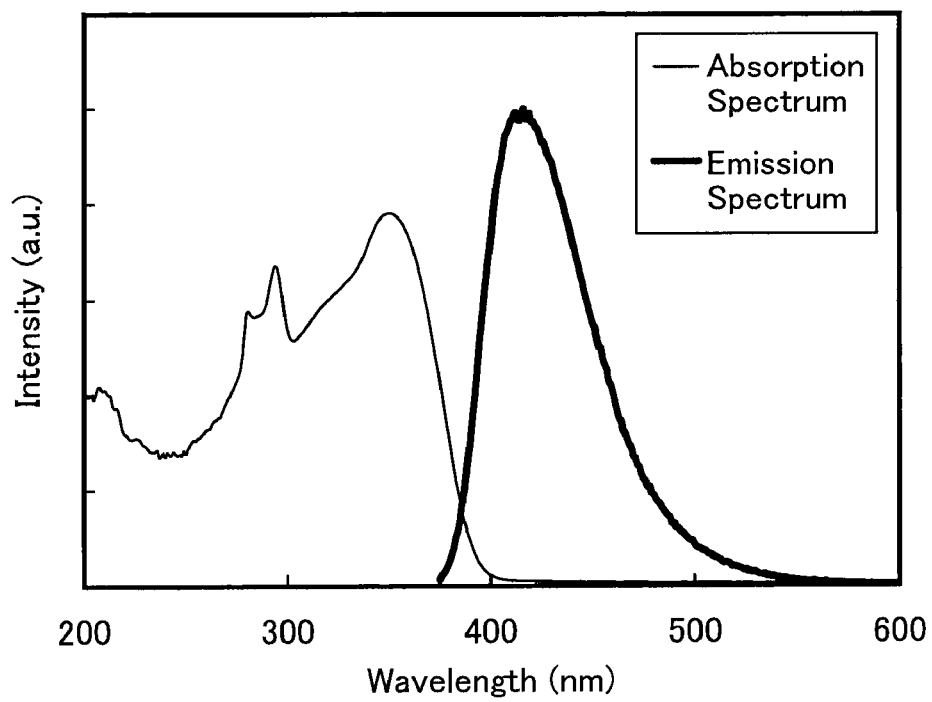
FIGS. 18A and 18B are graphs each showing absorption and emission spectra of YGABIm (abbreviation)
Figure 18B:
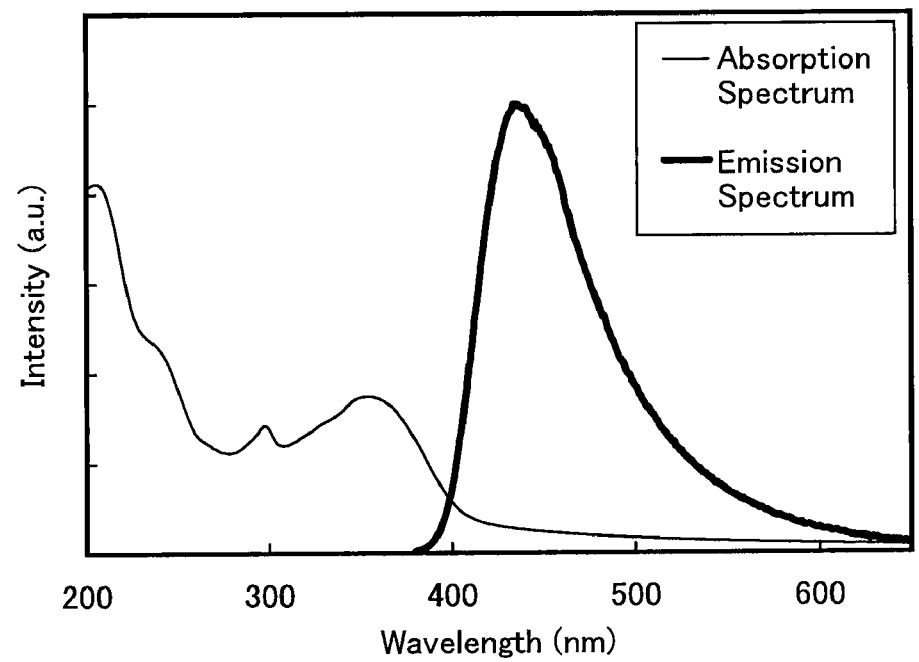

FIG. 18A shows an absorption spectrum and an emission spectrum of YGABIm in a toluene solution. FIG. 18B shows an absorption spectrum and an emission spectrum of YGABIm in a thin-film form. The measurement of the absorption spectra was performed using an ultraviolet-visible spectrophotometer (V-550, manufactured by JASCO Corporation). As for samples for the measurement, the solution was put into a quartz cell and the thin film was obtained by evaporation of YGABIm onto a quartz substrate. The absorption spectrum of YGABIm in the solution, which is shown in FIG. 18A, was obtained by subtraction of the absorption spectra of the quartz cell and toluene from the raw absorption spectra. The absorption spectrum of YGABIm in the thin-film form, which is shown in FIG. 18B, was obtained by subtraction of the absorption spectrum of the quartz substrate from the raw absorption spectra. In FIGS. 18A and 18B, the horizontal axis represents wavelength (nm) and the vertical axis represents intensity (arbitrary unit). In the case of YGABIm in the toluene solution, the absorption was observed at about 348 nm, and the maximum emission wavelength was 416 nm (excitation wavelength: 348 nm). In the case of YGABIm in the thin-film form, the absorption was observed at about 354 nm, and the maximum emission wavelength was 436 nm (excitation wavelength: 366 nm).

The HOMO level and the LUMO level of YGABIm in the thin-film form were measured. The HOMO level was obtained by converting the ionization potential in air, which was measured by photoelectron spectrometer (AC-2, manufactured by Riken Keiki Co., Ltd.), into a negative value. In addition, the LUMO level was obtained in such a manner that the absorption edge was obtained from Tauc plot, with an assumption of direct transition, using data on the absorption spectrum of the thin film of YGABIm in FIG. 18B, and the absorption edge was added to the HOMO level as an optical energy gap. Accordingly, the HOMO level, energy gap, and LUMO level of YGABIm were −5.44 eV, 3.12 eV, and −2.32 eV, respectively.

Thus, it was found that YGABIm has a large energy gap.

Further, the optimal molecular structure of YGABIm in the ground state was calculated using the density functional theory (DFT). In the DFT, the total energy is represented as the sum of potential energy, electrostatic energy between electrons, electronic kinetic energy, and exchange-correlation energy including all the complicated interactions between electrons. Also in the DFT, an exchange-correlation interaction approximates a functional (a function of another function) of one electron potential expressed as electron density; thus, high-speed and high-accuracy calculation is obtained. Here, B3LYP, which is a hybrid functional, was used to specify the weight of each parameter related to exchange-correlation energy. In addition, as a basis function, 6-311 (a basis function of a triple-split valence basis set using three contraction functions for each valence orbital) was applied to all the atoms. By the above basis function, for example, orbits of is to 3s are considered in the case of hydrogen atoms while orbits of 1 s to 4s and 2p to 4p are considered in the case of carbon atoms. Furthermore, for improvement of the calculation accuracy, the p function and the d function as polarization basis sets were added respectively to hydrogen atoms and atoms other than hydrogen atoms.

Note that Gaussian 03 was used as a quantum chemistry computational program. A high performance computer (manufactured by SGI Japan, Ltd., Altix 4700) was used for the calculations.

Figure 34A:
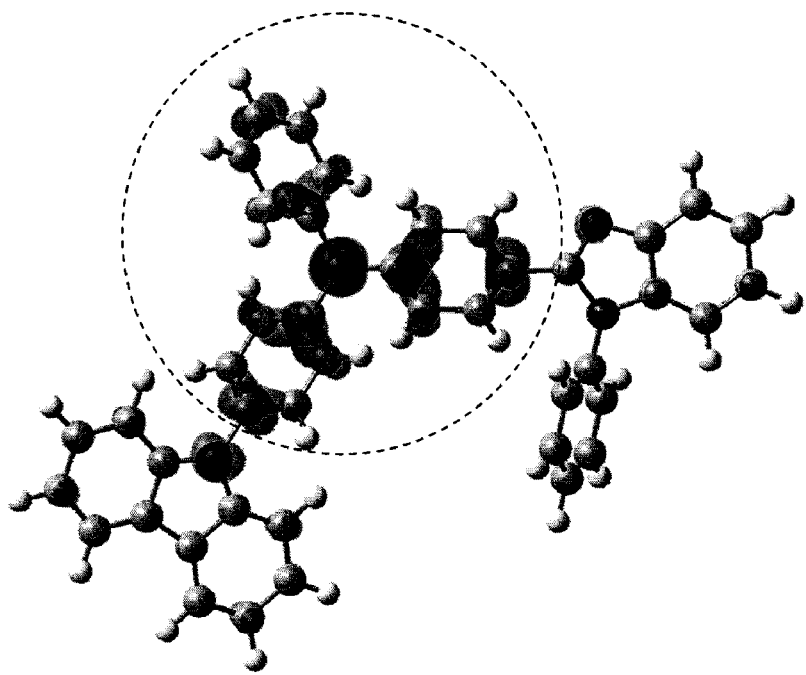
FIGS. 34A and 34B are views showing the highest occupied molecular orbital and lowest unoccupied molecular orbital of YGABIm which were obtained by calculation.
Figure 34B:
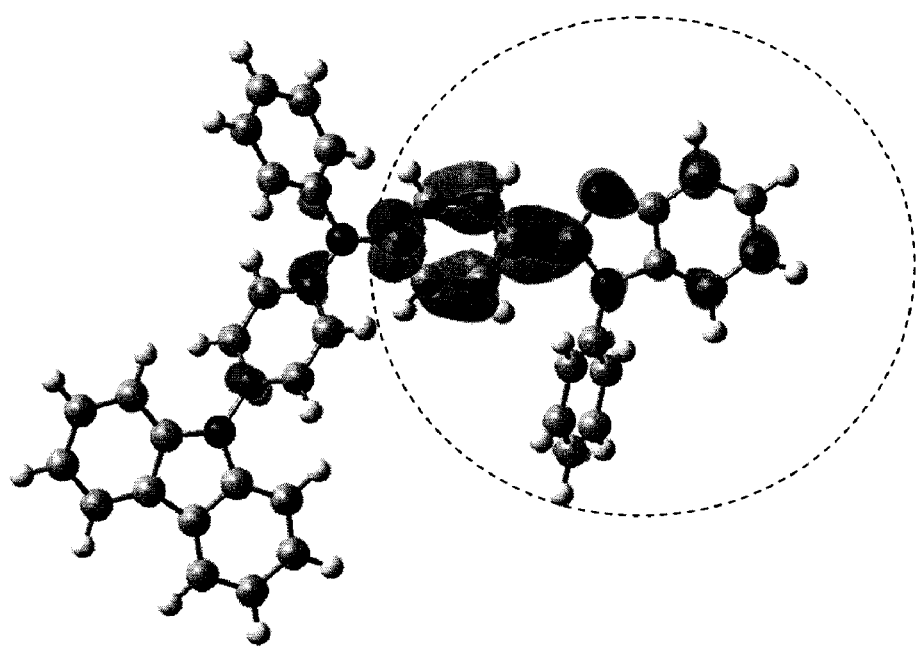

The highest occupied molecular orbital (HOMO) and lowest unoccupied molecular orbital (LUMO) of YGABIm in a suitable molecular structure, which were obtained by the calculations, were visualized by Gauss View 4.1 to be shown in FIGS. 34A and 34B. FIG. 34A shows the highest occupied molecular orbital (HOMO), and FIG. 34B shows the lowest unoccupied molecular orbital (LUMO). In FIGS. 34A and 34B, the spheres represent atoms forming YGABIm and cloud-like objects around the atoms represent the highest occupied molecular orbital (HOMO) and the lowest unoccupied molecular orbital (LUMO).

According to FIGS. 34A and 34B, the highest occupied molecular orbital exists near amine, which shows that an amino group greatly contributes to the hole-transporting property of YGABIm. In addition, the lowest occupied molecular orbital exists near benzimidazole, which shows that a benzimidazolyl group greatly contributes to the electron-transporting property of YGABIm. Thus, a benzimidazole skeleton having an electron-transporting property, which is a hetero aromatic ring, and an amine skeleton having a hole-transporting property are introduced in a molecule. Accordingly, it is found that YGABIm is a bipolar material having electron- and hole-transporting properties.

Example 6

In Example 6, a formation method of a light-emitting element in which the heterocyclic compound described in Embodiment 1 is used as a host material of a light-emitting layer and measurement results of the element characteristics will be described. Specifically, a light-emitting element 1 formed using 4-(benzo[d]oxazol-2-yl)-4'-(9H-carbazol-9-yl)triphenylamine (abbreviation: YGABOx) which is described in Example 1 will be described.

The element structure of the light-emitting element 1 formed in this example is shown in Table 1. In Table 1, the mixture ratios are all represented in weight ratios.

TABLE 1

|  | 1st Electrode 1502 | 1st Layer 1511 | 2nd Layer 1512 | 3rd Layer 1513 | 4th Layer 1514 | 5th Layer 1515 | 2nd Electrode 1504 |
| --- | --- | --- | --- | --- | --- | --- | --- |
| Light-Emitting Element 1 | ITSO 110 nm | NPB:MoOx (=4:1) 40 nm | YGA1BP 20 nm | YGABOx:Ir(ppy)$_2$acac (=1:0.06) 40 nm | BAlq 10 nm | BPhen 20 nm | LiF 1 nm | Al 200 nm |

* Mixture Ratios Are All Represented In Weight Ratios

Figure 19:
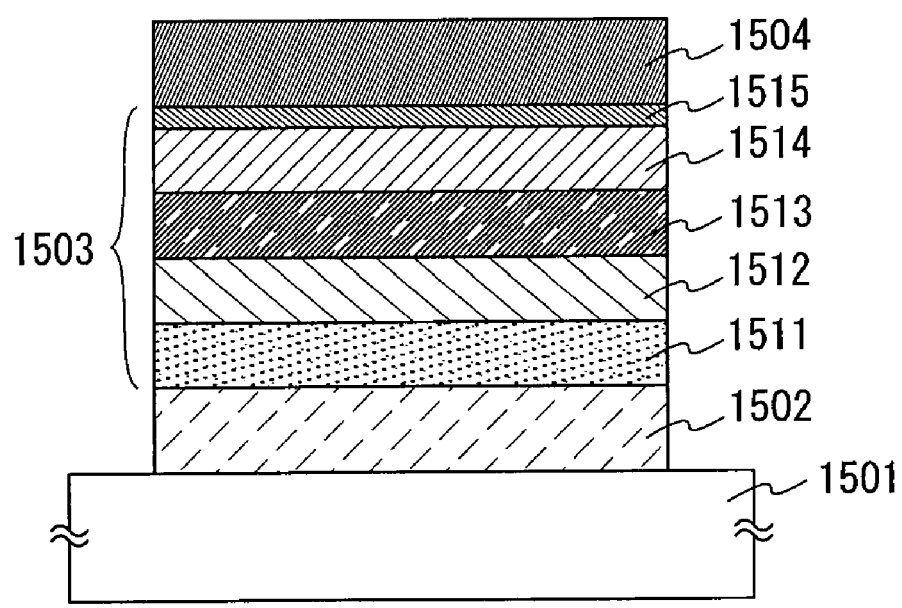
FIG. 19 is a view illustrating a light-emitting element.

Hereinafter, the formation method of the light-emitting element 1 of this example is described with reference to FIG. 19. In addition, structural formulae of organic compounds used in this example are shown below.

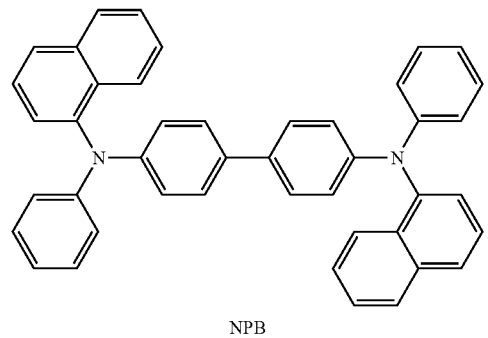

NPB

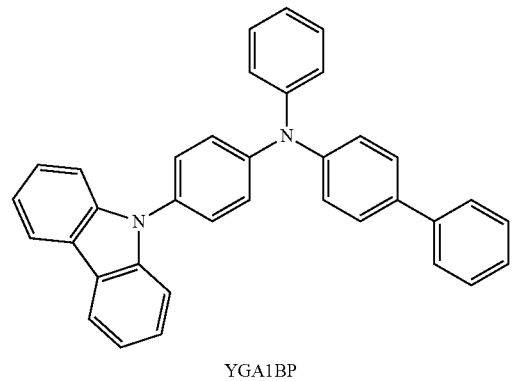

YGA1BP

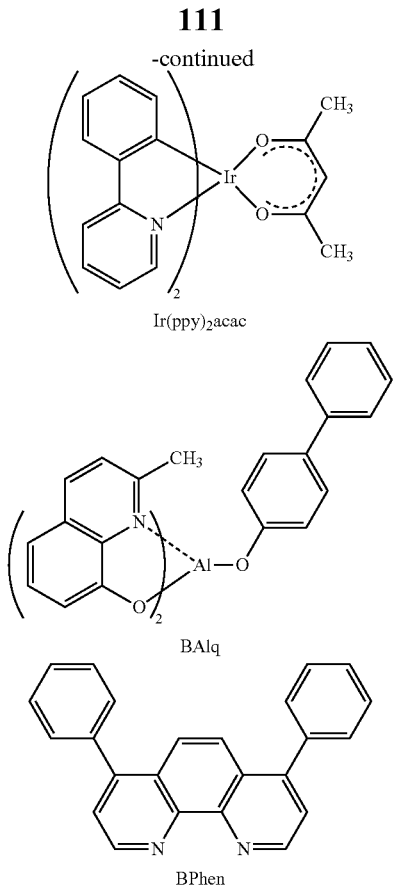

Ir(ppy)₂acac

BAlq

BPhen

First, indium oxide-tin oxide containing silicon oxide was deposited on a substrate 1501 which was a glass substrate by a sputtering method to form a first electrode 1502. The thickness of the first electrode was 110 nm and the area thereof was 2 mm×2 mm.

Next, an EL layer 1503 in which a plurality of layers are stacked was formed over the first electrode 1502. In this example, the EL layer 1503 has a structure in which a first layer 1511 which is a hole-injecting layer, a second layer 1512 which is a hole-transporting layer, a third layer 1513 which is a light-emitting layer, a fourth layer 1514 which is an electron-transporting layer, and a fifth layer 1515 which is an electron-injecting layer are stacked in this order.

The substrate 1501 provided with the first electrode 1502 was fixed on a substrate holder that was provided in a vacuum evaporation apparatus so that a surface provided with the first electrode 1502 faced downward. The pressure in the vacuum evaporation apparatus was reduced to approximately $10^{-4}$ Pa. Then, on the first electrode 1502, 4,4'-bis[N-(1-naphthyl)-N-phenylamino]biphenyl (abbreviation: NPB) and molybdenum(VI) oxide were co-evaporated to form the first layer 1511 which was a hole-injecting layer. The thickness of the first layer 1511 was 40 nm, and the evaporation rate was adjusted so that the mass ratio of NPB to molybdenum(VI) oxide was 4:1 (=NPB:molybdenum oxide). Note that the co-evaporation method refers to an evaporation method in which evaporation is carried out from a plurality of evaporation sources at the same time in one treatment chamber.

Next, a 20-nm-thick film of a hole-transporting material was formed on the first layer 1511 by an evaporation method using resistance heating to form the second layer 1512 which was a hole-transporting layer. Note that for the second layer 1512, 4-(9H-carbazol-9-yl)-4'-phenyltriphenylamine (abbreviation: YGA1BP) was used.

Next, the third layer 1513 which was a light-emitting layer was formed on the second layer 1512 by an evaporation method using resistance heating. The third layer 1513 was formed by co-evaporation of 4-(benzo[d]oxazol-2-yl)-4'-(9H-carbazol-9-yl)triphenylamine (abbreviation: YGABOx) and bis(2-phenylpyridinato-N,C²')iridium(III) acetylacetonate (abbreviation: Ir(ppy)₂(acac)) to a thickness of 40 nm. Here, the evaporation rate was adjusted so that the mass ratio of YGABOx to Ir(ppy)₂acac was 1:0.06 (=YGABOx:Ir(ppy)₂acac).

Furthermore, on the third layer 1513, bis(2-methyl-8-quinolinolato)(4-phenylphenolato)aluminum(III) (abbreviation: BAlq) was formed to a thickness of 10 nm and thereon, bathophenanthroline (abbreviation: BPhen) was formed to a thickness of 20 nm to form the fourth layer 1514 which was an electron-transporting layer.

A 1-nm-thick film of lithium fluoride (LiF) was deposited on the fourth layer 1514 to form the fifth layer 1515 which was an electron-injecting layer.

Lastly, a 200-nm-thick film of aluminum was formed by an evaporation method using resistance heating to form the second electrode 1504. Thus, the light-emitting element 1 was formed.

After the thus obtained light-emitting element 1 was sealed in a glove box under a nitrogen atmosphere so as not to be exposed to the air, operation characteristics of the light-emitting element were measured. Note that the measurement was carried out at room temperature (in an atmosphere in which the temperature was kept at 25° C.).

Figure 20:
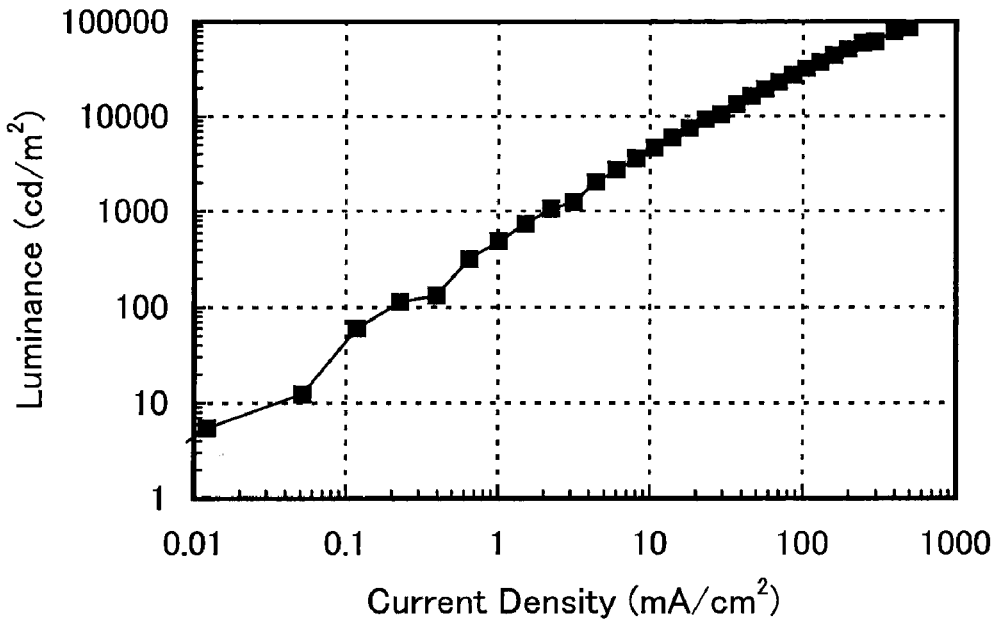
FIG. 20 is a graph showing current density-luminance characteristics of a light-emitting element 1.
Figure 21:
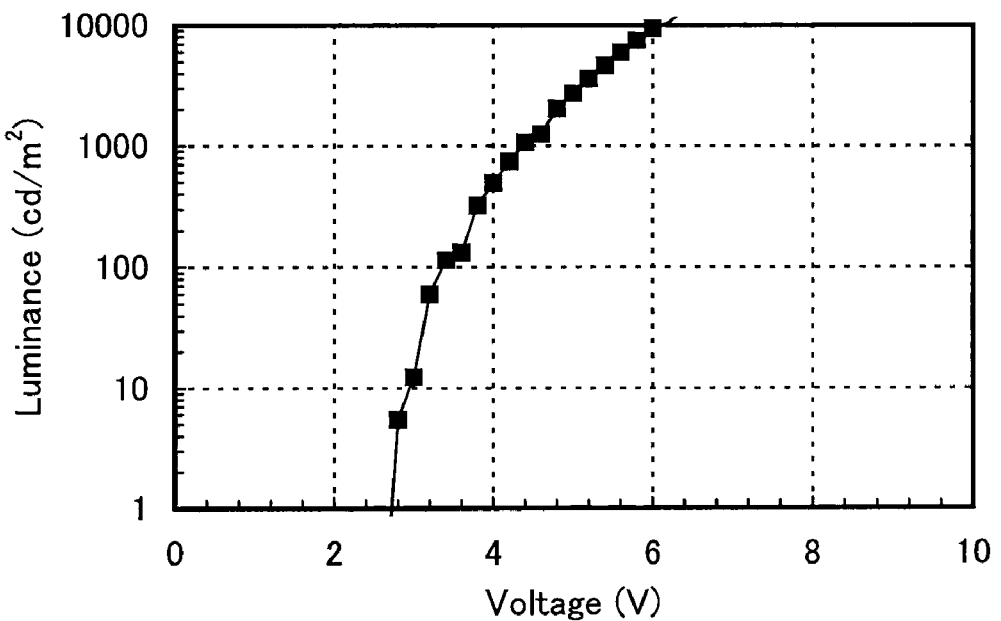
FIG. 21 is a graph showing voltage-luminance characteristics of the light-emitting element 1.
Figure 22:
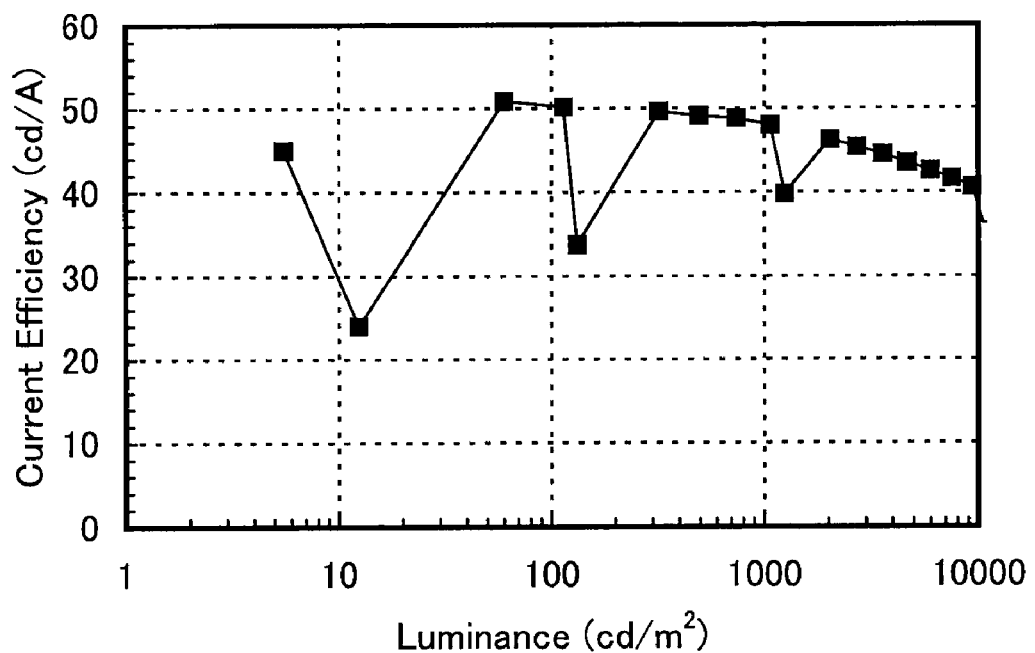
FIG. 22 is a graph showing luminance-current efficiency characteristics of the light-emitting element 1.

FIG. 20 shows the current density-luminance characteristics of the light-emitting element 1. FIG. 21 shows the voltage-luminance characteristics thereof. FIG. 22 shows the luminance-current efficiency characteristics thereof. In FIG. 20, the vertical axis represents luminance (cd/m²) and the horizontal axis represents current density (mA/cm²). In FIG. 21, the vertical axis represents luminance (cd/m²) and the horizontal axis represents voltage (V). In FIG. 22, the vertical axis represents current efficiency (cd/A) and the horizontal axis represents luminance (cd/m²). In addition, Table 2 shows the voltage, chromaticity, current efficiency, and quantum efficiency of the light-emitting element around 1000 cd/m².

TABLE 2

|  | Voltage (V) | Chromaticity (x, y) | current efficiency (cd/A) | quantum efficiency (%) |
| --- | --- | --- | --- | --- |
| Light-Emitting Element 1 | 4.4 | (0.36, 0.61) | 48.0 | 13.1 |

Figure 23:
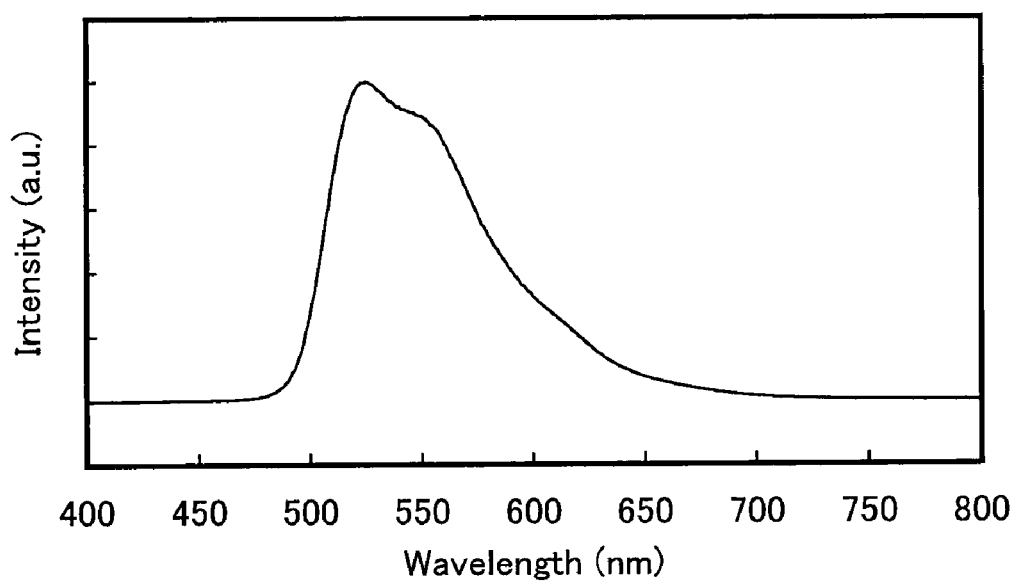
FIG. 23 is a graph showing an emission spectrum of the light-emitting element 1.

FIG. 23 shows the emission spectrum of the light-emitting element 1. As shown in FIG. 23, in the light-emitting element 1, a wavelength of green light, which is derived from Ir(ppy)₂acac that is a guest material, was observed, whereas an emission wavelength derived from YGABOx that is a host material was not observed. Thus, it was found that the heterocyclic compound described in Embodiment 1 (YGABOx in this example) functions as a bipolar host material in the light-emitting layer of the light-emitting element.

According to this example, it was confirmed that the light-emitting element which is an embodiment of the present invention has characteristics as a light-emitting element and functions well. In addition, it was found that when the heterocyclic compound which is an embodiment of the present invention is used as a host of a green-light-emitting layer, a light-emitting element which exhibits favorable green light emission is obtained.

Example 7

In Example 7, a formation method of a light-emitting element having a different structure from the light-emitting element in Example 6 and measurement results of the element characteristics will be described. Specifically, a light-emitting element 2 formed using 4-(imidazo[1,2-a]pyridine-2-yl)-4'-(9H-carbazol-9-yl)triphenylamine (abbreviation: YGAPIM) which is described in Example 2 will be described.

The element structure of the light-emitting element 2 formed in this example is shown in Table 3. In Table 3, the mixture ratios are all represented in weight ratios.

TABLE 3

|  | 1st Electrode 1502 | 1st Layer 1511 | 2nd Layer 1512 | 3rd Layer 1513 | 4th Layer 1514 | 5th Layer 1515 | 2nd Electrode 1504 |
|---|---|---|---|---|---|---|---|
| Light-Emitting Element 2 | ITSO 110 nm | NPB:MoOx (=4:1) 50 nm | NPB 10 nm | YGAPIM:Ir(ppy)$_2$acac (=1:0.06) 30 nm | BCP 10 nm | Alq:Li (=1:0.01) 30 nm | Al 200 nm |

* Mixture Ratios Are All Represented In Weight Ratios

Hereinafter, the formation method of the light-emitting element 2 of this example is described. Structural formulae of organic compounds used in this example are shown below. Note that the organic compounds whose molecular structures are already shown in other examples are not shown in this example. The element structure is similar to that in Example 6, about which FIG. 19 is referred to.

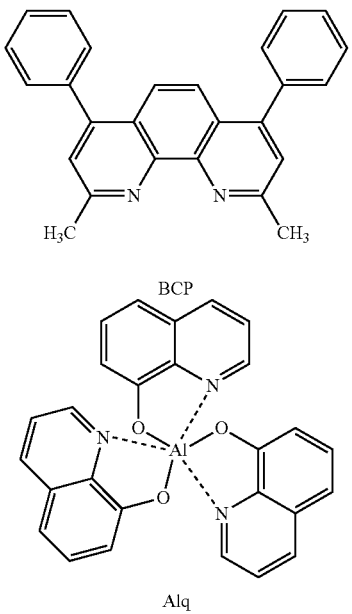

First, indium oxide-tin oxide containing silicon oxide was deposited on a substrate 1501 which was a glass substrate by a sputtering method to form a first electrode 1502. The thickness of the first electrode was 110 nm and the area thereof was 2 mm×2 mm.

Next, an EL layer 1503 in which a plurality of layers are stacked was formed over the first electrode 1502. In this example, the EL layer 1503 has a structure in which a first layer 1511 which is a hole-injecting layer, a second layer 1512 which is a hole-transporting layer, a third layer 1513 which is a light-emitting layer, a fourth layer 1514 which is an electron-transporting layer, and a fifth layer 1515 which is an electron-injecting layer are stacked in this order.

The substrate 1501 provided with the first electrode 1502 was fixed on a substrate holder that was provided in a vacuum evaporation apparatus so that a surface provided with the first electrode 1502 faced downward. The pressure in the vacuum evaporation apparatus was reduced to approximately $10^{-4}$ Pa. Then, on the first electrode 1502, 4,4'-bis[N-(1-naphthyl)-N-phenylamino]biphenyl (abbreviation: NPB) and molybdenum(VI) oxide were co-evaporated to form the first layer 1511 which was a hole-injecting layer. The thickness of the first layer 1511 was 50 nm, and the evaporation rate was adjusted so that the mass ratio of NPB to molybdenum(VI) oxide was 4:1 (=NPB:molybdenum oxide). Note that the co-evaporation method refers to an evaporation method in which evaporation is carried out from a plurality of evaporation sources at the same time in one treatment chamber.

Next, a 20-nm-thick film of a hole-transporting material was formed on the first layer 1511 by an evaporation method using resistance heating to form the second layer 1512 which was a hole-transporting layer. Note that for the second layer 1512, 4,4'-bis[N-(1-naphtyl)-N-phenylamino]biphenyl (abbreviation: NPB) was used.

Next, the third layer 1513 which was a light-emitting layer was formed on the second layer 1512 by an evaporation method using resistance heating. The third layer 1513 was formed by co-evaporation of 4-(imidazo[1,2-a]pyridin-2-yl)-4'-(9H-carbazol-9-yl)triphenylamine (abbreviation: YGAPIM) and (2-phenylpyridinato-N,$C^{2'}$)iridium(III)acetylacetonate (abbreviation: Ir(ppy)$_2$(acac)) to a thickness of 30 nm. Here, the evaporation rate was adjusted so that the mass ratio of YGAPIM to Ir(ppy)$_2$acac was 1:0.06 (=YGABOx:Ir(ppy)$_2$acac).

Furthermore, on the third layer 1513, bathocuproine (abbreviation: BCP) was formed by an evaporation method using resistance heating to a thickness of 10 nm to form the fourth layer 1514 which was an electron-transporting layer.

Then, the fifth layer 1515 which was an electron-injecting layer was formed by co-evaporation of tris(8-quinolinolato)aluminum(III) (abbreviation: Alq) and lithium (Li) to a thickness of 30 nm on the fourth layer 1514. Here, the evaporation rate was adjusted so that the weight ratio of Alq and Li was 1:0.01 (=Alq:Li).

Lastly, a 200-nm-thick film of aluminum was formed by an evaporation method using resistance heating to form the second electrode 1504. Thus, the light-emitting element 2 of this example was formed.

After the thus obtained light-emitting element 2 was sealed in a glove box under a nitrogen atmosphere so as not to be exposed to the air, operation characteristics of the light-emitting element were measured. Note that the measurement was carried out at room temperature (in an atmosphere in which the temperature was kept at 25° C.).

Figure 24:
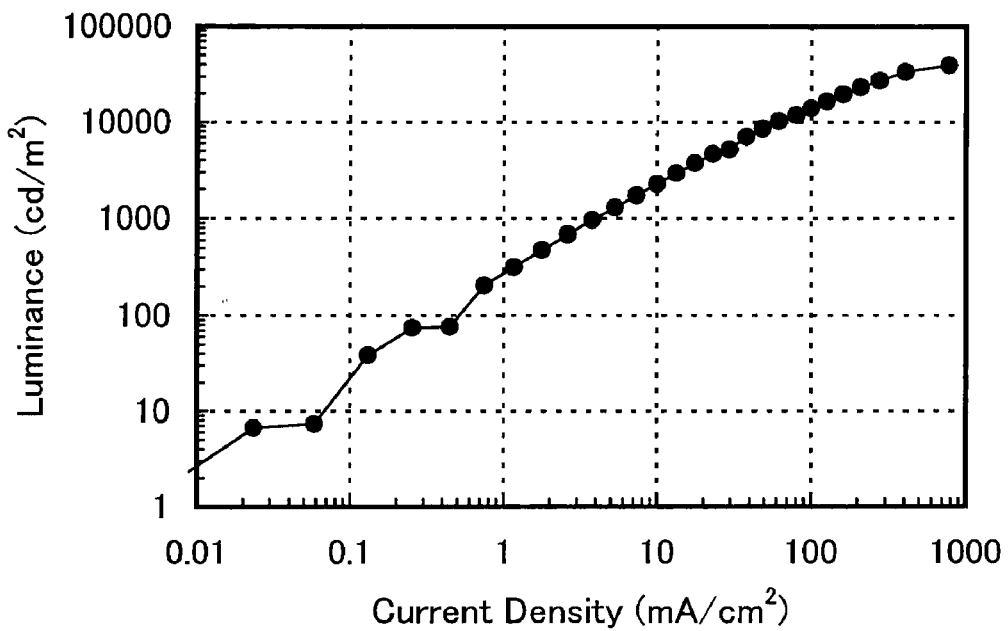
FIG. 24 is a graph showing current density-luminance characteristics of a light-emitting element 2.
Figure 25:
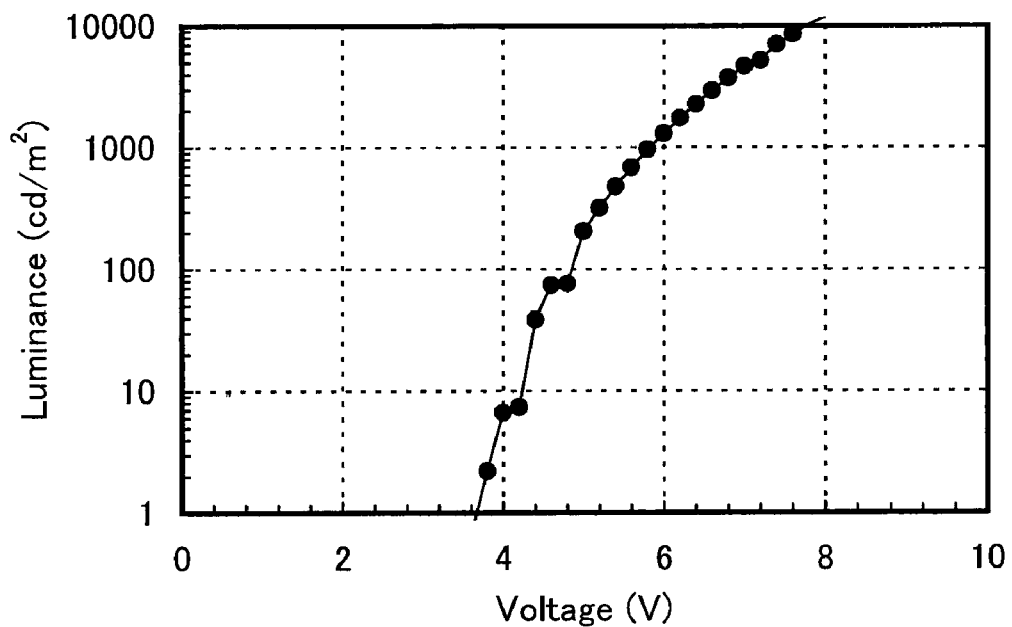
FIG. 25 is a graph showing voltage-luminance characteristics of the light-emitting element 2.
Figure 26:
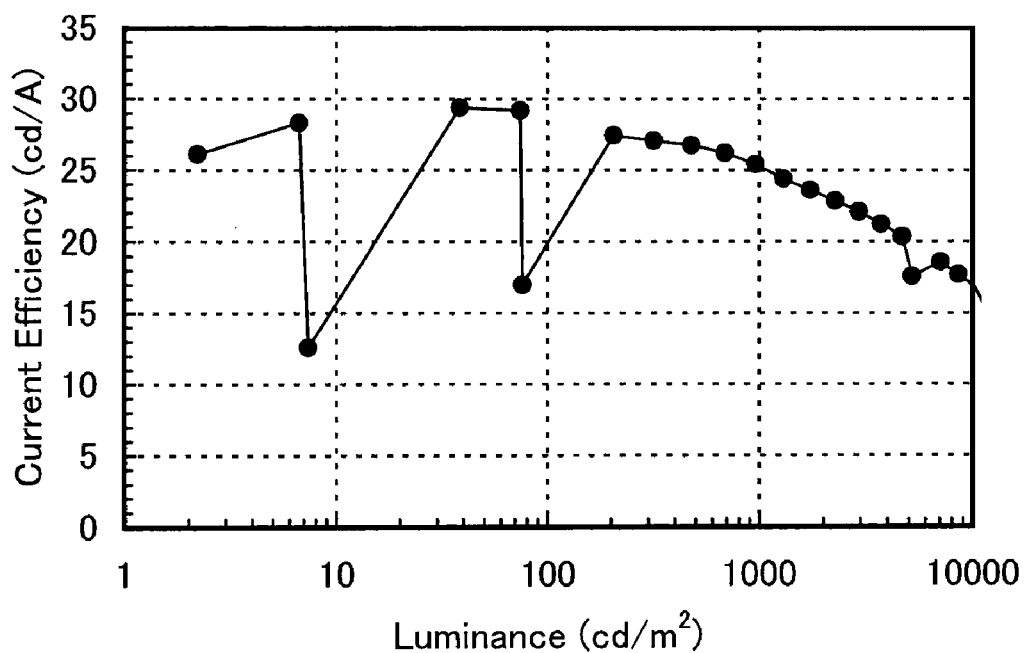
FIG. 26 is a graph showing luminance-current efficiency characteristics of the light-emitting element 2.

FIG. 24 shows the current density-luminance characteristics of the light-emitting element 2. FIG. 25 shows the voltage-luminance characteristics thereof. FIG. 26 shows the luminance-current efficiency characteristics thereof. In FIG. 24, the vertical axis represents luminance (cd/m$^2$) and the horizontal axis represents current density (mA/cm$^2$). In FIG. 25, the vertical axis represents luminance (cd/m$^2$) and the horizontal axis represents voltage (V). In FIG. 26, the vertical axis represents current efficiency (cd/A) and the horizontal axis represents luminance (cd/m$^2$). In addition, Table 4 shows the voltage, chromaticity, current efficiency, and quantum efficiency of the light-emitting element around 1000 cd/m$^2$.

TABLE 4

|  | Voltage (V) | Chromaticity (x, y) | current efficiency (cd/A) |
| --- | --- | --- | --- |
| Light-Emitting Element 2 | 5.8 | (0.35, 0.62) | 25.4 |

Figure 27:
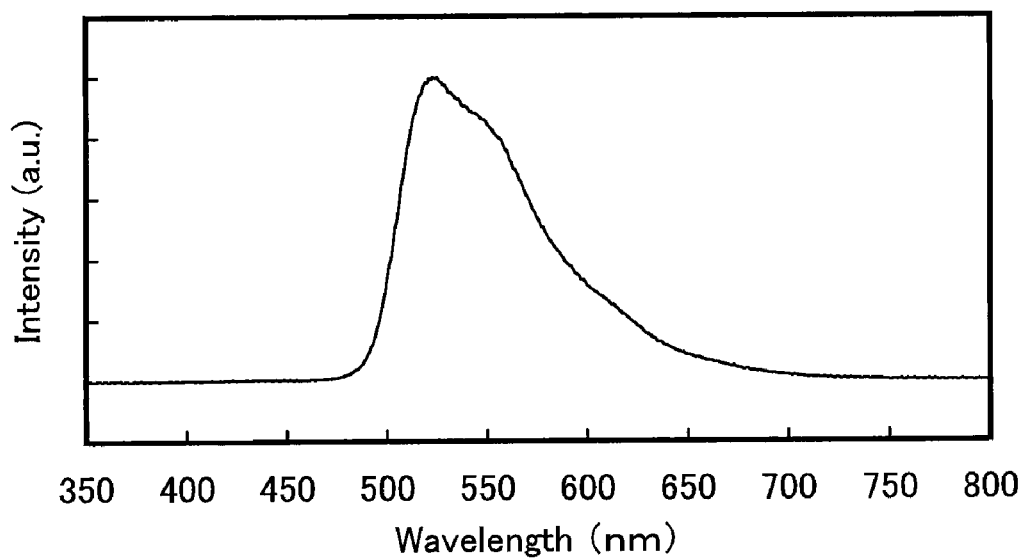
FIG. 27 is a graph showing an emission spectrum of the light-emitting element 2.

FIG. 27 shows the emission spectrum of the light-emitting element 2. As shown in FIG. 27, in the light-emitting element 2, a wavelength of green light, which is derived from Ir(ppy)$_2$acac that is a guest material, was observed, whereas an emission wavelength derived from YGAPIM that is a host material was not observed. Thus, it was found that the heterocyclic compound described in Embodiment 1 (YGAPIM in this example) functions as a bipolar host material in the light-emitting layer of the light-emitting element.

According to this example, it was confirmed that the light-emitting element which is an embodiment of the present invention has characteristics as a light-emitting element and functions well. In addition, it was found that when the heterocyclic compound which is an embodiment of the present invention is used as a host of a green-light-emitting layer, a light-emitting element which exhibits favorable green light emission is obtained.

Example 8

In Example 8, a formation method of a light-emitting element having a different structure from the light-emitting elements in Examples 6 and 7 and measurement results of the element characteristics will be described. Specifically, a light-emitting element 3 formed using N-[4-(imidazo[1,2-a]pyridin-2-yl)phenyl]-N,9-diphenyl-9H-carbazole-3-amine (abbreviation: PCAPIM) described in Example 3 will be described.

The element structure of the light-emitting element 3 formed in this example is shown in Table 5. In Table 5, the mixture ratios are all represented in weight ratios.

are already shown in other examples are not shown in this example. The element structure is similar to that in Example 6, about which FIG. 19 is referred to.

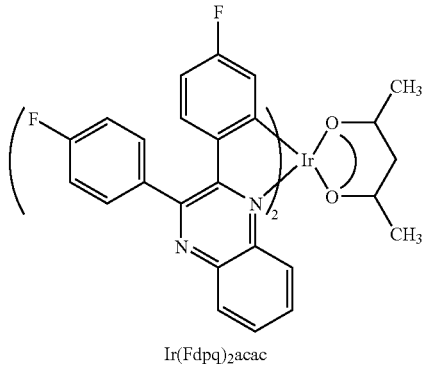

Ir(Fdpq)$_2$acac

In the light-emitting element 3 of this example, steps of forming up to and including the second layer 1512 which was a hole-transporting layer were similar to those of the light-emitting element 2 of Example 7.

Next, a third layer 1513 which was a light-emitting layer was formed on the second layer 1512 by an evaporation method using resistance heating. The third layer 1513 was formed by co-evaporation of N-[4-(imidazo[1,2-a]pyridin-2-yl)phenyl]-N,9-diphenyl-9H-carbazole-3-amine (abbreviation: PCAPIM) and bis[2,3-bis(4-fluorophenyl)quinoxalinato]iridium(III) acetylacetonato (abbreviation: Ir(Fdpq)$_2$acac) to a thickness of 30 nm. Here, the evaporation rate was adjusted so that the mass ratio of PCAPIM to Ir(Fdpq)$_2$acac was 1:0.08 (=PCAPIM:Ir(Fdpq)$_2$acac).

Furthermore, on the third layer 1513, bis(2-methyl-8-quinolinolato)(4-phenylphenolato)aluminum(III) (abbreviation: BAlq) was formed to a thickness of 10 nm to form a fourth layer 1514 which was an electron-transporting layer.

Then, a fifth layer 1515 which is an electron-injecting layer was formed by co-evaporation of tris(8-quinolinolato)aluminum(III) (abbreviation: Alq) and lithium (Li) to a thickness of 50 nm on the electron-transporting layer 1514. Here, the evaporation rate was adjusted so that the weight ratio of Alq and Li was 1:0.01 (=Alq:Li).

Lastly, a 200-nm-thick film of aluminum was formed by an evaporation method using resistance heating to form the second electrode 1504. Thus, the light-emitting element 3 of this example was formed.

After the thus obtained light-emitting element 3 was sealed in a glove box under a nitrogen atmosphere so as not to be

TABLE 5

|  | 1st Electrode 1502 | 1st Layer 1511 | 2nd Layer 1512 | 3rd Layer 1513 | 4th Layer 1514 | 5th Layer 1515 | 2nd Electrode 1504 |
| --- | --- | --- | --- | --- | --- | --- | --- |
| Light-Emitting Element 3 | ITSO 110 nm | NPB:MoOx (=4:1) 50 nm | NPB 10 nm | PCAPIM:Ir(Fdpq)$_2$acac (=1:0.08) 30 nm | BAlq 10 nm | Alq:Li (=1:0.01) 50 nm | Al 200 nm |

* Mixture Ratios Are All Represented In Weight Ratios

Hereinafter, the formation method of the light-emitting element 3 of this example is described. Structural formulae of organic compounds used in this example are shown below. Note that the organic compounds whose molecular structures exposed to the air, operation characteristics of the light-emitting element were measured. Note that the measurement was carried out at room temperature (in an atmosphere in which the temperature was kept at 25° C.).

Figure 28:
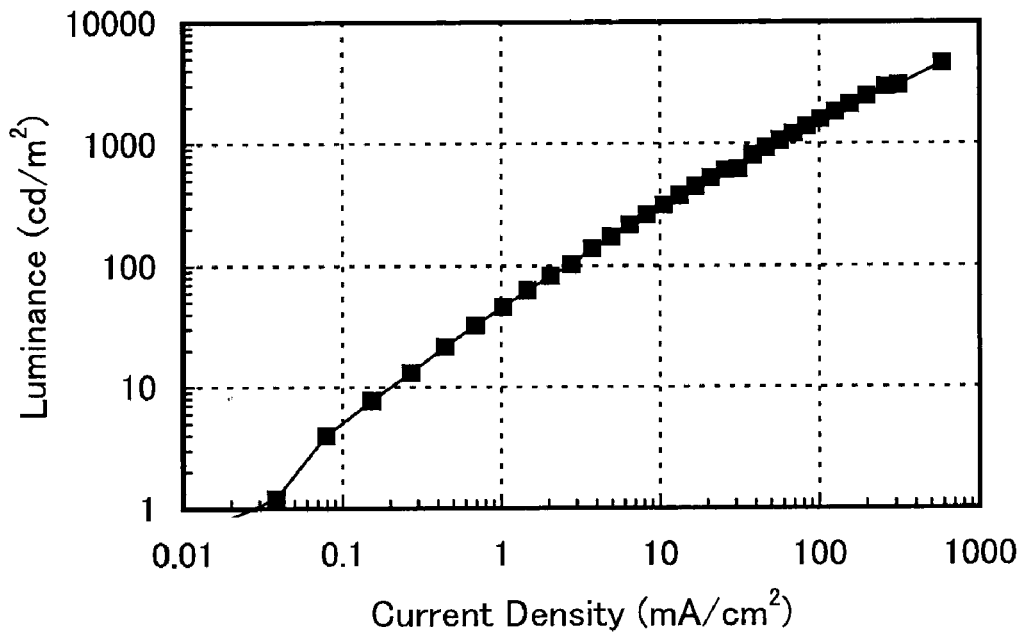
FIG. 28 is a graph showing current density-luminance characteristics of a light-emitting element 3.
Figure 29:
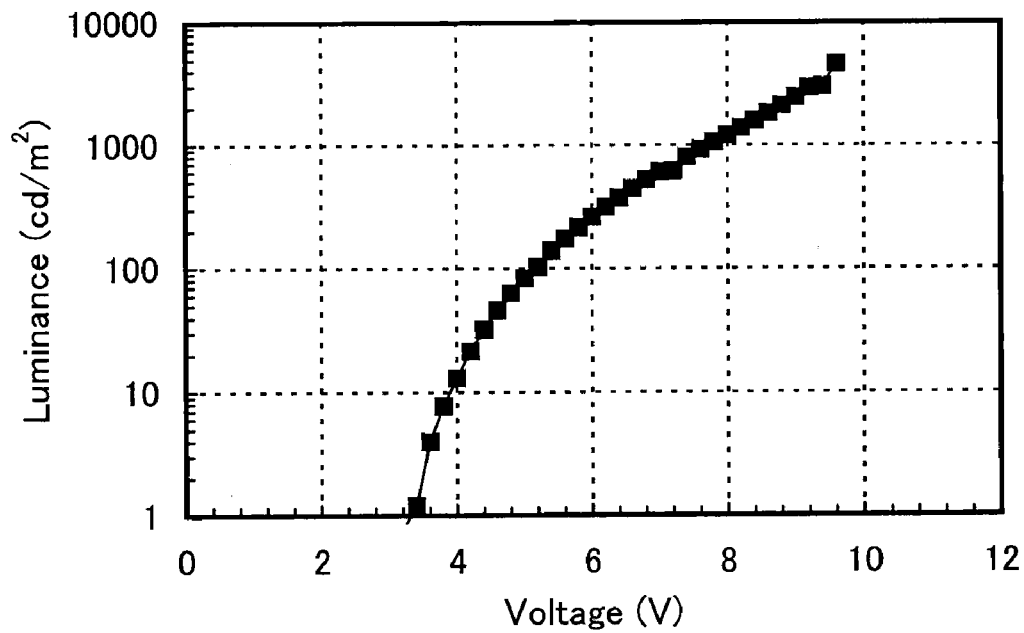
FIG. 29 is a graph showing voltage-luminance characteristics of the light-emitting element 3.
Figure 30:
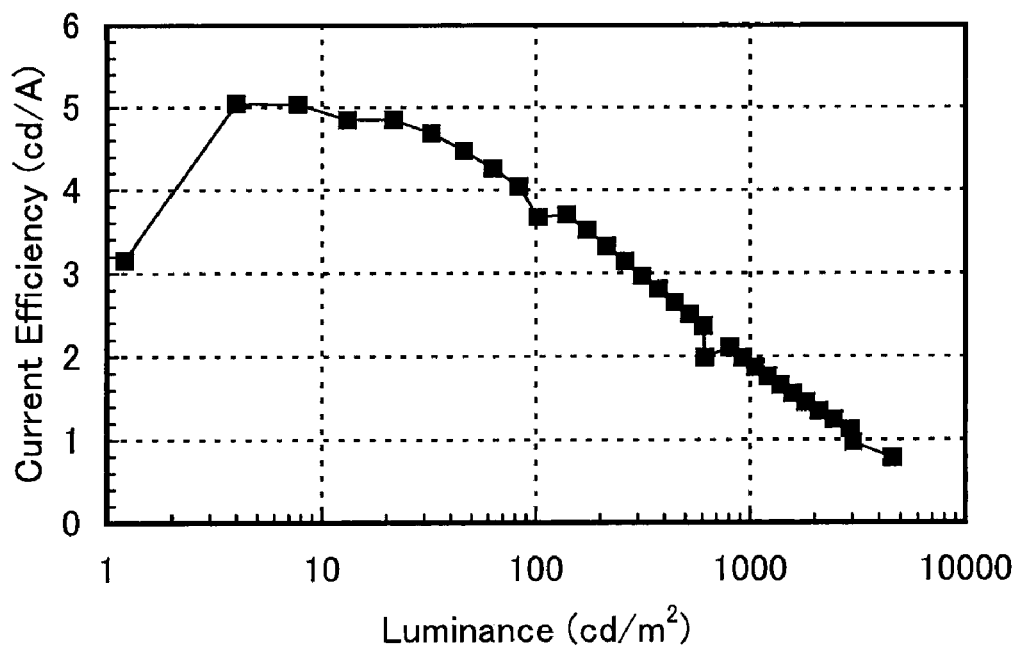
FIG. 30 is a graph showing luminance-current efficiency characteristics of the light-emitting element 3.

FIG. 28 shows the current density-luminance characteristics of the light-emitting element 3. FIG. 29 shows the voltage-luminance characteristics thereof. FIG. 30 shows the luminance-current efficiency characteristics thereof. In FIG. 28, the vertical axis represents luminance (cd/m$^2$) and the horizontal axis represents current density (mA/cm$^2$). In FIG. 29, the vertical axis represents luminance (cd/m$^2$) and the horizontal axis represents voltage (V). In FIG. 30, the vertical axis represents current efficiency (cd/A) and the horizontal axis represents luminance (cd/m$^2$). In addition, Table 6 shows the voltage, chromaticity, current efficiency, and quantum efficiency of the light-emitting element around 1000 cd/m$^2$.

TABLE 6

|  | Voltage (V) | Chromaticity (x, y) | current efficiency (cd/A) |
| --- | --- | --- | --- |
| Light-Emitting Element 3 | 7.8 | (0.70, 0.29) | 1.9 |

Figure 31:
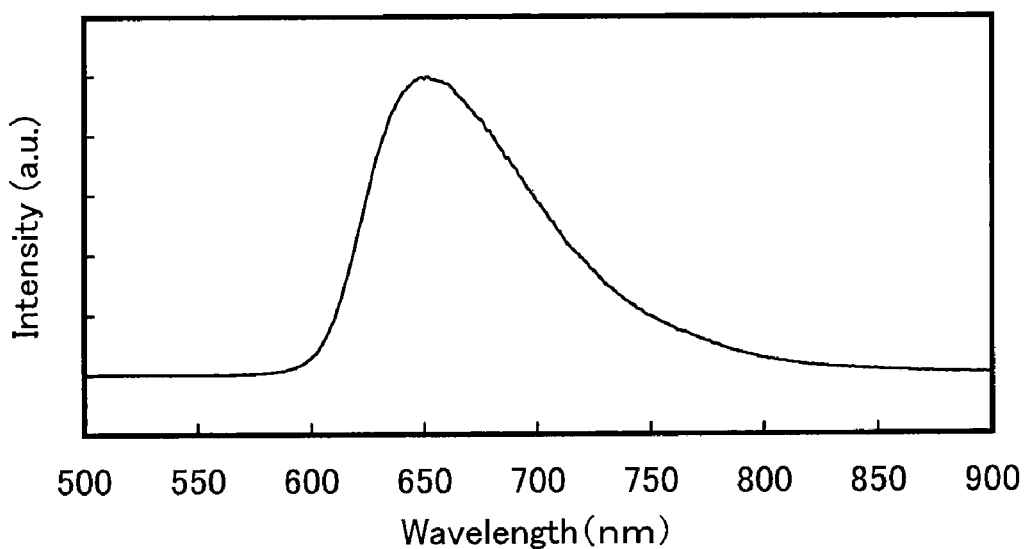
FIG. 31 is a graph showing an emission spectrum of the light-emitting element 3.

FIG. 31 shows the emission spectrum of the light-emitting element 2. As shown in FIG. 31, in the light-emitting element 3, a wavelength of red light, which is derived from Ir(Fdpq)$_2$acac that is a guest material, was observed, whereas an emission wavelength derived from PCAPIM that is a host material was not observed. Thus, it was found that the heterocyclic compound described in Embodiment 1 (PCAPIM in this example) functions as a bipolar host material in the light-emitting layer of the light-emitting element.

According to this example, it was confirmed that the light-emitting element which is an embodiment of the present invention has characteristics as a light-emitting element and functions well. In addition, it was found that when the heterocyclic compound which is an embodiment of the present invention is used as a host of a red-light-emitting layer, a light-emitting element which exhibits favorable red light emission is obtained.

This application is based on Japanese Patent Application serial no. 2009-086617 filed with Japan Patent Office on Mar. 31, 2009, the entire contents of which are hereby incorporated by reference.

What is claimed is:

1. A heterocyclic compound represented by the following formula (G1),

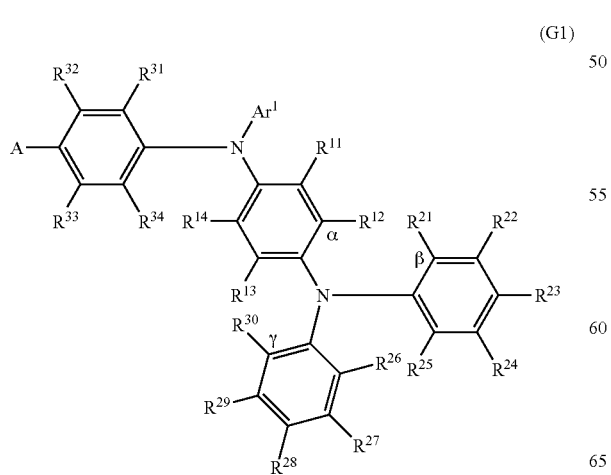

(G1)

wherein Ar$^1$ represents a substituted or unsubstituted aryl group having 6 to 10 carbon atoms which form a ring, wherein R$^{11}$ to R$^{14}$ and R$^{31}$ to R$^{34}$ each independently represent any one of a hydrogen atom, an alkyl group having 1 to 4 carbon atoms, or an aryl group having 6 to 10 carbon atoms which form a ring, wherein R$^{21}$ to R$^{30}$ each independently represent any one of a hydrogen atom, an alkyl group having 1 to 4 carbon atoms, or a substituted or unsubstituted aryl group having 6 to 10 carbon atoms which form a ring, wherein A represents a substituent represented by the following formula (S1-3), and

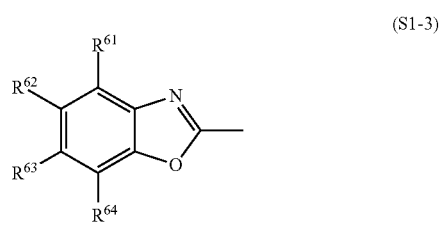

(S1-3)

wherein R$^{61}$ to R$^{64}$ each independently represent any one of a hydrogen atom, an alkyl group having 1 to 4 carbon atoms, or an aryl group having 6 to 10 carbon atoms which form a ring.

2. The heterocyclic compound according to claim 1, wherein A represents a substituent represented by the following structural formula (S2-2)

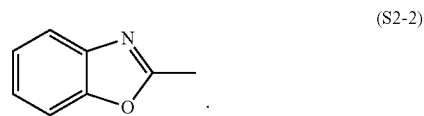

(S2-2)

3. The heterocyclic compound according to claim 2, wherein the heterocyclic compound is represented by the following formula (G2)

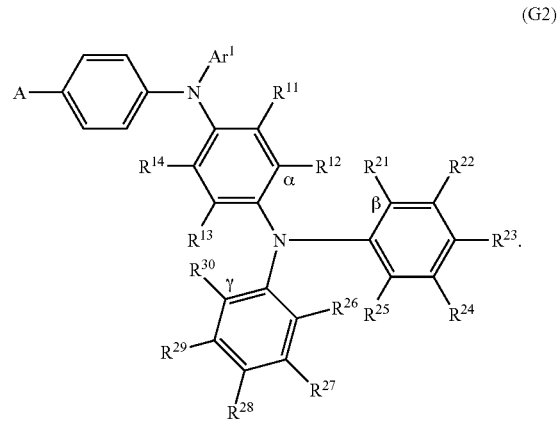

(G2)

4. The heterocyclic compound according to claim 3, wherein the heterocyclic compound is represented by the following formula (G3)

(G3)

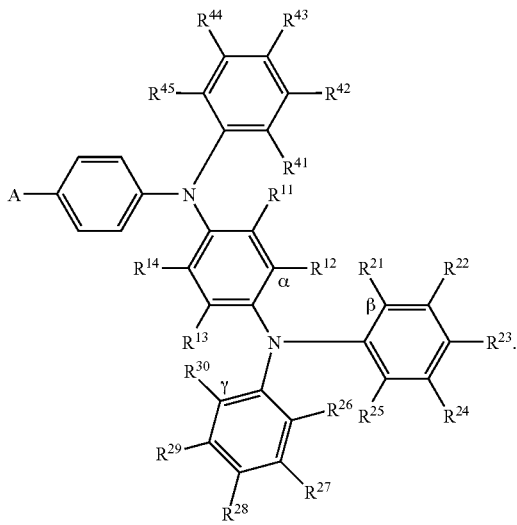

5. The heterocyclic compound according to claim 4,
wherein the heterocyclic compound represented by the following formula (G4)

(G4)

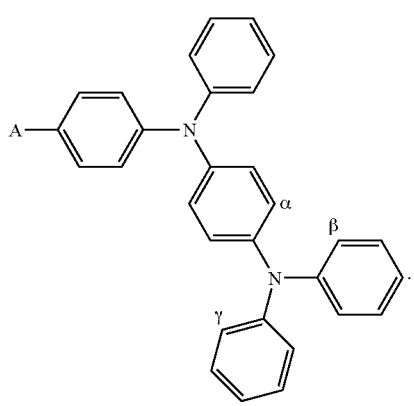

6. The heterocyclic compound according to claim 1,
wherein any two of a carbon atom α, a carbon atom β, and a carbon atom γ are combined to form a carbazole ring.

7. A light-emitting element comprising a light-emitting layer,
wherein the light-emitting layer comprises a heterocyclic compound represented by the following formula (G1), (G1)

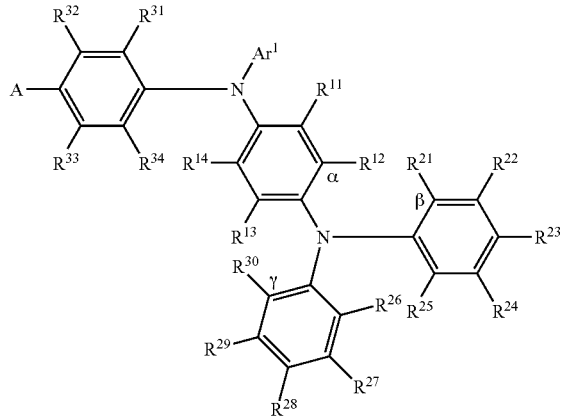

wherein Ar¹ represents a substituted or unsubstituted aryl group having 6 to 10 carbon atoms which form a ring, wherein $R^{11}$ to $R^{14}$ and $R^{31}$ to $R^{34}$ each independently represent any one of a hydrogen atom, an alkyl group having 1 to 4 carbon atoms, or an aryl group having 6 to 10 carbon atoms which form a ring, wherein $R^{21}$ to $R^{30}$ each independently represent any one of a hydrogen atom, an alkyl group having 1 to 4 carbon atoms, or a substituted or unsubstituted aryl group having 6 to 10 carbon atoms which form a ring, wherein A represents a substituent represented by the following formula (S1-3), and (S1-3)

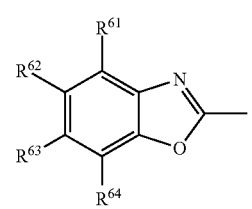

wherein $R^{61}$ to $R^{64}$ each independently represent any one of a hydrogen atom, an alkyl group having 1 to 4 carbon atoms, or an aryl group having 6 to 10 carbon atoms which form a ring.

8. The light-emitting element according to claim 7,
wherein the light-emitting layer further comprises a light-emitting substance.

9. The light-emitting element according to claim 8,
wherein the light-emitting substance is a phosphorescent compound.

10. A light-emitting element comprising:
a light-emitting layer; and
a layer containing a heterocyclic compound represented by the following formula (G1)

(G1)

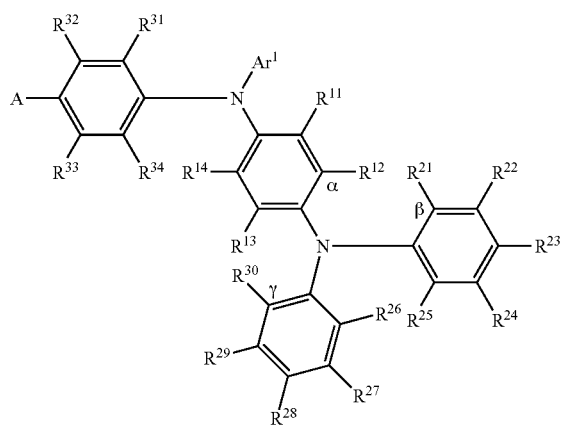

wherein Ar¹ represents a substituted or unsubstituted aryl group having 6 to 10 carbon atoms which form a ring, wherein $R^{11}$ to $R^{14}$ and $R^{31}$ to $R^{34}$ each independently represent any one of a hydrogen atom, an alkyl group having 1 to 4 carbon atoms, or an aryl group having 6 to 10 carbon atoms which form a ring, wherein $R^{21}$ to $R^{30}$ each independently represent any one of a hydrogen atom, an alkyl group having 1 to 4 carbon atoms, or a substituted or unsubstituted aryl group having 6 to 10 carbon atoms which form a ring, wherein A represents a substituent represented by the following formula (S1-3), wherein $R^{61}$ to $R^{64}$ each independently represent any one of a hydrogen atom, an alkyl group having 1 to 4 carbon atoms, or an aryl group having 6 to 10 carbon atoms which form a ring, and wherein the layer containing the heterocyclic compound is in contact with the light-emitting layer.

11. A light-emitting device comprising the light-emitting element according to claim 7.

12. An electronic device comprising the light-emitting device according to claim 11.

13. A lighting device comprising the light-emitting device according to claim 11.

14. A light-emitting device comprising the light-emitting element according to claim 10.

15. An electronic device comprising the light-emitting device according to claim 14.

16. A lighting device comprising the light-emitting device according to claim 14.

\* \* \* \* \*